US012491327B1

(12) United States Patent
Tóth et al.

(10) Patent No.: US 12,491,327 B1
(45) Date of Patent: Dec. 9, 2025

(54) LARYNGEAL MASK

(71) Applicant: innoMask Technologies Kft., Kecskemét (HU)

(72) Inventors: Zoltán Márton Tóth, Sopron (HU); Nóra Rédly, Budapest (HU); Edit Bodó, Gyula (HU); Tass Bertalan Adorján, Kecskemét (HU)

(73) Assignee: innoMask Technologies Kft., Kecskemét (HU)

( * ) Notice: Subject to any disclaimer, the term of this patent is extended or adjusted under 35 U.S.C. 154(b) by 0 days.

(21) Appl. No.: 19/297,835

(22) Filed: Aug. 12, 2025

Related U.S. Application Data

(63) Continuation of application No. 19/079,819, filed on Mar. 14, 2025.

(51) Int. Cl.
*A61M 16/04* (2006.01)
*A61M 16/20* (2006.01)

(52) U.S. Cl.
CPC ........ *A61M 16/0402* (2014.02); *A61M 16/20* (2013.01); *A61M 2210/1028* (2013.01)

(58) Field of Classification Search
CPC ........... A61B 1/00135; A61B 1/00154; A61M 16/0497; A61M 16/0402
See application file for complete search history.

(56) References Cited

U.S. PATENT DOCUMENTS

| | | | | |
|---|---|---|---|---|
| 9,974,912 | B2 * | 5/2018 | Brain | A61M 16/0493 |
| 11,235,116 | B2 * | 2/2022 | Toth | A61M 16/0429 |
| 2009/0194113 | A1 * | 8/2009 | Chen | A61M 16/04<br>128/207.14 |

* cited by examiner

*Primary Examiner* — Margaret M Luarca
(74) *Attorney, Agent, or Firm* — Wood Herron & Evans LLP

(57) ABSTRACT

The invention is a laryngeal mask, comprising a head portion (10) and a tube portion (14), an annular cushion (25) connected to the head portion (10), and a cover element (12) for the annular cushion (25), having a second puller portion (47), made of a through-breathable material, and a release element fixing the cover element (12) to the head portion (10), having a first puller portion (48), the puller portions (47, 48) are pullable at the tube proximal end of the tube portion (14), and the release element releases fixing of the cover element (12) in case the first puller portion (48) is pulled, wherein the puller portions (47, 48) are configured so that in case of joint pulling thereof, fixing of the cover element (12) to the head portion (10) is releasable and thereby making the cover element (12) removable.

14 Claims, 50 Drawing Sheets

LARYNGEAL MASK

This application claims priority, as a continuation application of U.S. application Ser. No. 19/079,819, which was filed Mar. 14, 2025, the contents of which is expressly incorporated by reference herein, in its entirety.

TECHNICAL FIELD

The invention relates to a laryngeal mask.

BACKGROUND ART

The laryngeal mask is a medical device applied e.g. in anesthesiology or in emergency situations, used for providing and maintaining airway. The laryngeal mask is to be driven through the oral cavity to its application position, where the laryngeal opening of the mask lies on the laryngeal inlet of the trachea in the larynx.

For this application, several laryngeal masks are known in the prior art.

In U.S. Pat. No. 11,235,116 B2 a laryngeal mask is disclosed, wherein a covering element is applied for folding the annular cushion inside an inner space, and wherein the covering element can be removed from outside. Although this approach objected to reach a smaller head size during the insertion the laryngeal mask into the anatomy (see the corresponding relevant aspects in the document), this approach has drawbacks in connection with its operation, namely that tearing of the covering element is applied when it is removed, as a consequence, residuals of the covering element are left after its removal. Beside the residuals, any tearing could result in sharp surfaces, which could be traumatic to tissues and therefore might result in device safety risks and issues.

In WO 2015/015233 A1 a laryngeal mask is disclosed in which a recess is formed on the circumference of the head portion for accommodating the material of the annular cushion before inflation. It is a disadvantage of this prior art laryngeal mask that its concept is not elaborated.

In view of the known approaches, there is a need for a laryngeal mask having small head size compared to the known approaches, but which is lack of the drawbacks of the known approaches.

DESCRIPTION OF THE INVENTION

The primary object of the invention is to provide a laryngeal mask which is free of the disadvantages of prior art approaches to the greatest possible extent.

An object of the invention is to provide a laryngeal mask, which has a small head size, but which has advantages in connection with its realization as well as in its operation, namely it is an object of the invention to avoid leaving residuals of the cover element after its removal and solving risk and safety issues of the prior art approach.

The objects of the invention can be achieved by providing the connection device according to claim 1. Preferred embodiments of the invention are defined in the dependent claims.

BRIEF DESCRIPTION OF THE DRAWINGS

Preferred embodiments of the invention are described below by way of example with reference to the drawings, where.

MODES FOR CARRYING OUT THE INVENTION

Figure 1:
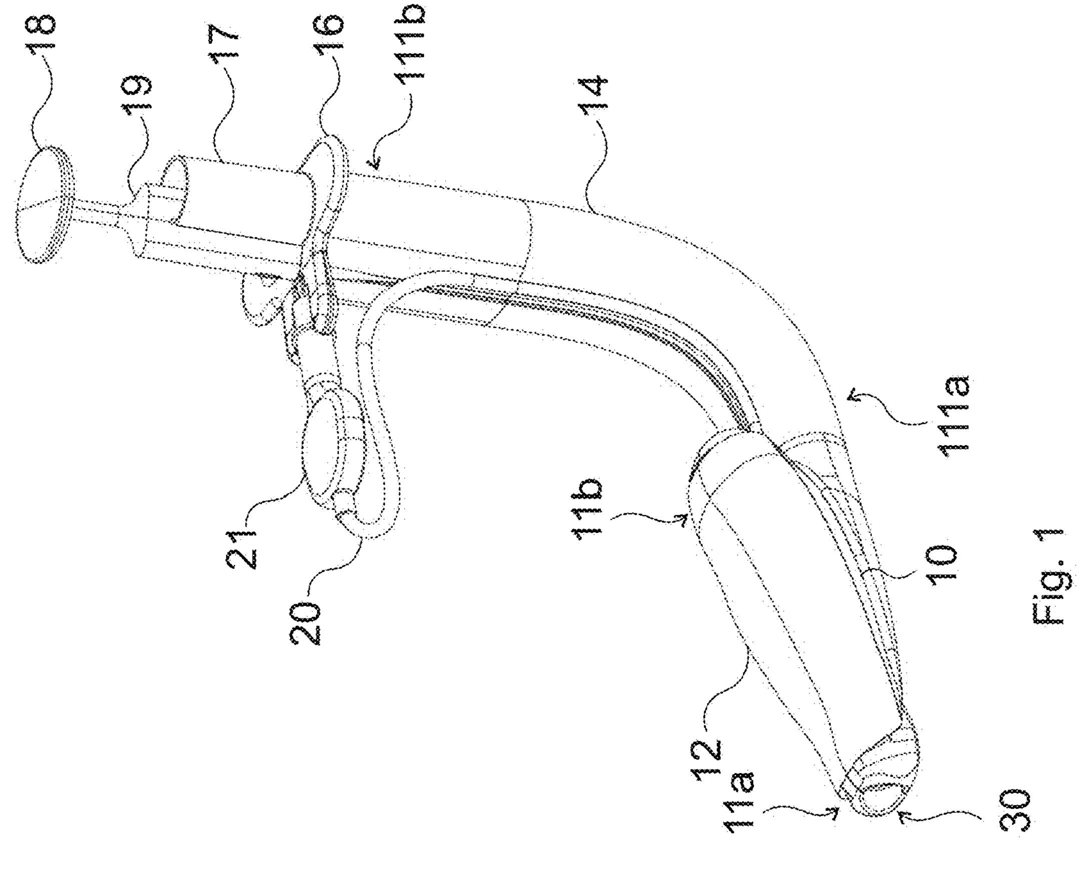
FIG. 1 illustrates a first embodiment of the invention in a spatial view.
Figure 3:
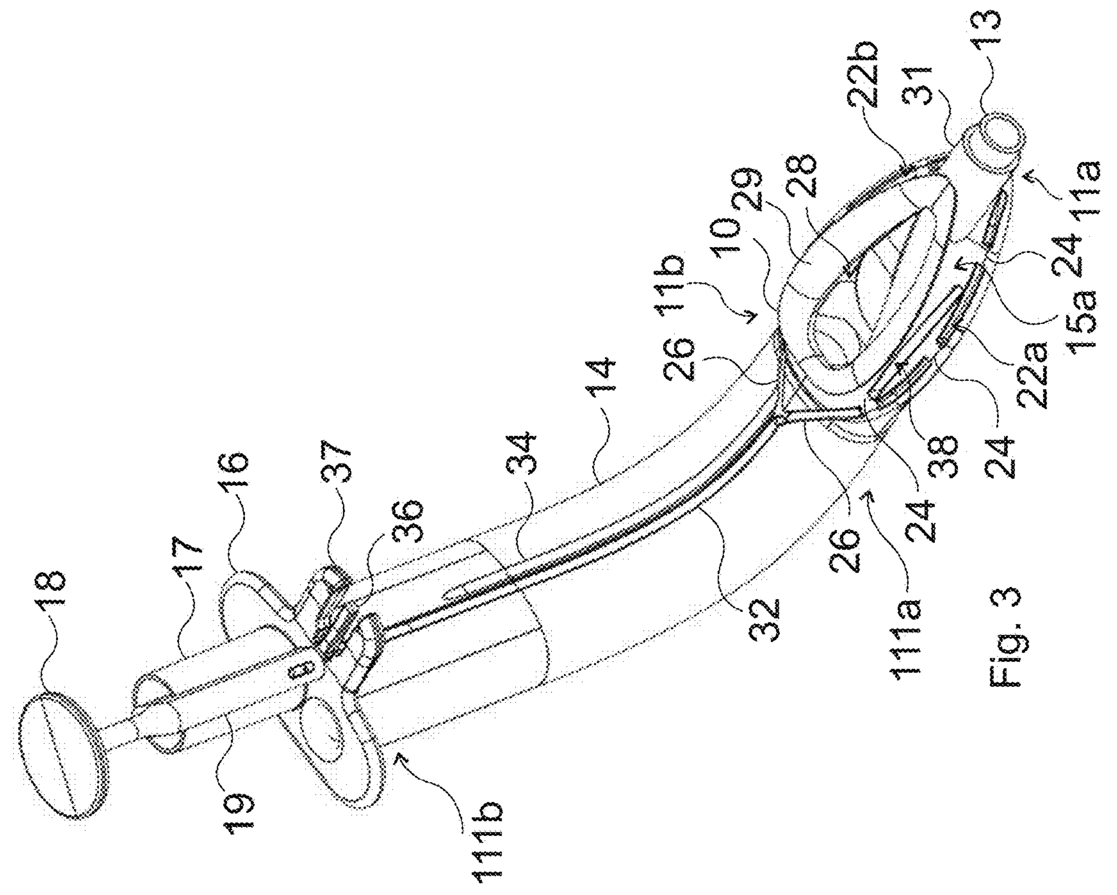

The invention is a laryngeal mask, which comprises a head portion having a head distal end and a head proximal end, and a tube portion having a tube distal end and a tube proximal end opposite to the tube distal end, wherein the tube distal end of the tube portion is arranged on the head proximal end of the head portion, a channel is formed between a laryngeal opening of the head portion and the tube proximal end of the tube portion (this is an inner/internal channel as illustrated by the figures; i.e. it is required that the head portion and the tube portion are configured so that to have an internal passage between the laryngeal opening and the tube proximal end; this a channel providing a passage to the laryngeal inlet of the trachea), and the laryngeal opening is adapted for fitting onto a trachea (according to the above, preferably specifically on the laryngeal inlet of the trachea in the larynx; it is noted that the head portion and the tube portion are made preferably as an integral part; the head portion may be called simply head, or head portion or head element; see FIGS. 1 and 3 for a head distal end 11*a* and a head proximal end 11*b* of a head portion 10, as well as for a tube distal end 111*a* and a tube proximal end 111*b* of a tube portion 14, which are not denoted in another embodiments, but these can be easily generalized for those), an annular cushion arranged on the head portion (i.e. connected to the head portion) around the laryngeal opening, and a cover element at least partly encompassing the annular cushion and at least partly covering the laryngeal opening (it may be also called covering element).

It is noted that the tube portion is thus a tube, may be called also introductory tube, mask tube, passage tube or simply tube. The respective distal ends and proximal ends may be called also first ends and second ends. Proximal end of a component is always that end which is closer to the user and the distal end is the other end being distant from the user in use.

In connection with the annular cushion, it is noted that annular has a meaning in connection with the cushion that it is annular, i.e. has portions annularly, that is on the whole circumference: e.g. normal or reinforced cushion portions—there can be reinforcement parts in the cushion as an internal structure thereof—, and also a portion encompassing the gastric tube in case it is arranged, i.e. a portion arranged around the gastric tube. The annular cushion may be called simply cushion, and it is noted that in the respective technical field the annular cushion is often called a cuff or balloon. The annular cushion fits to the anatomy, thereby preferably providing seal around the trachea, namely around the laryngeal inlet of the trachea in the larynx, besides, providing preferably sealed access to the esophagus (via the gastric tube). It is also noted that the annular nature is meant on the material of the cushion, but also—see passages on the front in FIGS. 56 and 67—the inflated inner space is preferably annular, i.e. goes around.

Furthermore, the followings are noted in connection with that the cover element at least partly encompasses (surrounds) the annular cushion and at least partly covers the laryngeal opening (these apply in the assembled state, otherwise the cover element is adapted for these tasks).

Figure 80:
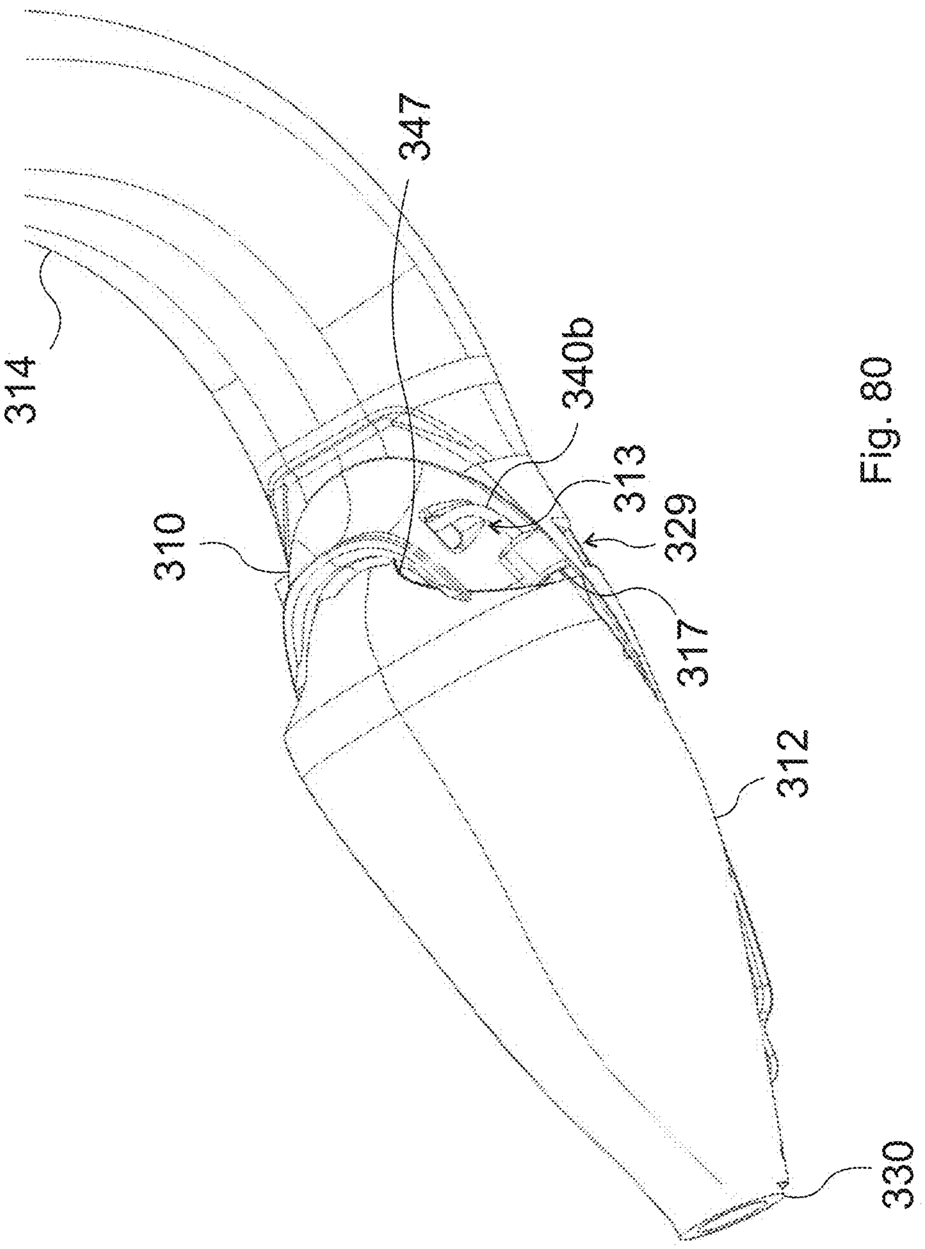
FIG. 80 illustrates a fifth embodiment of the invention without the cushion element, but with the cover element for illustration.

As shown also in the figures, e.g. FIG. 1, the term that the cover element at least partly encompasses the annular cushion means that the cover element encompasses the annular cushion practically along the edges of the head portion between the head distal end and the head proximal end, but full encompassing is not required (in FIG. 1 there is no encompassing both at the head distal end and the head proximal end, in FIG. 80 there is lesser encompassing at the head proximal end, bit there is (substantially) full encompassing at the head distal end). On the other hand, (substantially) full encompassing is also conceivable which means that beside encompassing along the head portion edges the cover element encompasses (i.e. there: covers) the annular cushion also elsewhere. Naturally, the cover element encompasses the annular cushion from an opposite direction vis-à-vis the head portion, since the cover element is arranged on the head portion. In other words, naturally, the cover element encompasses the open surfaces of the annular cushion.

In FIG. 1 the percentage of encompassing/covering-in accordance with the above meaning-seems to be above approx. 80%, in case of FIG. 80 it seems to be above 60% or 70%. Since these are the two main approaches, these percentages may be generally applied for other embodiments.

Figure 2:
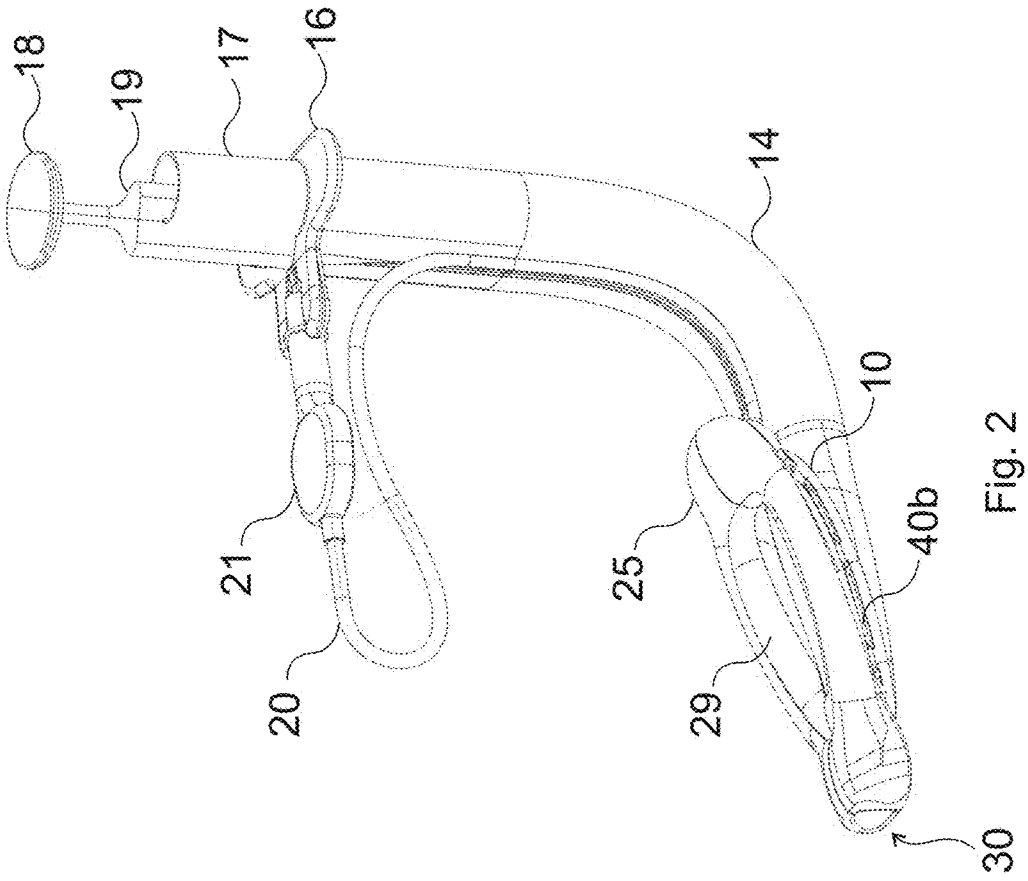
FIG. 2 shows the first embodiment of FIG. 1 without the cover element.

Furthermore, the term that the cover element at least partly covers the laryngeal opening (so, it is noted that this is about the laryngeal opening) means that the laryngeal opening is mainly covered but not a full covering is required. FIG. 80—depicted without an annular cushion—shows that the puller portion of the cover element goes into the laryngeal opening. Accordingly, in FIG. 80 substantially fully covering is applied, i.e. the laryngeal opening is covered in more than 90%, preferably more than 95%, substantially 100% (i.e. very close to 100%; these percentages can be generally said for the embodiments, since this is the least covered embodiment). Moreover, as FIG. 1 shows the laryngeal opening may also be fully covered. This can be understood if FIGS. 1 and 2 are interpreted together. Furthermore, in FIGS. 19-32, particularly in FIGS. 29-32 it is illustrated that the cover element extends very close to the head proximal end and the puller portion 47 is bent back to be led into the channel 46. It is noted furthermore, that FIGS. 29 and 30 illustrate that the laryngeal opening is ended (meaning: starting from the head distal end).

In the invention the cover element is made of a through-breathable material (see also below).

The laryngeal mask according to the invention further comprises:

- a release element fixing (connecting) the cover element to the head portion, wherein the release element has a first puller portion and the cover element has a second puller portion, the first puller portion and the second puller portion are pullable at the tube proximal end of the tube portion, and the release element is adapted for releasing its fixing of the cover element to the head portion in case the first puller portion of the release element is pulled at the tube proximal end of the tube portion (at the tube proximal end both the first and second puller portions are pullable, i.e. the cover element and the release element connected to these can be removed from outside, see also herebelow for further characterization; the release element fixes the cover element in the assembled state, otherwise it is adapted for fixing it).

It is noted that the first puller portion and the second puller portion may also be called (release) thread puller portion and cover (element) puller portion, respectively.

In the invention, furthermore, the first puller portion and the second puller portion are configured so that in case of joint pulling of the first puller portion and the second puller portion at the tube proximal end of the tube portion, fixing with the release element of the cover element to the head portion is releasable and thereby making the cover element removable.

According to the above definition for the joint pulling, such a configuration is applied for the first puller portion and the second puller portion that the fixing is released first and thereby the cover element is made removable and can be removed in the course of the joint pulling (by continued, i.e. further pulling). The joint pulling is preferably made continuously, i.e., preferably, a continuous pulling is applied. According to the joint pulling it is also for pulling out also the cover element: pulling of the second puller element of which is part of the joint pulling.

Accordingly, a joint (common, simultaneous) pulling is applied on the first puller portion and the second puller portion. In other words, a single pulling is applied on the first and the second puller portion at the tube proximal end of the tube portion (this is in the assembled state these are configured, i.e. arranged this way; according to the above these are pullable at the tube proximal end of the tube portion). It is thus noted that the first puller portion and the second puller portion are pulled jointly (it is a simultaneous activation) at the tube proximal end of the tube portion, but—because of the configuration—the displacement of the release element and the cover element occurs consecutively (shifted) in time. The joint pulling is naturally terminated when both the release element and the cover element have been removed from the laryngeal mask.

The joint pulling is preferably made possible in a way that the respective ends of the first and second puller element at the tube portion are pulled at the same time (together, in common), but the release element—e.g. the preferably applied release threads—become tight first (or these are tight from the beginning, see also below), so that can be pulled out. Afterwards when these pulled further in common, the second puller portion of the cover element become tight, so that the cover element can also be pulled out. In connection with the joint pulling, see also the description after FIGS. 17A-18.

The above definition is independent from that a gastric tube is arranged or not. As the figures illustrate, the gastric tube can be a part of the laryngeal mask in a natural way. The components are adjusted to the arrangement of the gastric, mainly the configuration of the annular cushion, but also other components like the threading elements (these would be similarly arranged also in the lack of the gastric tube) or like the head portion edge on which it has influence. As illustrated, the gastric tube comes out from the annular cushion at the distal tip, the cover element covers that part—if extends there—similarly with or without gastric tube.

In the above definition and in some further definitions of optional features, the laryngeal mask is described in its assembled state, i.e. when it is assembled, thus, the respective components are arranged in it. As touched upon at some points such an approach could also be applied for describing the laryngeal mask, which is not based on the assembled state but also discloses the components and their relationship.

According to the above definition, the invention comprises in every embodiment thereof:

- a head portion denoted by a reference numeral in each of the embodiments; accordingly, see head portions 10, 110, 210, 310, 360 410 in the following description for the respective embodiments (for the head portion 10 in the first embodiment, see e.g. FIGS. 1-2);
- an annular cushion and a cover element, which are not denoted (or even shown) in every embodiment; in the following see annular cushions 25, 85, 125, 325 and cover elements 12, 82, 212 for certain embodiments (for the annular cushion 25 and the cover element 12 in the first embodiment, see e.g. FIGS. 1-2);
- a release element, for the implementation of which, see the following description (in the first embodiment, release threads 40*a*, 40*b* are introduced in connection with FIGS. 5-7).

It is noted, furthermore, that the laryngeal mask comprises in every embodiment an tube portion (see tube portions 14,114 and 314 in the figures), and a laryngeal opening of the head portion, adapted for fitting onto a trachea is also denoted in many embodiments (see laryngeal openings 28, 228, 328, 428 in the figures).

The above components which are comprised in every embodiment can be easily identified in the respective embodiments, even if these are not illustrated, like the annular cushion in the fourth and seventh embodiments (see e.g. FIGS. 71 and 85), cover element in the sixth and seventh embodiment (see e.g. FIGS. 84 and 85), and the release element in the seventh embodiment (see e.g. FIG. 85), where the threading groove for the release thread as the release element is shown.

It is summarized in connection with the above definition of the laryngeal mask according to the invention, referring to the above referenced figures (FIGS. 1, 2 and 5-7) that the presence of the head portion, annular cushion and cover element (made of a through-breathable material) is required in the most general form of the invention and also a release element which can be implemented for example by release threads, but in the above definition only the followings are required for the release element which is adapted for fixing the cover element to the head portion (see the definition for the details):

its first puller portion is pullable from side, at the tube proximal end of the tube portion (in other words, it has a release element operable-can be grabbed-from outside), and appropriate configuration for a joint pulling of its first puller portion and the second puller portion of the cover element, for first releasing the fixing of the cover element to the head portion, and, after that, removing the cover element.

With these, the requirements in the definition of the invention are fulfilled. It is emphasized that these requirements can be fulfilled not only with applying the release threads but also other solutions for the release element are conceivable.

It is emphasized that with the help of applying the release element (e.g. release threads) according to the invention, the release element and the cover element fully leave the device when these are operated, i.e. the laryngeal mask is prepared for usage in its destination place in the anatomy. Accordingly, nothing is left from these in the device (no residual remain in the device).

The through-breathable material is a material through which breathing is allowed (i.e. the breathing is possible, it is not blocked). This is because, it is thus ensured that breathing is possible when the laryngeal mask has reached its final destination (i.e. the destination place in the anatomy), but it is still covered by the cover element. The through-breathable material is adapted for through-breathing of breathing generated by a breathing machine and/or the own breathing of the patient. Accordingly, it maintains the airway always, even when the laryngeal mask is in its destination place.

The through-breathable material is preferably a cutout—e.g. a laser-cut—from a sheet of material chosen to be atraumatic and have such a configuration which allows being breathed through in a manner as detailed above. The material is preferably bendable like the surgical meshes (nets)—which can be utilized for the cover element—or like gauze or a piece of cloth. Furthermore, it is preferable it is a non-stretchable material.

Accordingly, preferably it is not a continuous/uninterrupted material which could block breathing, but it is a noncontinuous/interrupted material in the meaning below. This type of material can be produced (manufactured) e.g. by weaving or knitting (to have a woven or knitted—i.e. noncontinuous/interrupted—material, which latter is widespread for surgical meshes), but other ways of production/manufacturing are also conceivable. The through-breathable material may be in a non-limiting example a (dense) plastic—e.g. nylon—net. Furthermore, in a more specific non-limiting example, a woven polyamide net with a thickness of 0.046 mm.

When we remove the cover element, the puller portion of it is pulled from outside in line with the joint pulling. Accordingly, it is pulled when the cover element is released from being fixed to the head portion, i.e. pulling it out will be facilitated. It is noted in this respect that since the cover element is made of a bendable (soft) material, the larger width of the head portion of the cover element is not a hindrance for pulling the cover element out. This also helps that the puller portion will not receive too much stress when pulled out, so the risk of tearing can be avoided (preferably only threading is applied for fixing). The second puller portion can be made to be integral with the cover element (i.e. with the further, main part thereof), an appropriate material can be chosen both for being through-breathable and to avoid tearing off the puller portion. However, these can also be connected to each other, the puller portion may be glued to the cover element.

Figure 7:
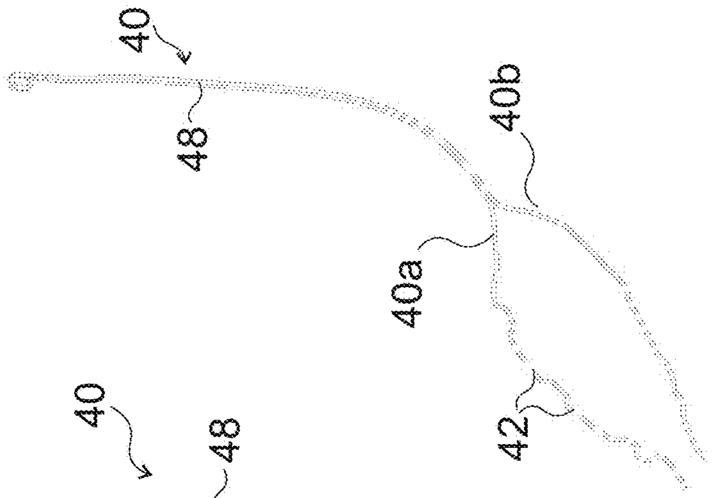
Figure 9A:
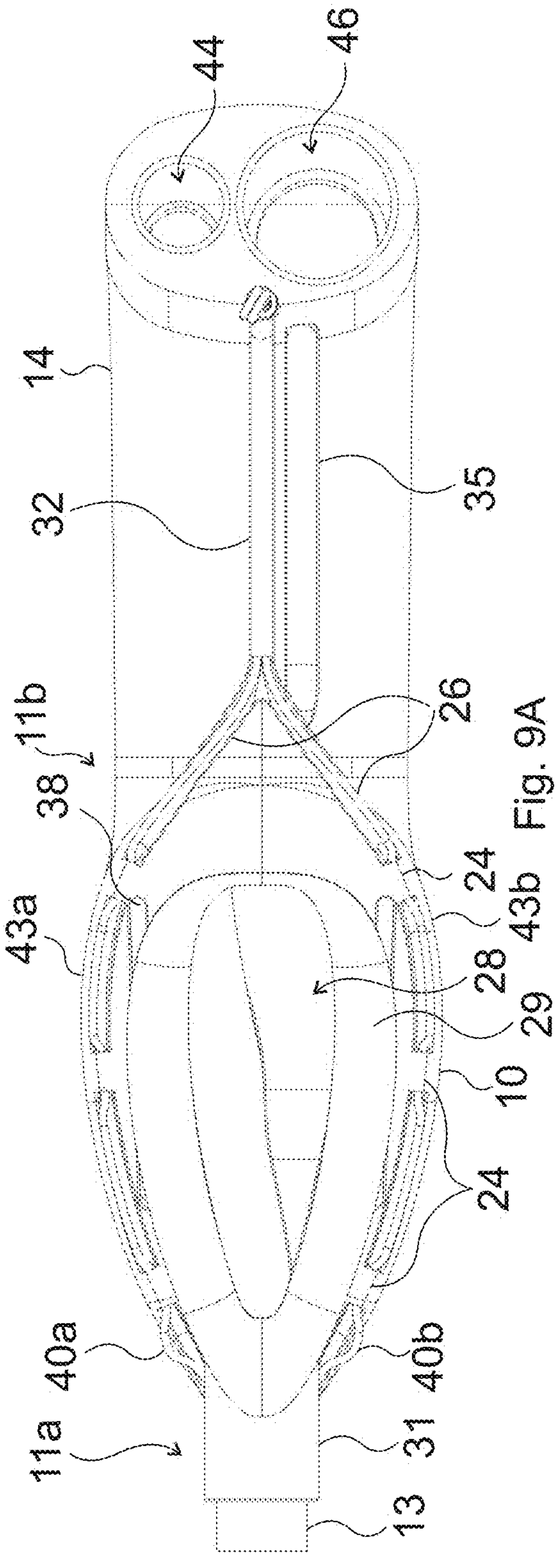
FIGS. 9A and 9B show the first embodiment of FIG. 1 from an upper view without the cover element and the annular cushion, and with and without release threads.
Figure 13:
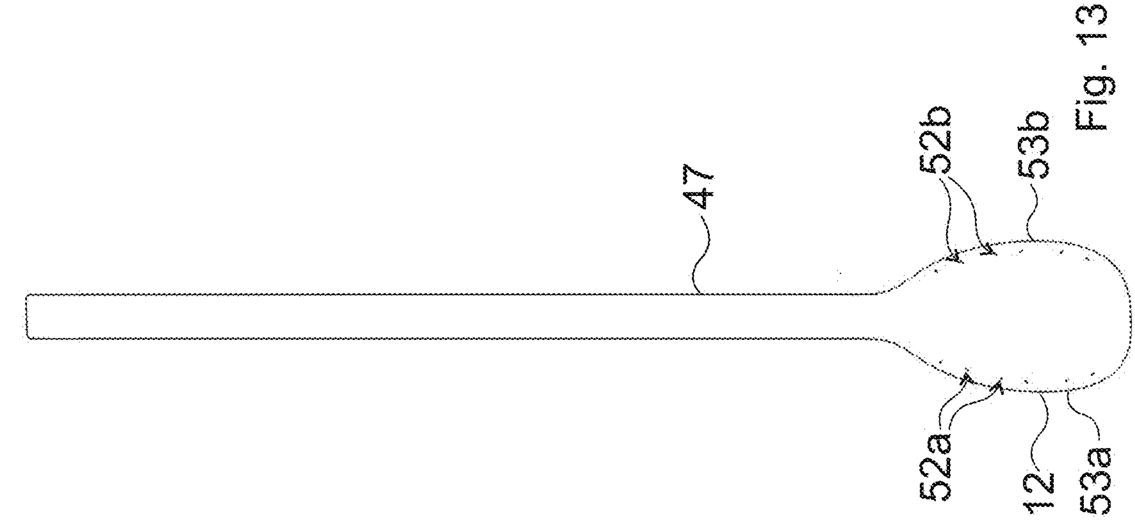
FIG. 13 illustrates the cover element in the first embodiment.
Figure 77:
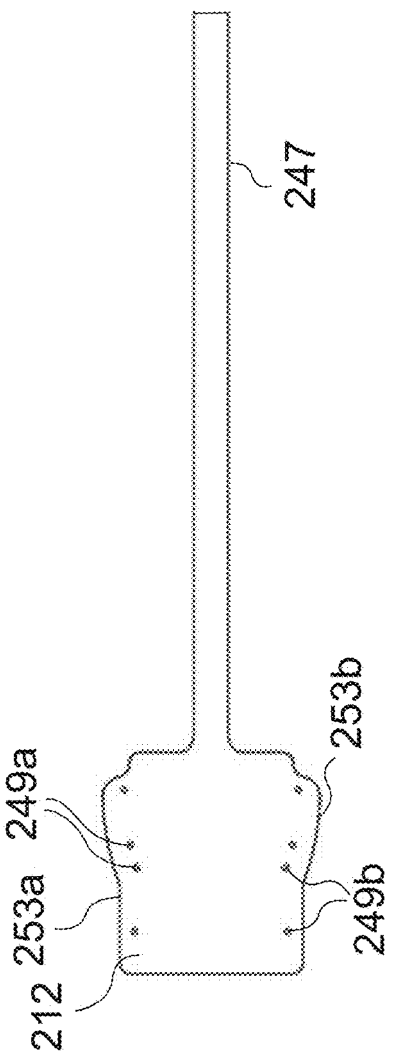
FIG. 77 illustrates the cover element of the fourth embodiment from an upper view.

In an embodiment, as mentioned above, the release element is implemented by means of release threads, in which embodiment the cover element has a first row of threading holes and a second row of threading holes along its respective cover element edges located (extending) between the head distal end and the head proximal end of the head portion (for the first embodiment see a first row of threading holes 52*a* and a second row of threading holes 52*b*, as well as a first cover element edge 53*a* and a second cover element edge 53*b* in FIG. 13; for further threading holes and cover element edges, see FIG. 77; these are also termed according to the assembled state; the holes are formed at the edges, i.e. the holes are close to the edges, since the cover element is preferred to be fixed at its edges), the laryngeal mask further comprises first threading elements and second threading elements formed on the head portion along its respective head portion edges extending between the head distal end and the head proximal end of the head portion (the threading element may be also called anchoring element or looping element, for the implementation of these, see below further, more specific embodiments; for exemplary head portion edges 43*a*, 43*b*, see FIG. 9A, these may be sharp edges or more or less—i.e. slightly—rounded edges), and the release element is formed—i.e. constituted—by a first release thread and a second release thread having a first puller portion (pullable at the tube proximal end of the tube portion, as required above from a first puller portion; see e.g. first puller portions 48 are formed on the respective release threads 40*a*, 40*b* in FIG. 7), arranged inserted into or passing through the first threading elements and the second threading elements (for these features, see also below), respectively, and passing through the first row of threading holes and the second row of threading holes, respectively, in a manner so as to fix the cover element along the respective cover element edges to the head portion (accordingly, the first and second release threads are arranged, i.e. threaded by the help of the first and second threading elements on the head portion and also via the threading holes in the cover element in a way that fixing of the cover element to the head portion is achieved; a way of appropriate threading is illustrated in the figures), wherein the first release thread and the second release thread are releasable from the first threading elements and the first row of threading holes, as well as from the second threading elements and the second row of threading holes, respectively.

It is noted that the threading element is an element for threading, more specifically, an element for threading the release thread through it (could be called thread-through element), in connection with the words: we can say that the release thread is threaded (is laced—the verb lace can also be used in connection with the corresponding elements) into the head portion using the respective threading holes of the cover element and the threading elements on the head portion.

Furthermore, in respective embodiments, the first release thread and the second release thread

- each has a respective (own) first puller portion (see also the next sections), or
- have a common first puller portion (when the first release thread and the second release thread have a common first puller portion, it can be e.g. conceived as a Y-shaped component; see also a comment on this at the description of FIG. 7).

Figures 17A, 17B, 17C, 17D, 18:
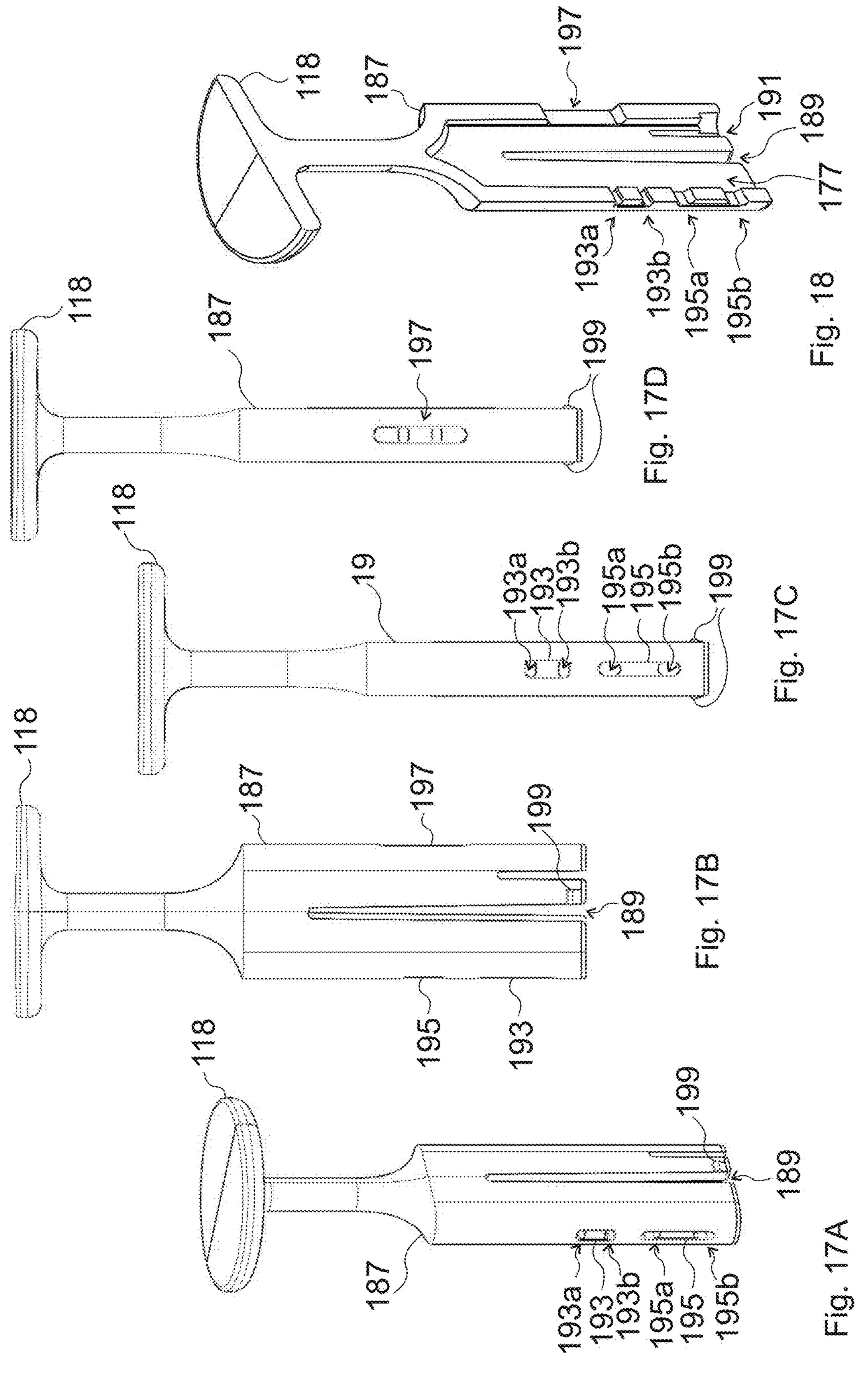
FIGS. 17A-17D show a pullable end element in different views.
FIG. 18 shows the pullable end element of FIGS. 17A-17D in a spatial-sectional view.

In an embodiment, the first release thread and the second release thread each has a respective first puller portion, and the first release thread and the second release thread are segments of a single thread (i.e. of a single continuous thread, see in this respect the description of FIGS. 17A-18).

In another embodiment, the first release thread and the second release thread each has a respective first puller portion, and the first release thread and the second release thread are separate threads (i.e. these are two separate pieces which are possibly connected to each other by their first puller portions e.g. by a knot, or connected to each other by the help of the pullable end element—which is configured in this case so that the separate pieces are connected to it).

The first puller portion can be the elongation of the release thread until the tube proximal end of the tube portion, which is not threaded into the head portion and the cover element. Accordingly, the release thread can be considered to be that part which is threaded into the head portion and the cover element (at the threaded part, there have to be two respective threads for the two side of the head portion). These can be differentiated based on FIG. 7 (see also below).

Furthermore, in accordance with the above (i.e. in both cases), the respective release threads—however, every piece of a thread may be called thread in itself—may also be called a release thread segment or a release thread portion (or even a release thread piece). It is noted that a release thread may also be called by other names, e.g. a release string or a pullable fix(ing) thread (pullable from outside and adapted for fixing the cover element) and it is threadable.

In the followings we do not consider whether the release threads are separate or portions of a single thread. The release threads are treated this way since for fixing the cover element on the two sides, two free ended threads are needed and described. Thus, in this respect, the configuration of their other ends is not relevant, does not play a role in their task (i.e. fixing and releasing). It is noted, furthermore, that in some cases the release threads are not denoted by the reference numbers at the threaded part for practical reasons, but somewhere on the thread (e.g. on the elongation). These might be replaced onto the threaded part of these.

Furthermore, preferably (in a variant of the embodiment applying release threads as the release element)

- a first threading groove and a second threading groove for the first release thread and the second release thread, respectively, are formed in the head portion,
- at least a part of the first threading elements and the second threading elements are formed—i.e. constituted—by bridge elements bridging (i.e. composing bridges on the respective threading grooves; these can be called first and second bridge elements according to the corresponding threading groove and the reference number of these can also be fitted thereto) the first threading groove and the second threading groove, respectively (wherein the first and second release threads can be threaded by the help of the threading grooves, i.e. by the help of the threading elements formed thereon, namely the bridge elements in this embodiment).

It is noted that the threading groove with the bridge elements on it may be called threading arrangement (threading configuration); there is a threading arrangement on both side of the head portion. The threading groove may be called a main groove, thread-leading groove or simply groove. It is a groove for thread.

It is noted, furthermore, that all of the first threading elements and the second threading elements can be formed by bridge elements, but an end loop (like the loop 216) may be applied also beside the bridge elements (being in connection with the manner of handling the free ends of the released threads).

Yet further, in a more specific variant of the embodiment applying release threads as the release element, the first threading groove and the second threading groove are formed along the laryngeal opening (i.e. on the side of the head portion, where the laryngeal opening is also formed) at the respective head portion edges between the head distal end and the head proximal end of the head portion.

For the embodiments in which threading grooves with bridge elements are formed for the release threads, see e.g. FIGS. 3 and 5-7, FIG. 57, FIG. 84 and FIG. 86. In other embodiments the threading elements are formed as loops, see e.g. FIGS. 74 and 81. See FIGS. 71 and 73 where the release thread is to be inserted into one of the threading elements; these figures also illustrate that at least two first and second threading elements are arranged, respectively. Furthermore, release threads are to be passed through the bridge elements.

Some of the prior art documents mentioned in the introduction are hereby commented. We refer to U.S. Pat. No. 11,235,116 B2—application of the same applicant as the present application, corresponding to an earlier, different approach—for the relevant aspects in connection with reaching a smaller head size during the insertion.

In U.S. Pat. No. 11,235,116 B2 a single puller element is applied, by the help of which a releasable connection with which the cover element of that approach is connected to the head portion is released and the cover element is removed from the head portion. However, according to the invention, a different concept has been developed and applied, according to which separate puller portions are applied for releasing the connection of the cover element to the head portion (i.e. the release element with the first puller portion) and for removing the cover element (second puller portion).

In other words, the first and second puller portions are different from each other just like the components to which these corresponds to: the first puller portion is a part of the release element—which fixes the cover element—, and the second puller portion is a part of the cover element. In yet other words, two separate pulling tools are arranged in the laryngeal mask according to the invention.

To sum up, in U.S. Pat. No. 11,235,116 B2 the removal of the cover element is a single step removal: the cover element is removed directly. On the contrary, in the invention a two-step removal is applied, first the fixing is removed and after that the cover element with further pulling.

According to these differences between the invention and U.S. Pat. No. 11,235,116 B2, according to the invention:

- the removal of the cover element is better controllable,
- residuals remaining on the head portion or tearing off from the cover element after the removal of the cover element are avoided, and
- since there is no tearing of the cover element according to the invention, the risk and safety issues of residuals of the prior art approach are eliminated.

Moreover, it is noted in connection with WO 2015/015233 A1 that if a circumferential recess would be applied for accommodating the material of the annular cushion before inflation, excess material of the annular cushion would accumulate at the distal and proximal ends of the head portion what would make the realization of that prior art laryngeal mask very difficult or even block to realize a laryngeal mask according to that prior art concept. On the contrary, the conceptional details of the laryngeal mask according to the invention—including the preferably applied reception recess portions for accommodating the material of the annular cushion—are highly elaborated as illustrated by the various embodiments.

Figure 54:
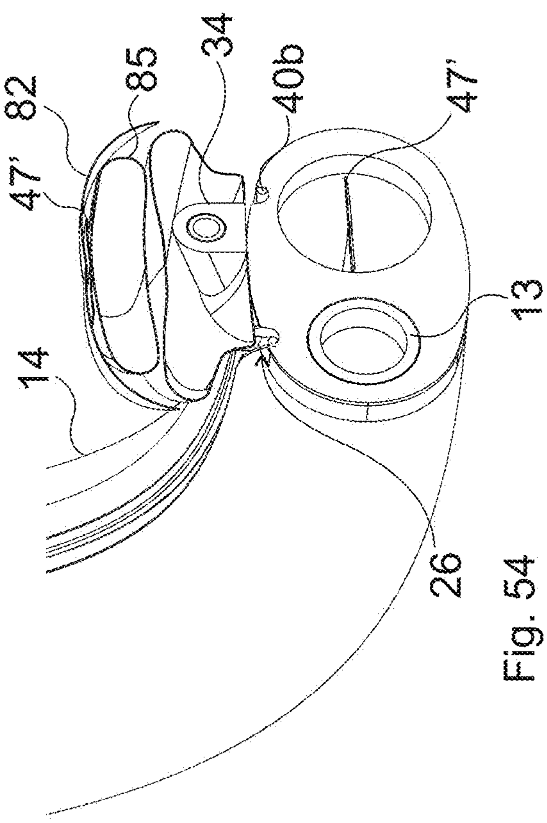
Figure 55:
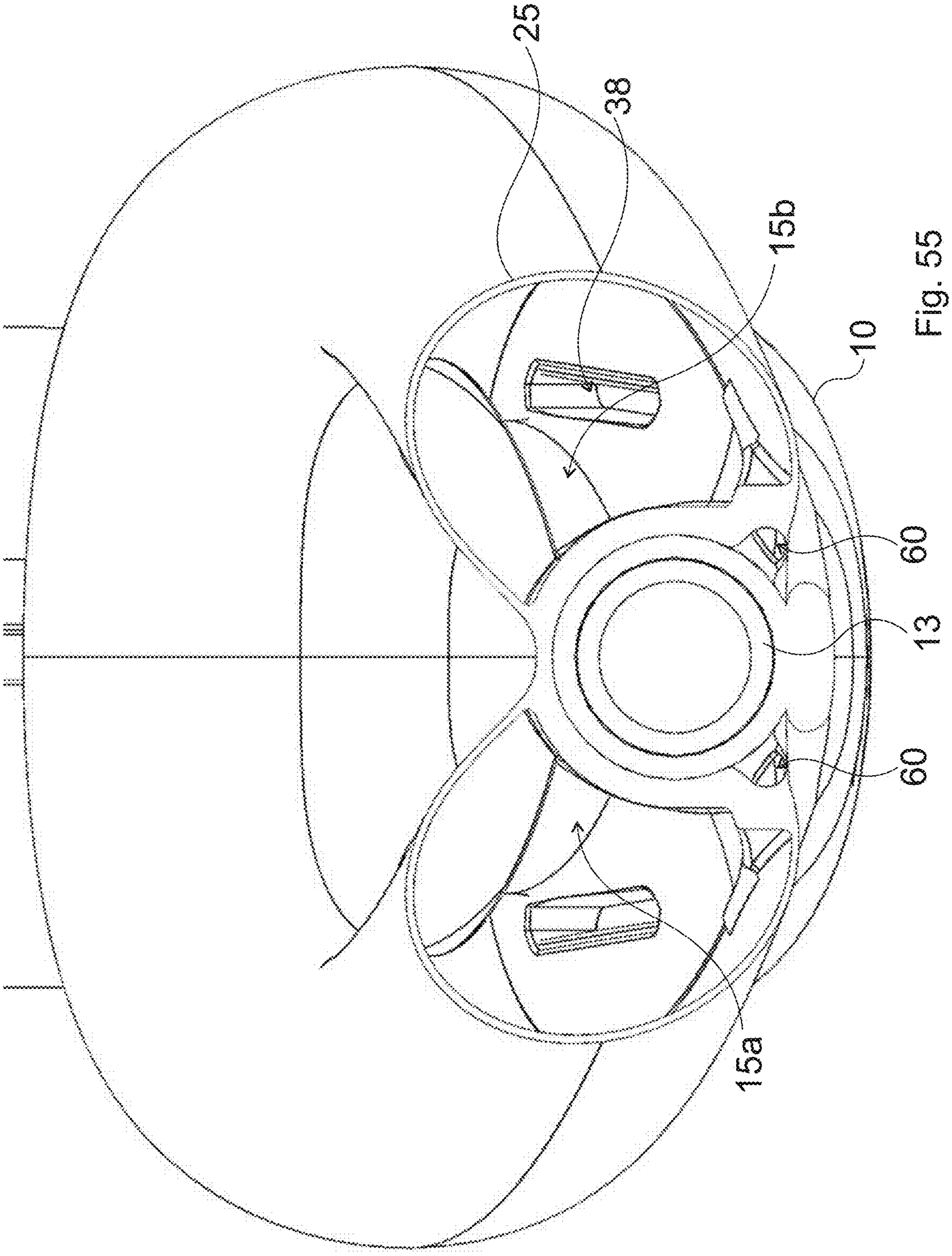
FIGS. 55 and 56 illustrate the first embodiment in different sectional views.
Figure 56:
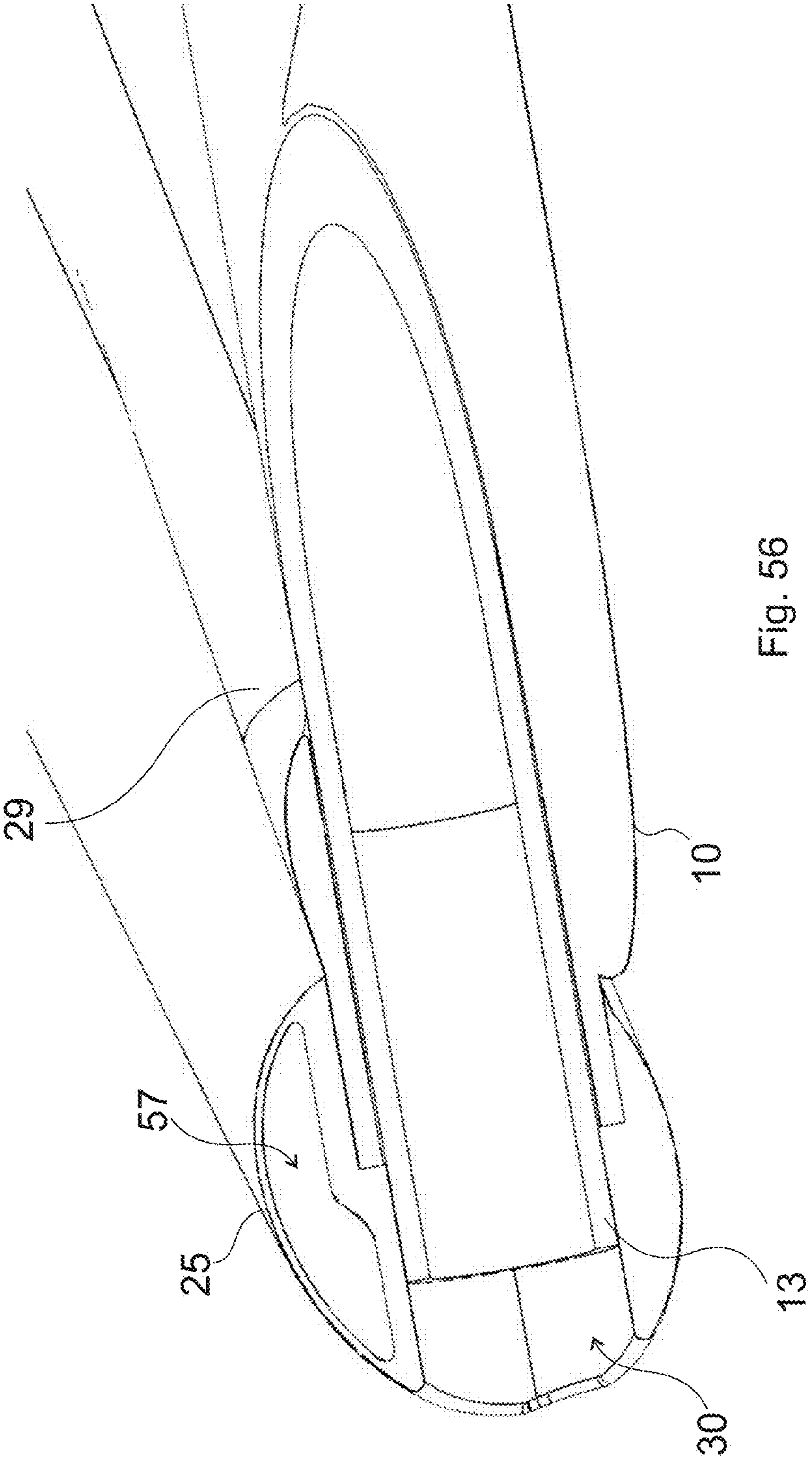

FIGS. 1-18, as well as FIGS. 19-32 (the latter are cross section figures) illustrate a first embodiment, while FIGS. 33-38, FIGS. 39-54 (these are cross section figures) and FIGS. 55-56 illustrate a second embodiment being similar to the first embodiment (these two embodiments differ in the arrangement of the annular cushion, i.e. in that it is roller or folded on their longitudinal side parts).

Accordingly, herebelow, a detailed description of the first embodiment is given with reference to FIGS. 1-32.

In FIG. 1 the first embodiment is shown in a spatial view. In this embodiment the laryngeal mask comprises a head portion 10 and a cover element 12. FIG. 1 shows the laryngeal mask in the assembled state, i.e. when an annular cushion 25 (see in FIG. 2) is packed under the cover element.

According to the view, the head portion 10 is mostly hidden by the cover element, but in comparison with FIG. 2, where the cover element 12 is removed many details can be identified.

Besides, in FIG. 1 many details of the first embodiment of the laryngeal mask are shown. In the laryngeal mask, a tube portion 14 is connected to the head portion 10 (these are preferably made integrally, i.e. forming one piece); the tube portion 14 has a bent shape as it is usual in the laryngeal masks because of the anatomy.

In FIG. 1, it is shown that a connector element 16 is arranged on a tube proximal end of the tube portion (the tube proximal end is opposite to the connection of the tube portion with the head portion, where there is the tube distal end), where also a pullable end element 19 is arranged inserted into an end tube 17. The pullable end element 19 has a grippable handle 18 facilitating that it can be pulled by hand (see also below for the details of the elements mentioned in this section). The connector element is adapter for connecting the pullable end element to the tube portion; it may also be called an intermediate element or piece, or simply end element.

In FIG. 1 it is also shown that the laryngeal mask comprises an inflation arrangement (blowing arrangement) for inflating (blowing up) the annular cushion (when it is at its destination place in the anatomy). The inflation arrangement comprises an inflation tube 20 (blowing tube; the inner space of which being in connection with the inner space of the annular cushion 25 in order to inflate, i.e. blow up the latter via the inflation arrangement) with a valve 21 arranged on the end of the inflation tube 20 being opposite to the head portion 10. The valve 21 is connectable to the connector element 16 which will be shown in more details later (see the description of FIGS. 14-16B).

FIG. 2 shows the first embodiment of the laryngeal mask in a similar view as FIG. 1, but in FIG. 2, the cover element 12 is removed. Consequently, an annular cushion 25 is become visible in FIG. 2. It is noted in connection with the annular cushion 25, that it is shown in an uninflated (unblown) state, just like it was under the cover element 12 in order to illustrate its arrangement under the cover element. By the removal of the cover element 12, naturally, the annular cushion 25 would become loose, at least to some extent, but this loosening is not illustrated in FIG. 2.

As a further detail, a gastric hole 30 corresponding to gastric tube (for this, see other figures, wherein a gastric tube 13 is shown) is observable in FIGS. 1-2. Furthermore, in FIG. 2 a threading groove become visible by the removal of the cover element 12, slightly covered by the cushion element 25, this will also be described later.

Figure 4:
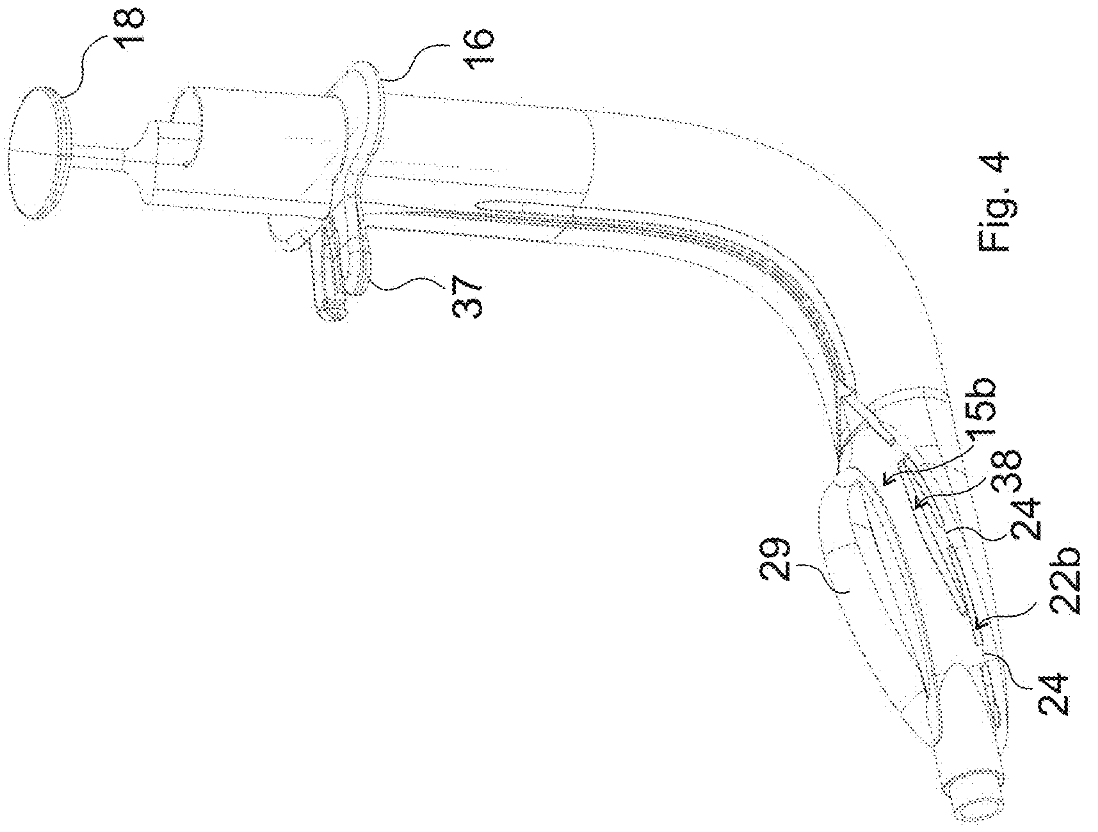
FIGS. 3 and 4 show the first embodiment of FIG. 1 also without the annular cushion from two different spatial views.

In FIGS. 3 and 4, the first embodiment of the invention shown with removing also the annular cushion 25 and the inflation tube 20 with the valve 21. These removals facilitate to see more details of the configuration of the head portion 10, which is also helped by the different view shown in FIG. 3.

In FIG. 3 the details of the head portion 10 are the followings. FIG. 3 shows a first threading groove 22*a* at an edge of the head portion 10 and it is observable that a further, second threading groove 22*b* is formed on the other side of a laryngeal opening 28. The other threading groove 22*b* is moreover observable in FIG. 4 showing the laryngeal mask from another view in the same state (i.e. without the annular cushion 25; in FIG. 9B it is shown that the first threading groove 22*a* and the second threading groove 22*b* can be denoted commonly as threading grooves 22, which are formed deepened into the head portion 10).

FIGS. 3 and 4 also show that there are bridge elements 24 bridging the threading grooves 22, i.e. there are small "bridges" on the threading grooves 22 (which is a recess in the head portion, i.e. the bottom of the threading grooves 22 is at a different height—in the view of figure: lower—than the surface around the threading grooves 22 of the head portion 10) connecting the two "banks" of it. It can be also observed in FIG. 3 that after the last—i.e. the one being farthest from the head distal end 11*a*—respective bridge elements 24, the threading groove 22*a* continues in a further threading groove piece 26, and in FIG. 3 another threading groove piece 26 ending in the threading groove 22*b* of the other edge of the head portion 10 is also observable. Furthermore, these threading groove pieces 26 start from the threading grooves 22 and end in a thread channel 32 leading to the end of the tube portion opposite to the connection of the tube portion with the head portion 10. It is noted that the threading groove pieces might be covered channels, i.e. for example tunnel like channels which are not opened ditches as the threading groove pieces 26.

Figure 5:
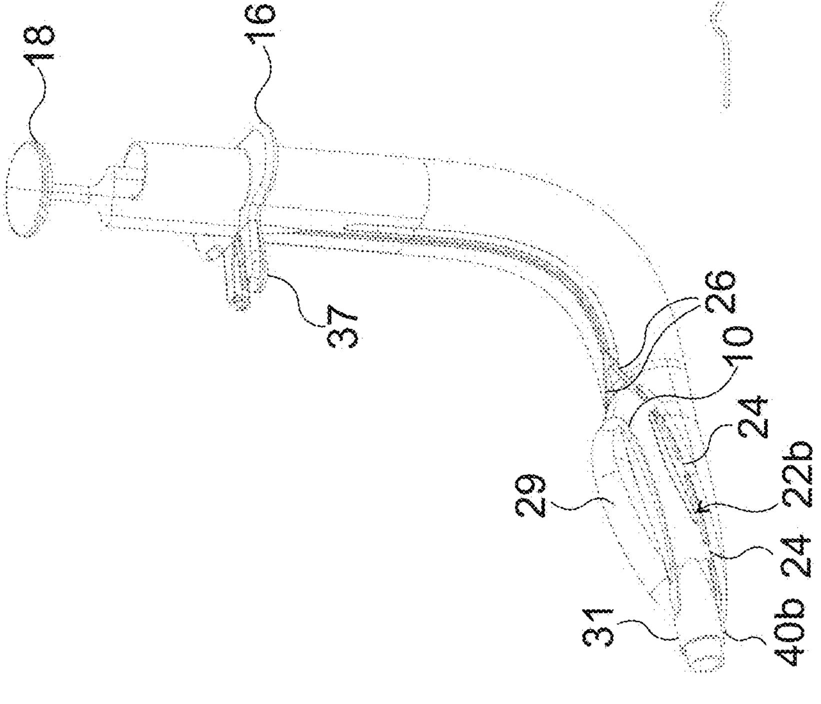
FIG. 5 shows the first embodiment of FIG. 1 without the annular cushion, but also showing release threads.
Figure 6:
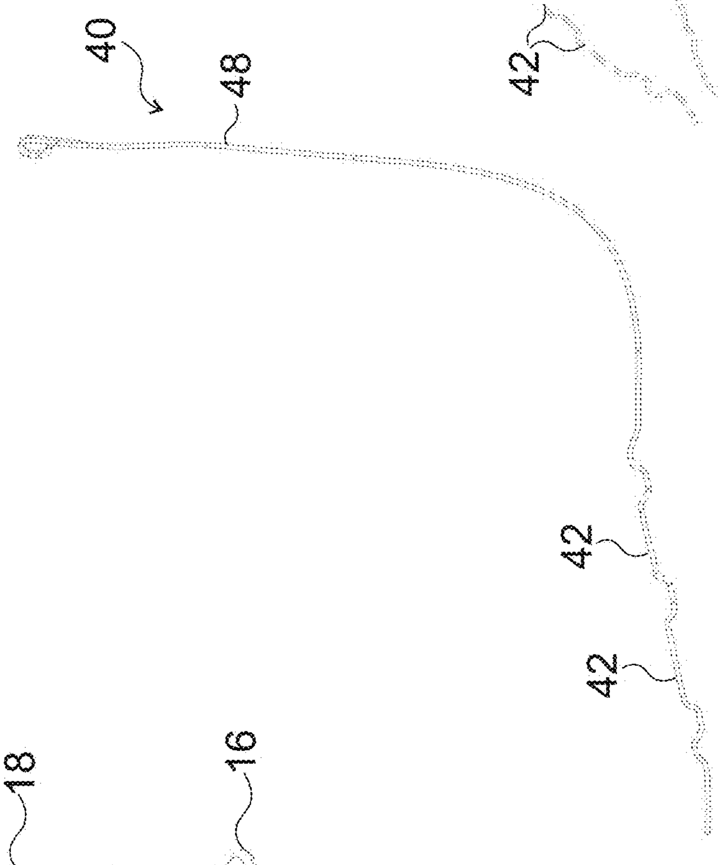
FIGS. 6 and 7 illustrate release threads for the first embodiment.

It is noted hereby that the threading grooves 22, the threading groove pieces 26 and the thread channel 32 are formed for accommodating first and second release threads 40*a*, 40*b* observable e.g. in FIGS. 5-7 (via these structural parts the released threads 40*a*, 40*b* are routed to the outer end of the tube portion 14 in order to facilitate their removal). It is observable in FIG. 3 that the threading grooves 22 extend until a distal tip 31, i.e. where a tube end of a gastric tube 13 is situated (the gastric tube 13 is a little bit longer than the distal tip 31). The end of the release threads 40*a*, 40*b* will be arranged here in the state where those fixing the cover element 12 to the head portion 10.

The laryngeal opening 28 and its collar 29 arranged around it can be clearly observable from FIG. 3 (cf. FIG. 2, where the annular cushion 25 is shown as arranged around the collar 29). The collar 29—which is annular, i.e. arranged around the laryngeal opening—helps to have reception recesses on the two sides of the laryngeal opening 28 (in FIG. 3 a first reception recess 15*a* is shown, for a second reception recess 15*b* of the other side of the head element 10, see FIG. 4). There is also a connection groove 38 between the threading groove 22*a* and the collar 29 (i.e. the threading groove 22*a* and the connection groove 38 run beside each other, the threading groove 22*a* is bent a little; see the connection groove 38 of the other side in FIG. 4). For more structural details, see the description of FIG. 12.

It is noted that the collar around the laryngeal opening constitute a flange of the reception recess (it can be considered also as a flange of the laryngeal opening), according to the configuration in an embodiment in which a reception recess is formed in the material of the head portion. The collar has a varying configuration around the laryngeal opening in connection with which we refer to the figures. In some cases, the collar is minimal or substantially does not extend outwards at the head proximal end (see e.g. FIG. 86). At the head distal end, the collar extends above the distal tip (e.g. in the first embodiment, but see also FIG. 82 for a respective collar configuration).

The followings are noted in connection with a non-limiting example.

Above, non-limiting example has been also given for the material of the cover element. Furthermore, also in a non-limiting example,

- the head portion and the tube portion are made of an appropriate silicone material, preferably these two are made integrally,
- the annular cushion is made of—an e.g. thinner—silicone material (i.e. from the two, head portion is made from a thicker material).

In a non-limiting example, for the release thread a medical grade material—e.g. plastic—is applied (in a non-limiting example: polyamide, e.g. nylon; other non-limiting examples: polypropylene, polyester, silk; it is only threaded onto the head portion, not connected, so no particularly strong material is needed).

Preferably, medical grade materials are utilized for the laryngeal mask.

Furthermore, it is noted, that the size of the laryngeal mask has a relation with the body size to be appropriate for the trachea. Accordingly, different size laryngeal mask is applied for a child and an adult, but the configuration and the features are the same irrespective of the size.

In FIG. 3, some more details of the connector element 16 are also shown, since the inflation tube 20 and the valve 21 have been remove from the figure. Hence, a pullable end element 19 with a handle 18 is shown inserted onto an end tube 17 extending out from the end of the tube portion 14 (for the insertion of the pullable end element 19 onto the end tube 17, see FIGS. 16A-16B and consider also FIGS. 17A-18 for the central cutout 189 for insertion).

A similar state of the first embodiment as of FIG. 3 is shown in FIG. 4 in a different view.

In the figures that of, e.g. in FIG. 3, it is illustrated that in the first embodiment, between the head end of the thread channel and the head portion the first release thread and the second release thread are arranged in respective interconnection threading groove pieces (see the threading groove pieces 26 in the figures), wherein at the head end of the thread channel being at the head portion the interconnection threading groove pieces

- have a junction (these meet with each other at the thread channel), and
- close a thread angle between 10° and 100° (accordingly the thread angle is required at the junction; the interconnection threading groove pieces are not necessarily straight, but, preferably, the interconnection threading groove pieces are straight).

Figure 57:
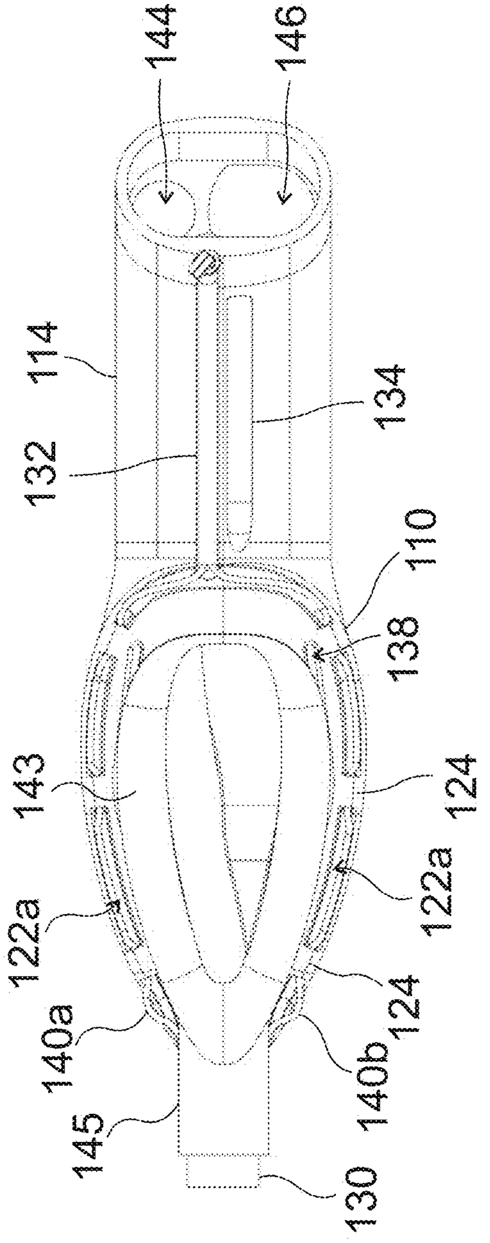
FIG. 57 shows a third embodiment of the invention without annular cushion from an upper view.

The thread angle is preferably between 10° and 100°, more preferably, between 40° and 100°, i.e. it can be varied between wide boundaries to have the effect that a lower pulling force is needed than e.g. in the case of the third embodiment (corresponding to the angle of 180°, see e.g. FIG. 57; the friction is smaller along the threading groove parts between the released threads and the wall of the threading groove parts; it is preferred if the pulling force is lowered, a high pulling force may cause complications, even displacement of the laryngeal mask). It is noted that in the figures illustrating the first embodiment, a thread angle of approx. 75° is shown, thus, it is in the preferred region.

Furthermore, these are preferred angles from the point of view that the necessary pulling force is relatively high above an angle of 100°. The other boundary of the region is in correspondence with the following. If the angle is too small, then the junction of the threading groove pieces (see the threading groove pieces 26 in the figures) will be too far from the head. This is why the region of 40-100° is given as especially preferred.

In FIGS. 5-7 the arrangement of release threads 40, namely a first and a second release threads 40*a*, 40*b* are illustrated. In. FIG. 5, thus only a release thread 40*b* is visible (cf. FIG. 7), see its end at the distal tip 31. Bends of the release thread 40*b* are also visible in FIG. 5, since release thread 40*b* is shown in FIG. 5, as if the cover element 12 would be arranged and it would be fixed to the head portion 10 by the help of the release threads 40.

FIGS. 6 and 7 show the release threads 40 but in FIG. 6 in such a view in which only one release thread is visible from a side view, the other is hidden behind this. Also bends 42 are shown in FIG. 6, just like in FIG. 7 which illustrates both release threads 40*a*, 40*b* in a configuration as these are arranged within the cover element 12 when fixing the cover element 12 to the head portion 10. It is noted that the release threads 40*a*, 40*b* run together in their part where they have left the head portion, i.e. after joining of these in the at the meeting ends of threading groove pieces 26 (cf. FIGS. 5 and 7) this together running part can be considered to be the first puller portion 48.

Based on FIG. 7 a further possibility is conceivable for the configuration: a Y-shaped component (which is manufactured with this shape) having the release threads as two free ends and have a common first puller portion. The end of the common first puller portion to be arranged at the tube proximal end of the tube portion may have a loop for fixing it into the pullable end element.

Figure 8A:
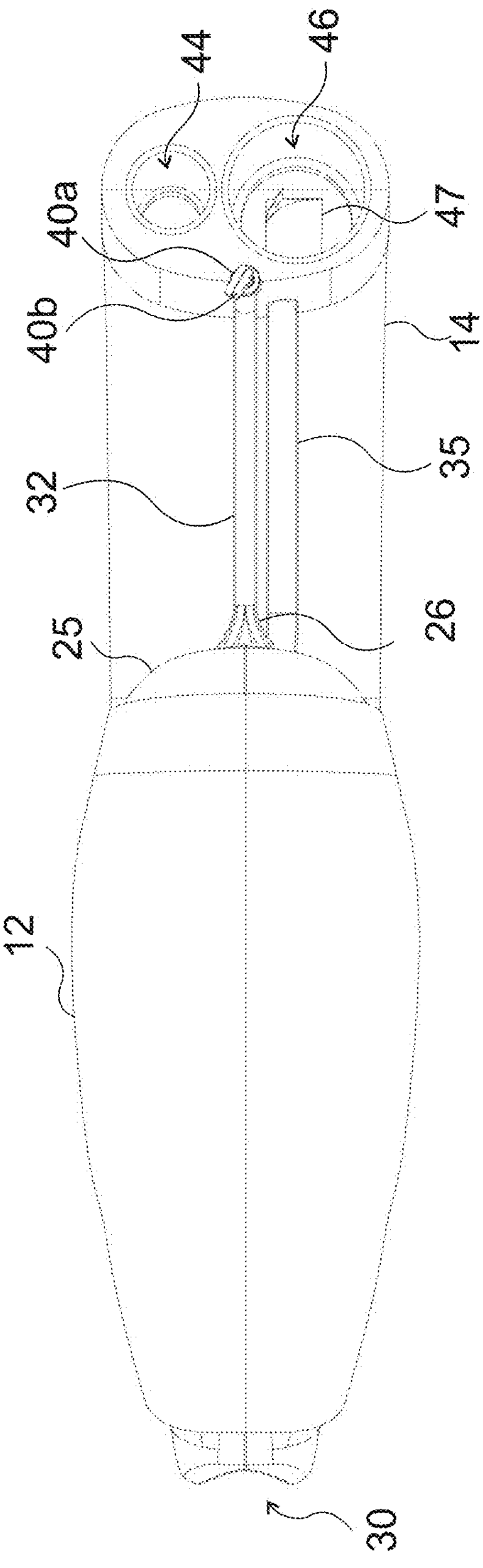
FIGS. 8A-8B show the first embodiment of FIG. 1 from an upper view with and without the cover ring element.
Figure 8B:
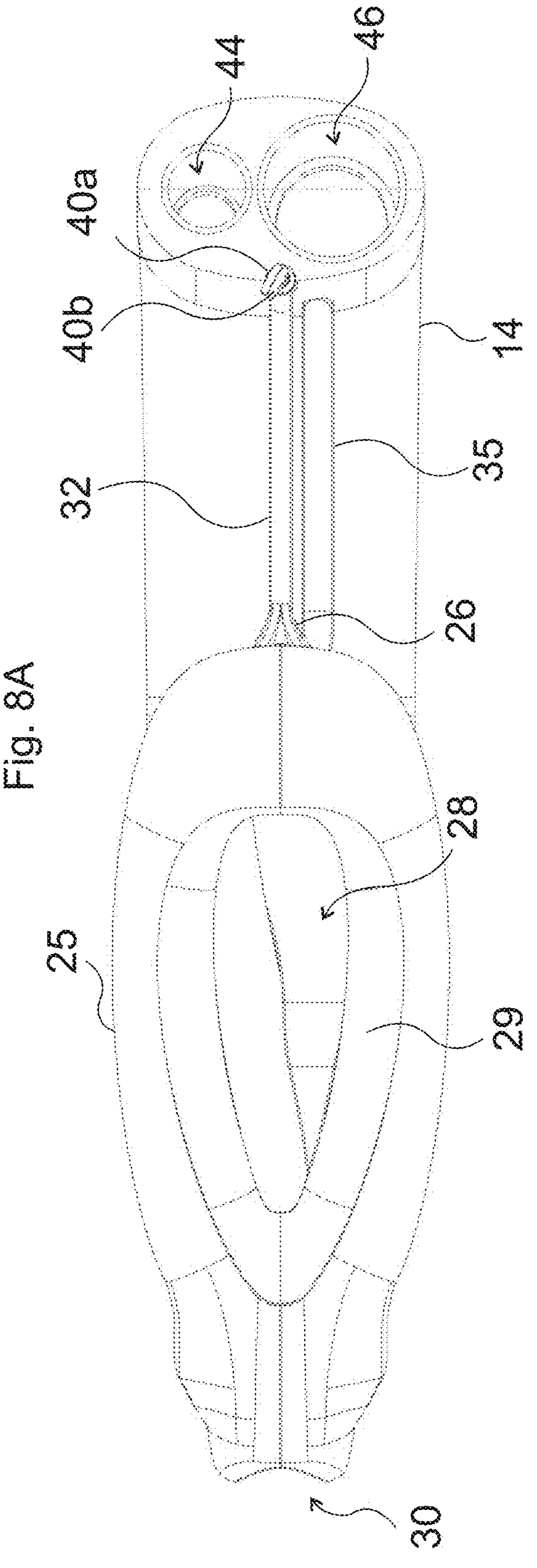

FIGS. 8A and 8B show the first embodiment of the laryngeal mask from an upper view, with and without the cover element 12, respectively (see the gastric hole 30 denoted). Comparing to FIG. 8B, it can be observable in FIG. 8A which parts of the annular cushion 25 are covered by the cover element 12 and which are not covered (some part at the head distal end and some at the head proximal end of the head portion 10 are not covered).

Since the connector element 16 is removed in FIGS. 8A-8B, the end of the release threads 40*a*, 40*b* can be seen at the opened end of the tube portion 14 extending out from the thread channel 32 (there are shown the ends of two release threads 40*a*, 40*b*). Running of the release threads 40*a* and 40*b* can be observed also in the threading groove pieces 26, the junction of which can be seen in FIGS. 8A-8B. Along the thread channel 32, an inflation tube groove 35 for the inflation tube 20 is formed (cf. FIG. 1 where the inflation tube 20 is arranged).

In FIGS. 8A-8B at the opened end of the tube portion 14 (it is opened because of removal of the connector element for illustrative reasons), ends of a first and a second inner channels 44 and 46 are shown (a channel for the gastric and a so-called airway channel, respectively). The first inner channel 44 corresponds to the gastric tube 13 (i.e. continues the gastric tube 13 in the tube portion 14), while the second inner channel 46 is that in which a puller portion 47 of the cover element 12 is arranged (see FIG. 8A and cf. FIG. 12, wherein the puller portion 47 is folded at a portion thereof).

FIG. 8B shows the annular cushion in an uninflated state i.e. in the state in which it is arranged as covered by the cover element 12, in this view the cover element 12 has just simply removed vis-à-vis FIG. 8A. In FIG. 8B—by the removal of the cover element 12—the puller portion 47 is not shown in the channel 46 (it is not there).

Figure 9B:
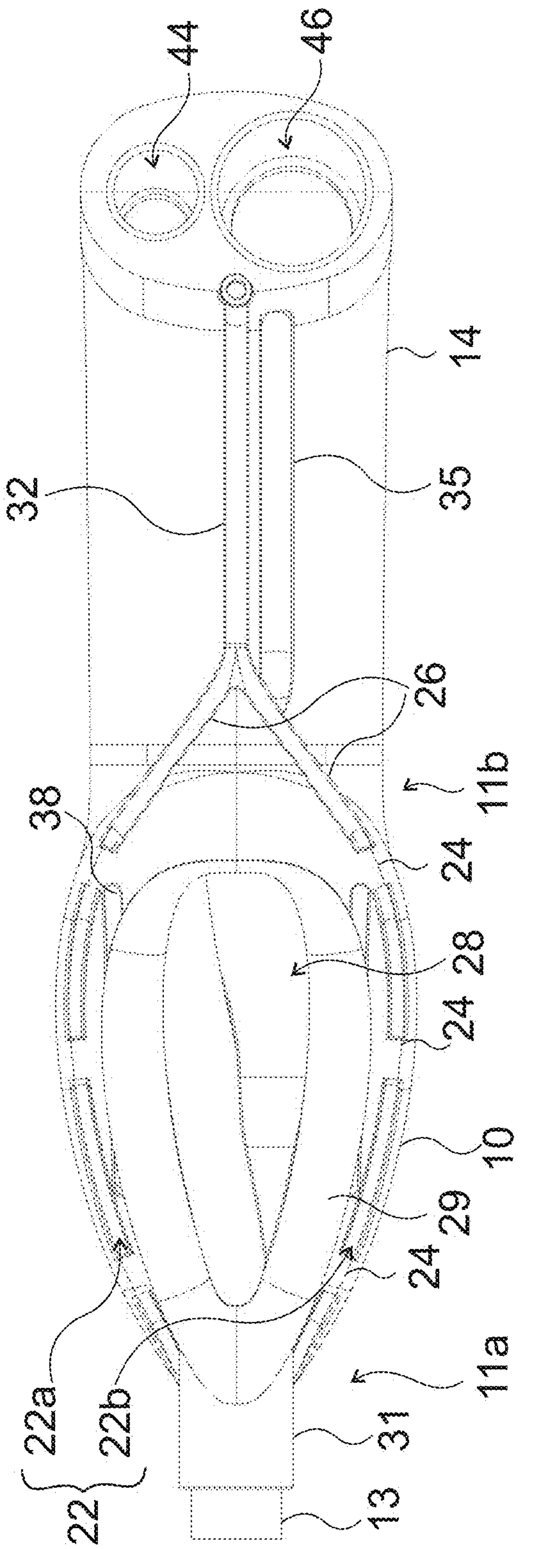

FIGS. 9A and 9B show upper views, similarly to FIGS. 8A and 8B, but with the removal of not only the cover element 12, but also the annular cushion 25. Furthermore, the release threads 40*a*, 40*b* are arranged in FIG. 9A, but these are also removed in FIG. 9B. Similar to FIG. 5, FIG. 9A also shows the release threads 40*a*, 40*b* in a state as if the cover element 12 would be arranged for the sake of illustration (i.e. with bends). It can be understood from this view, that at the bridge elements 24 the release threads 40*a*, 40*b* run in their respective threading grooves 22*a*, 22*b*, but between these are inserted under the cover element 12, i.e. to secure it to the head portion 10 by the help of bridge elements 24 which give the anchoring. To illustrate how the cover element 12 is secured to the head portion 10 by the help of the release threads 40*a*, 40*b*, see FIGS. 19-32 for the first embodiment.

In FIG. 9B, wherein also the release threads 40*a*, 40*b* are removed, the threading grooves 22*a*, 22*b*—commonly threading grooves 22—can be seen from above along the edges of the head portion 10, having three-three bridge elements 24 per side. Also, the empty thread channel 32 can be observed in FIG. 9B. End of the thread channel 32 at the head portion 10, as well as the threading groove pieces 26 are clearly observable in this view.

Figure 10:
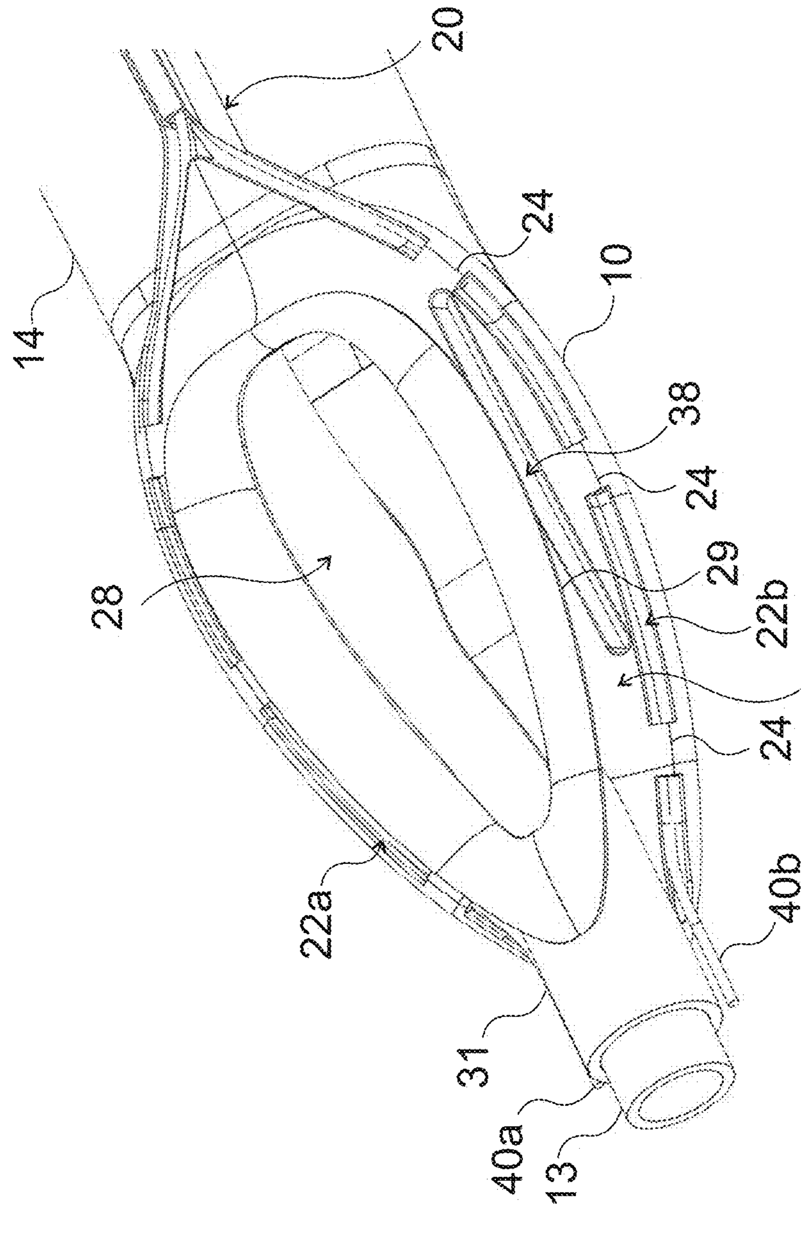
FIG. 10 shows the first embodiment of FIG. 1 in a spatial view, without the annular cushion and with release threads.

In FIG. 10 the head portion is illustrated in a similar state as in FIG. 9A, but in a different view. In this view some details are better observable. The release threads 40*a*, 40*b* are arranged in FIG. 10, and the end of released thread 40*b* is clearly observable near the distal tip 10. In this view the release threads 40*a*, 40*b* are not arranged in a way as if the cover element 12 would be arranged but the release threads 40*a*, 40*b* are arranged in the threading grooves. Also, the laryngeal opening 28, its collar 29 can be observed well, as well as the reception recess 15*b* of this side. In the reception recess 15*b*, the connection groove 38 is clearly observable, as well as the configuration of the part of the gastric tube 13 which is observable through the laryngeal opening 28.

Figure 11B:
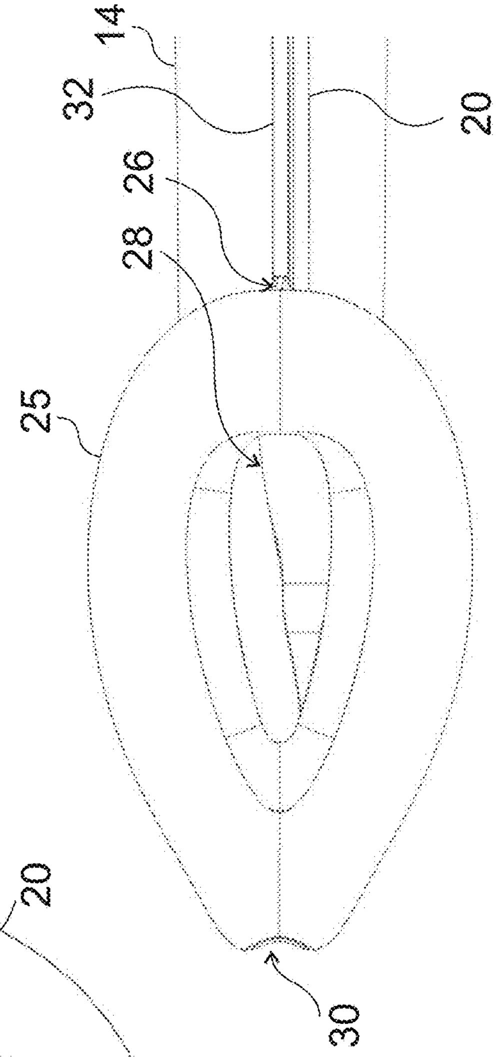
FIGS. 11A-11C show the first embodiment of the laryngeal mask in an inflated state.
Figure 11A:
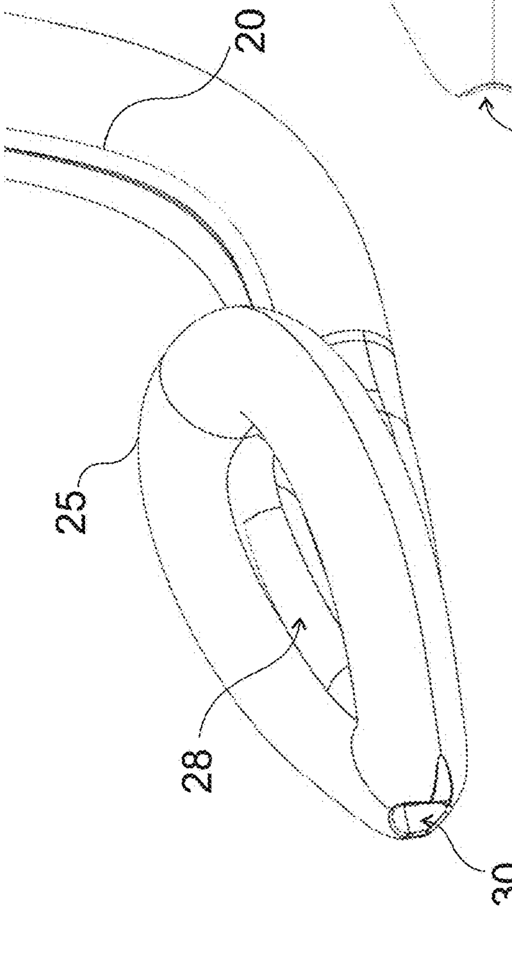
Figure 11C:
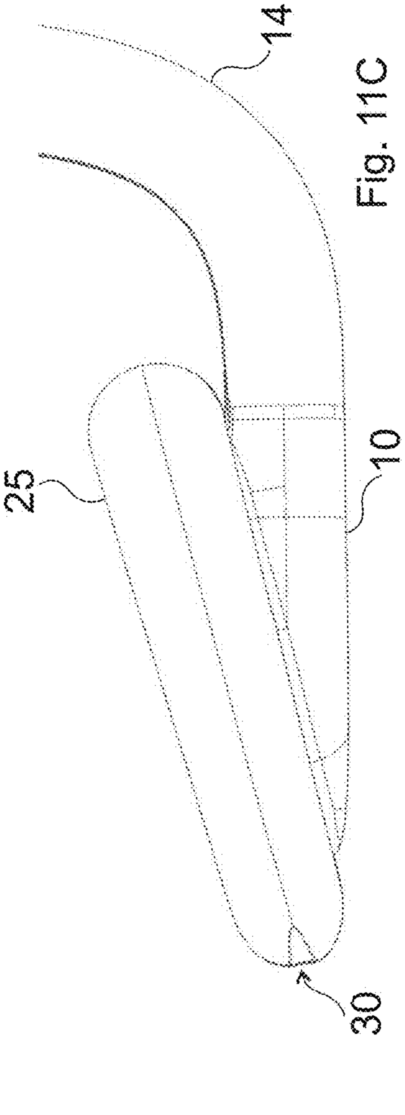

In FIGS. 11A-11C the inflated state of the annular cushion 25 in the first embodiment is shown in different views. FIG. 11A shows a usual (i.e. applied in another figures) spatial view, where the annular cushion 25 is inflated. Furthermore, FIG. 11B shows an upper view, as well as FIG. 11C shows a side view (see the gastric hole 30 denoted in FIGS. 11A-11C).

Figure 12:
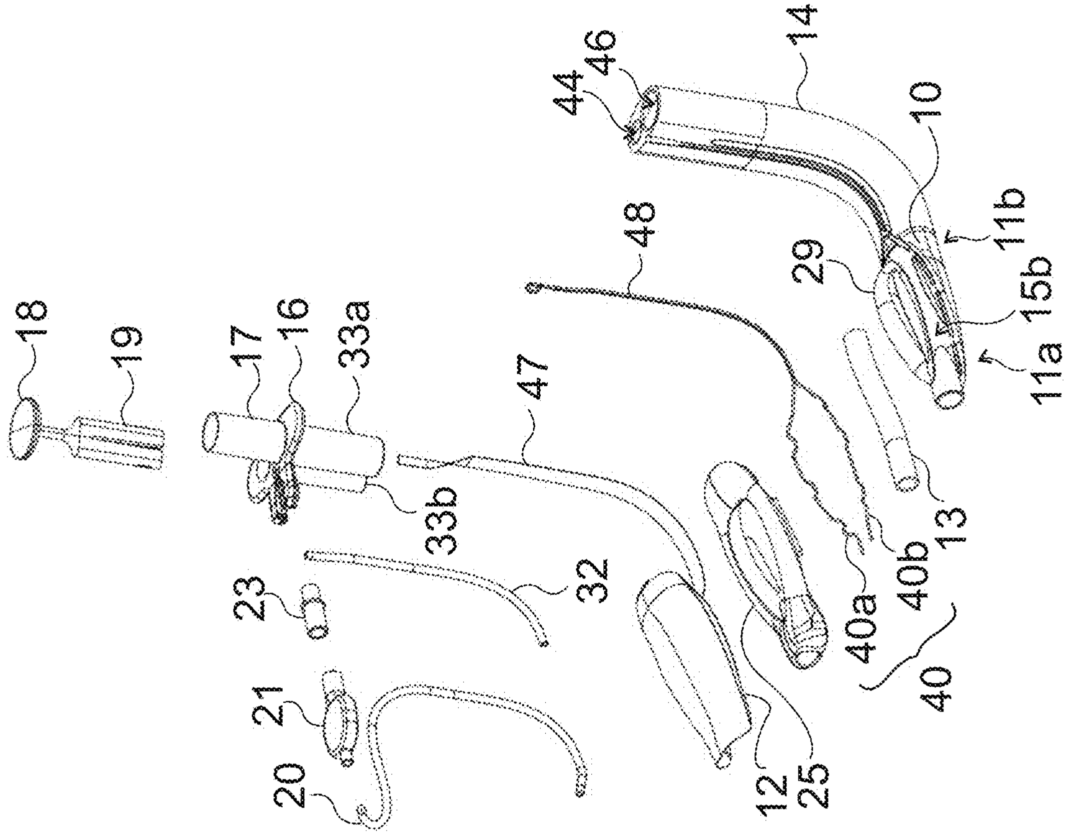
FIG. 12 shows the first embodiment of the invention in an exploded view of the elements.

FIG. 12 shows an exploded view of the first embodiment of the laryngeal mask. In this view, every component is illustrated in a state (arrangement, details of forming those) as if these would be built together, but shifted to be side by side. Accordingly based on the exploded view, it can be understood how the various components are inserted and/or connected to each other.

At the right side of the figure, we can see the head portion 10 and the tube portion 14 with inner channels 44, 46. The next component near the basic parts of the laryngeal mask (i.e. head portion 10 and tube portion 14), the gastric tube 13 is arranged (being a separate, insertable component in this embodiment). The gastric tube 13 is inserted into the inner space of the head portion 10 as illustrated in other figures, e.g. FIG. 3.

It is noted that the head parts in the different embodiments, preferably

- are configured in such a way that the gastric tube can be inserted from the front, i.e. through the distal tip, and
- have such inner configuration which helps with leading the gastric tube to be inserted into its desired final place).

The next component in the exploded view of FIG. 12 is the pair of release threads 40 (see also the first puller portion 48 thereon), which is arranged as if being in an assembled state in the head portion and the tube portion, as illustrated in the above referenced figures.

The yet next component is the annular cushion 25, in its uninflated state. The annular cushion 25 has been illustrated above as connected to the head portion, but in this view, it is shown separately (for the connection of the annular cushion 25 cf. FIGS. 12 and 36 with FIGS. 37-38). It is noted about the annular cushion 25 that it is its uninflated state which means as if it would be covered by the cover element 12.

In accordance with this, the next component in the row is the cover element 12. According to the exploded view also the puller portion 47 of the cover element 12 is shown. Compared to the other components, it can be observed that the cover element 12 and the puller portion 47 are arranged in FIG. 12 as if these would be in the assembled state.

Above the puller portion 47 of the cover element 12, the connector element 16 can be observed in FIG. 12. It can be observed that the connector element 16 has a first tube piece 33*a* and a second tube piece 33*b*, which are to be inserted to the inner channels 44, 46 of the tube portion 14, respectively, to connect the connector element 16 to the tube portion 14. It can be also observed that the connector element 16 also has the end tube 17 to which the pullable end element 19 is to be connected (via a cutout extending longitudinally from the bottom of the pullable end element 19, see FIGS. 17A-18).

Going to the left in the figure, a thread channel 32 can be seen (cf. FIG. 8A-9B). The further components to the left are the parts of the inflation arrangement, i.e. the inflation tube 20, valve 21 and the connection member 23.

In FIG. 13 the cover element 12 is shown as it is laid out. In this view a first row of threading holes 52*a* and a second row of threading holes 52*b* (in other words, fixing holes or connection holes; may be called first and second-threading-holes, respectively, i.e. these may also be called simply holes) can be observed at both of the edges of the cover element 12. Furthermore, the puller portion 47 connected to the cover element 12 (the latter may also be considered as the main part of the cover element, but simply: there is the cover element which is provided with a puller portion) can be observed.

Referring to FIG. 13 and also to FIG. 77, it is hereby noted that generally the shape of the (main part of) the cover element is determined by the needs posed for it, requirements in connection with it, i.e. the details of its shape (its outline, or, sizing in case for a given head portion size) can be determined based on the configuration of the head portion. The main requirement is to have the (threading) holes at appropriate places when the annular cushion is encompassed by it, preferably tightly (in a way illustrated by the figures).

In the above part of the description the structure and the arrangement have been given for the elements of the first embodiment of the invention. Herebelow, it will be detailed what initialization (uncovering) steps are to be performed on the laryngeal mask for facilitating its intended medical use—i.e. the use of the laryngeal mask in the anatomy—at its destination place on the trachea (to allow the intended medical use, the cover element is to be removed as the result of the initialization steps). This description of the initialization steps (i.e. making it ready to use) is applicable for all embodiments of the invention.

In the following description we refer mainly to FIGS. 1 and 12, but other figures will be referred also, as well as the description of FIGS. 14-18 will be given herebelow. When the laryngeal mask is inserted to its destination place in the anatomy, it is in the state illustrated in FIG. 1, until reaching the final destination place on the trachea. When the laryngeal mask reached its destination place, the following initialization steps are to be performed so as to facilitate the medical use of the laryngeal mask (summarized in broad terms):

removing of the release element (e.g.: release threads);
removing of the cover element; and
inflating the annular cushion.

The above steps will be detailed in the following for the first embodiment of the invention (generalizable also to the other embodiments). It is noted here that the joint pulling of the cover element and the release element has been touched upon above, but herebelow we will also give some options and details. As understandable from FIGS. 1-12, the cover element 12 is fixed to the head portion 10 by means of release threads 40*a*, 40*b* (applied as release element).

Accordingly, when the laryngeal mask illustrated in FIG. 1 reaches the destination place, the release threads 40*a*, 40*b* hold the cover element 12 in its place on the head portion 10 of the laryngeal mask. It can be understood from FIGS. 1 and 12 and other figures that if the release threads 40*a*, 40*b* are removed by the help of pulling them at the end of the tube portion, then the connection between the cover element 12 and the head portion 10 is terminated, since the release threads 40*a*, 40*b* do not connect these to each other anymore.

This makes it possible to remove also the cover element 12. As it is illustrated in FIG. 12 and in other figures, the cover element is arranged on the laryngeal mask in its destination place so as that its puller portion 47 runs in the inner space of the tube portion (preferably, namely in the channel 46 as illustrated e.g. in FIG. 8A). Accordingly, after the removal of the release threads 40*a*, 40*b* the cover element 12 is also removed from the laryngeal mask (according to the joint pulling), and thus the annular cushion 25 becomes free.

The free state of the annular cushion 25 facilitates that it can be inflated in its destination place. Thus, in this status the annular cushion 25 is inflated by the help of inflation arrangement illustrated in FIG. 12 having the parts of an inflation tube 20, a valve 21, and in the illustrated embodiment a connection member 23 (see also FIGS. 16A-16B).

Figure 14:
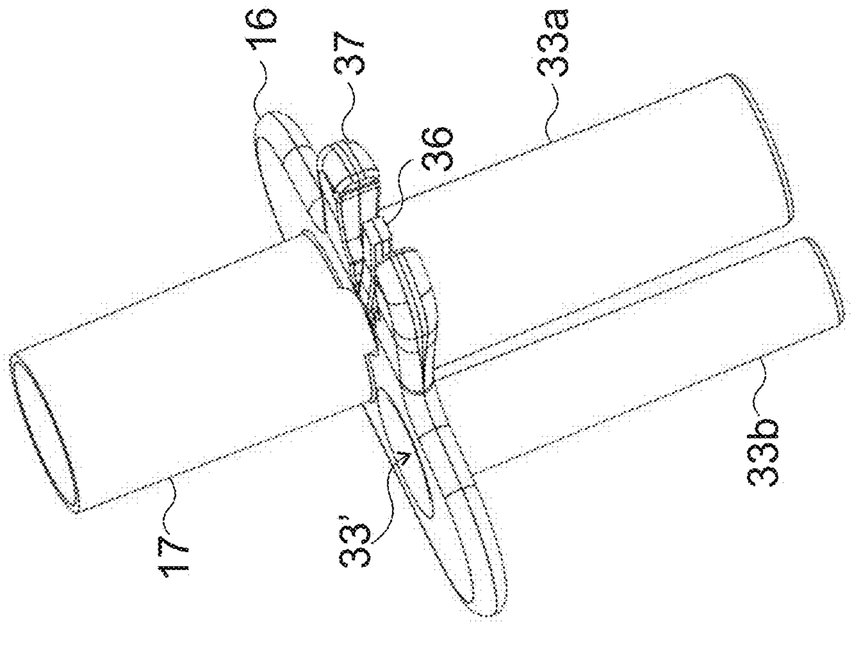

In FIG. 14 the connector element 16 is shown in a view being different from FIG. 12, where it is also shown. The details of connector element 16 can thus be observed, namely that the tube piece 33*b* of the connector element 16 ends in a hole 33' (opened to the channel into which the gastric tube is connected on its other end at the head portion) in the main flat part of the connector element 16 and that the tube piece 33*a* continues in the end tube 17.

Figure 15:
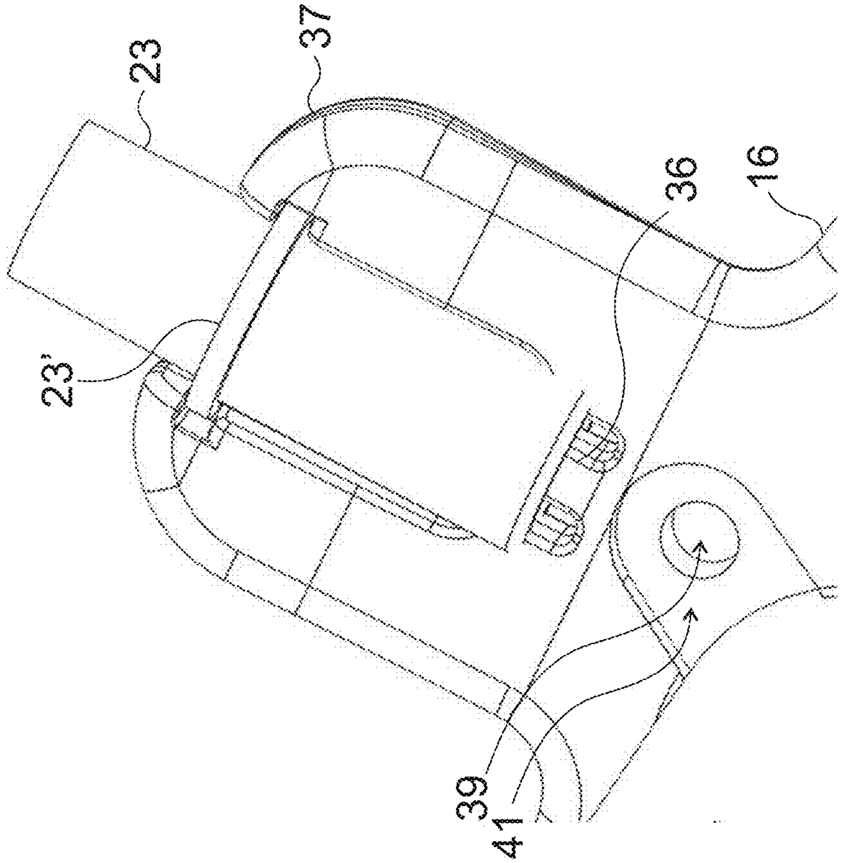
FIGS. 14 and 15 show details of a connector element insertable into the tube portion.

Furthermore, it is shown in FIG. 15 that the connection member 23 is connected to the connector element 16 by means of its rim 23'. The connection member 23 is pushed onto a connection pin 36 of the connector element 16 and the rim 23' is inserted onto an accommodating element 37 having the connection pin 36 in a U-shaped accommodating space thereof (can be interpreted in comparison with FIG. 14).

In FIG. 15, a further detail is noted: a release thread hole 39 is shown at the base portion of the connection pin 36 in a connection indentation 41 being lowered into the connector element 16. The release thread hole 39 is formed to let through the release threads 40 (cf. FIG. 70 where the connector element 116 is utilized similar to connector element 16), i.e. the release thread hole 39 is arranged in the assembled state of the laryngeal mask at the end of the thread channel 32.

Figure 16B:
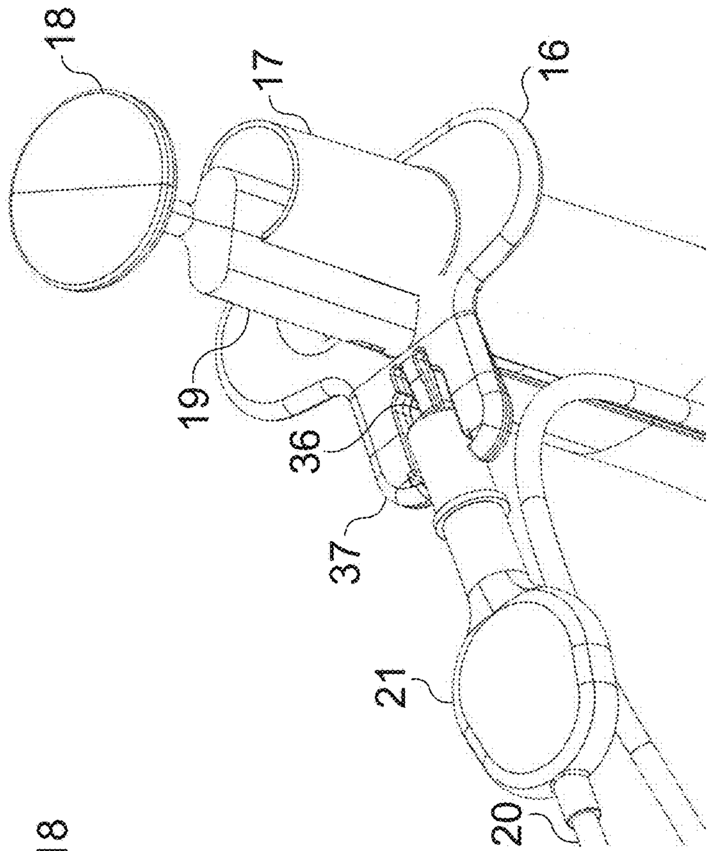
FIGS. 16A and 16B show the connector element and the tube portion for illustrating the operation of the inflation arrangement.
Figure 16A:
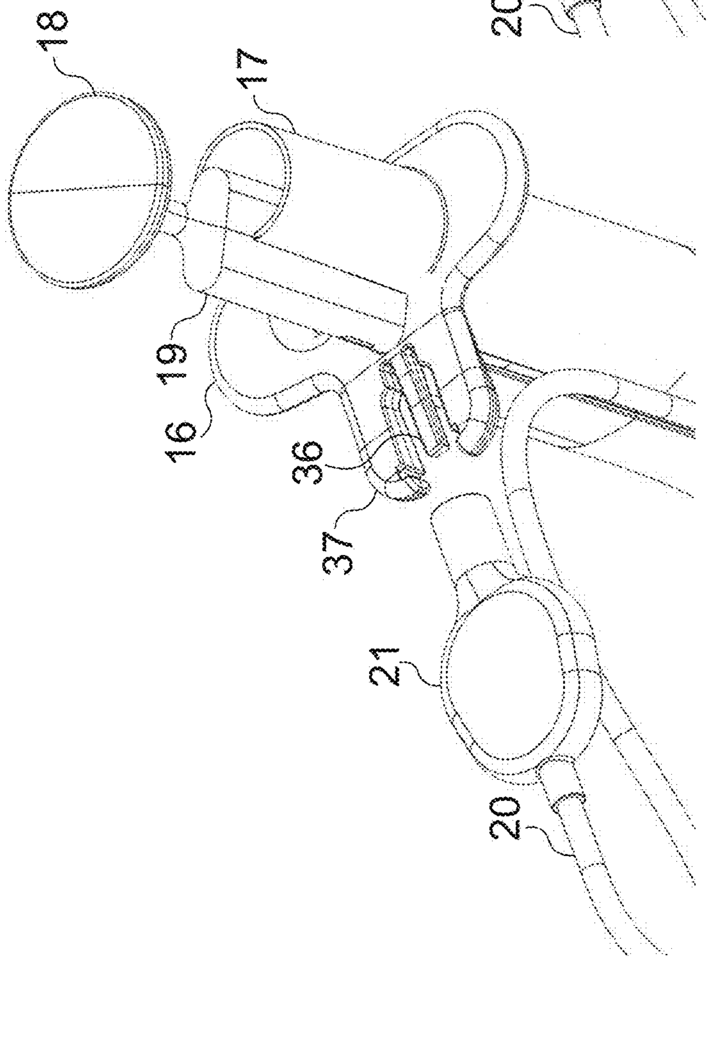

The role of the connection indentation 41 can be interpreted based on FIGS. 16A-16B, in which the pullable end element 19 is inserted to its place, namely into the connection indentation 41.

FIGS. 16A and 16B illustrate how the inflation arrangement can be connected to and disconnected from the connector element 16. Thus, the inflation arrangement can be used for inflation when it is detached from the connector element 16 and when an (external) inflation apparatus is connected to the valve 21, since this part of the inner tube is arranged outside the patient and the laryngeal mask is inserted into its destination place. The inflation can be performed from outside and the final state of inflation of the annular cushion 25 illustrated in FIGS. 11A-C can be reached.

According to the above, in an embodiment, the laryngeal mask comprising

- a connector element inserted onto the tube proximal end of the tube portion, having a connection pin (see the connector element 16 with the connection pin 36 in FIGS. 14-16B; other type connector element is also conceivable with a connection pin), and
- an inflation arrangement for inflating the annular cushion, wherein the inflation arrangement comprises
  - an inflation tube being in connection with an inner space of the annular cushion, and
  - a valve arranged on the end of the inflation tube being opposite to the head portion, connectable onto the connection pin for maintaining an open state of the valve (see the inflation tube 20 and the valve 21 in FIGS. 16A-16B).

It is thus hereby noted that the valve does not have role only in inflating the annular cushion (it is noted that the inflation is also done via this valve), but it has a role of maintaining the open state of the valve when the valve is connected onto the connection pin. This means that the inner space of the annular cushion is not closed, namely it is open through the inflation arrangement. As a consequence, pressure variations (e.g. during a sterilization, during the transport of the device in a plane, or because of diffusion through the material of the annular cushion) does not affect the annular cushion; these can be equilibrated. Without this if the pressure would increase in the annular cushion (e.g. during sterilization) and it would become thus quasi-inflated, it could happen that the annular cushion comes out from under the cover element resulting in a faulty laryngeal mask.

Since the laryngeal opening is at its destination place during the whole procedure of removing the cover element and the release threads and during the inflation, these steps of the process can be performed without any hindrance in the state when the annular cushion 25 is inflated, thus the intended use of the laryngeal mask on the patient can be started. It is noted that it is possible to perform the inflation, since the collar 29 (see in many figures, e.g. FIGS. 2 and 3) around the laryngeal opening is placed onto its destination place (it is hereby noted that the cover element—here cover element 12, but also the cover element in general—can be removed from between the collar 29 and the anatomy at the destination place) and the annular cushion can be inflated by the help of well-known procedures (in the meaning that annular cushion is contained in known everyday laryngeal masks, which are inserted into the destination place in the patient in an uninflated state).

As illustrated also by the above description, applying this way of operation and the configuration of the laryngeal mask according to the invention it can be reached that a laryngeal mask with smaller dimensions can be inserted into the patient.

FIGS. 17A-17D show a pullable end element 187 having a handle 118 in different views, as well as FIG. 18 in a spatial-sectional view. The pullable end element 187 is very similar to the pullable end element 19 (shown e.g. in FIG. 3); it is to be understood that the pullable end element 19 can be configured in such a way (e.g. with further holes on its hidden side not shown in the figures) that it can be used analogously to which is detailed below pullable end element 187. Naturally, the pullable end element 187 can be used in every embodiment where the pullable end element 19 is shown (at the same time the followings are applicable also to the pullable end element 19).

The lower part of the pullable end element 187 (i.e. its end opposite to the handle 18) is insertable into the connection indentation 41 which can be observed in FIG. 15 (this connection indentation 41 is thus continues on the connector element 16 also inside the end tube 17). The pullable end element 187 has snap members 199 on its both sides (these are the sides connecting the sides/edges with the holes, see below). For the snap members 199 respective snap indentations can be formed in the side wall of the connection indentation 41 in order that the snap members 199 can snap into those. Due to the configuration of the connection indentation 41 and to that it is inserted onto the end tube 17, the pullable end element 187 is connected to the connector element 16 in such a way that it cannot be rotated but it can be grabbed from any direction because of the handle 18 with circular design (well accessible from different directions relative to the patient to whom the laryngeal mask is utilized).

In FIGS. 17A-17D indentations 193 and 195 can be observed with a respective first hole 193*a* and second hole 193*b*, third hole 195*a* and fourth hole 195*b*, as well as a fifth hole 197 (this latter is an auxiliary hole for facilitating the handling of the threads), wherein the holes 193*a*-193*b*, 195*a*-195*b* and 197 (with other word, openings, see also FIG. 18 for these) are responsible for fixing the release threads 40*a*, 40*b* and the puller portion 47 of the cover element 12, preferable according to the following.

FIG. 18 shows the pullable end element 187 in a spatial-sectional view. According to the view, the holes 193*a*-193*b*, 195*a*-195*b* and 197 can be observed (holes 193*a*-193*b*, 195*a*-195*b* are respective hole pairs and hole 197 is a single larger hole). In FIG. 18 an inner space 177 of the pullable end element 187 can be observed; the holes 193*a*-193*b*, 195*a*-195*b* and 197 open to the inner space 177.

It is noted in this respect that in this pullable end element 187, these can be fixed also in another way and also other way of fixing of the release threads 40*a*, 40*b* and the puller portion 47 into an appropriately designed pullable end element (the main aspect is to have an appropriate fixing in it, not the way of fixing). Accordingly, the following way of fixing is an exemplary way.

For the fixing of the release threads 40*a*, 40*b* the following procedure can be chosen in an option:

1. We start with a single thread and fold it at its half to obtain two half thread with two free ends and with a loop (bending) on the other end.
2. After that the two free ends are pushed together through a single hole, e.g. through the hole 197 into the inner space 177 of the pullable end element 187 (in these steps—and in the steps corresponding to the arrangement of the puller portion 47—this will be referred simply as inner space 177), and after that, out of the inner space 177 through a hole, e.g. the hole 193*a* which is just opposite on the pullable end element 187 to the hole 197, leaving the loop outside the inner space 177.
3. Then, the two free ends are pushed back into the inner space 177 through a further hole, e.g. the hole 193*b*, and these are pushed out of the inner space 177 on the other side through the same hole (namely the hole 197), where this procedure started, and after that the free ends are pushed through the loop to have a looped knot on the threads 40*a*, 40*b* (the looped knot can be observed e.g. in FIGS. 7 and 12).
4. After that the two free ends are pushed back to the inner space 177 to maintain the looped knot (which fixes the release threads 40*a*, 40*b* at least to the hole pair—e.g. holes 193*a*, 193*b* in which these were pushed out from and into the inner space, the looped knot fixes the end of the release threads 40*a*, 40*b* to the holes 193*a*, 193*b*) and after that these are led out from the inner space 177 on the opened bottom open end of the pullable end element 187 (the bottom open end is which is opposite to the handle 18, which is arranged on the connector element 16 in FIGS. 16A-16B).

In this way, based on the above and e.g. FIG. 7, the first puller portions 48 of the release threads 40*a* and 40*b* are connected to the pullable end element 187 (with a common looped knot in the above example).

For the fixing of the puller portion 47 the following procedure can be chosen in an option:

1. The free end of the puller portion 47 is introduced to the inner space 177 through the bottom open end of the pullable end element 187 and pushed out from the inner space 177 through a hole thereof, e.g. through the hole 195*b*.
2. After that the free end of the puller portion 47 is pushed back into the inner space 177, through a further hole, e.g. the hole 195*a* and the free end is pulled out of the inner space 177 through the bottom end in order to tie a knot on it (simply knotting itself or using a knot applied for it from an additional material), which is large enough (this can be fulfilled if wide enough puller portion 47 is applied) to avoid going through the holes (namely holes 195*a*, 195*b*).
3. Then, the knot—large enough—is pulled to abut on the further hole (in the example the hole 195*a*).

It is noted that—e.g. for mass production—other solutions for connecting the first and second puller portion into the pullable end element can be applied, which does not require the application of e.g. knots and loops. For example, clamp clips or the like may be applied in such a pullable end element (e.g. the clips clamp the first and second puller portion when inserted into the pullable end element). In this case no holes are to be applied on the sidewall of the pullable end element.

It is noted in connection with FIGS. 15, 16A and 16B that, preferably the release threads 40*a*, 40*b* will be led out from the inner space 177 of the pullable end element 187 and led into the release thread hole 39 (see FIG. 15), and the release threads 40*a*, 40*b* can be further arranged in the thread channel 32. Furthermore, the puller portion 47 will be led into the channel 46 (see FIG. 8A) via the end tube 17 on which the pullable end element is inserted via its central cutout 189.

According to the above, in an embodiment, the first puller portion and the second puller portion (i.e. the first puller portion of the release element, e.g. those of the release threads, and the second puller portion of the cover element) are connected (fixed) to each other at the tube proximal end of the tube portion (in this case the manner of connecting to each other is not specified, but joint pulling is facilitated in this way).

Furthermore, in a more specified embodiment, the laryngeal mask comprises a pullable end element arranged on the tube proximal end of the tube portion and the first puller portion and the second puller portion are connected to each other by means of (in) the pullable end element (i.e. the puller portions of the release element and the cover element are connected to each other this way as illustrated by the help of FIGS. 17A-17D and 18).

It is noted that in case there is a respective first puller element for the release threads, then these are connected to the second puller element, e.g. by means of the pullable end element.

The pullable end element is an end element (meaning that it is on the end of the tube portion; i.e. it is a pullable piece; it may also be called end piece or end member) which is arranged on the tube proximal end of the tube portion and by the help of which the puller portions can be pulled away from the tube proximal end of the tube portion.

In connection with the joint pulling, the followings are also noted. The lengths of the first and second puller portions are preferably sized so and the second puller portion of the cover element left to be loose or there are bends on it so that the displacement of the cover element only starts when the fixing of the cover element to the head portion has been released (e.g. the preferably applied release thread has left all threading elements, see below). Stretching of the puller portions is negligible, these are not pulled under resistance. See also the below description based on which it can be understood that the lengths of the puller portions can be chosen in accordance with the above.

When the release threads with the first puller portion and the cover element with the second puller portion is prepared, these can be preferably connected into a pullable end element (in this way, these are fixed to each other). Accordingly, for the preparation, it is the relevant property how far these extend from the pullable end element (namely, from the opened bottom thereof from which both come out, cf. FIGS. 17A-18).

To achieve this the full length of the thread from which the release threads are composed when it is connected into the pullable end element can be determined (if it is too long it can be cut to size, see below). Moreover, since the second puller portion of the cover element is connected into the pullable end element preferably by the help of applying a knot, the position of the knot is preferably predetermined (naturally, other connections are conceivable).

For a first length of the release threads from the bottom of the pullable end element, preferably a first predetermined minimum value is required. Preferably, this will be set to be tight (i.e. tightly arranged) when threaded into the head portion and the free ends of the release threads can be cut.

For a second length from the bottom of the pullable end element until the farthest point of the second puller portion and the corresponding cover element, a minimum value is also predetermined. These may run in different channel (it can be understood that a length difference between their length can be determined) but the second length is larger than first length at least which such an extent that the release threads will be pulled from the head portion with a safe certainty when the second puller portion of the cover element become tight and starts to be pulled out. Not to be excessively long, a preferred second predetermined value is determined with a small tolerance compared to its length (e.g. ±0.5-1 cm). It is thus noted that, preferably, puller portions (actuators) having different length are applied. Accordingly, the cover element is made free earlier and the force removing it only reach the cover element only afterwards (this is a kind of geometrical delayed mechanism).

The release threads and the cover element reach their destination place when these are pushed in so that the pullable end element is connected to the connector element and the release threads are threaded into the head portion and the cover element. In this state the second puller portion of the cover element will have some looseness, but, preferably, the release threads are pulled by their free ends to be tight and the excess length thereof can be cut. The tightness of the release threads ensures that these will start being pulled out when the pullable end element is removed from the connector element and the looseness of the second puller portion of the cover element will allow that the cover element will start being pulled when the fixing of the cover element to the head part is already released.

In case of the cover element and its second puller portion, these can be differentiated easily. This differentiation of the first puller portion on the release threads can be made as follows. The first puller portion can be the elongation of the release thread until the tube proximal end of the tube portion, which is not threaded into the head portion and the cover element (see also below). In this approach it can be said that, preferably, the second puller element is selected to be longer than the first puller element—considering their arrangement between the head portion and the tube proximal end of the tube portion—(i.e. the first puller element and the second puller element is configured in a way) so that when their ends at the tube proximal end are pulled together, the pulling of the cover element only starts when the fixing of the cover element to the head portion by means of the release threads is released. The lengths of the first and second puller elements is selected in view of the length of the tube portion (according to the mask sizes for child or adult, etc.).

Figure 20:
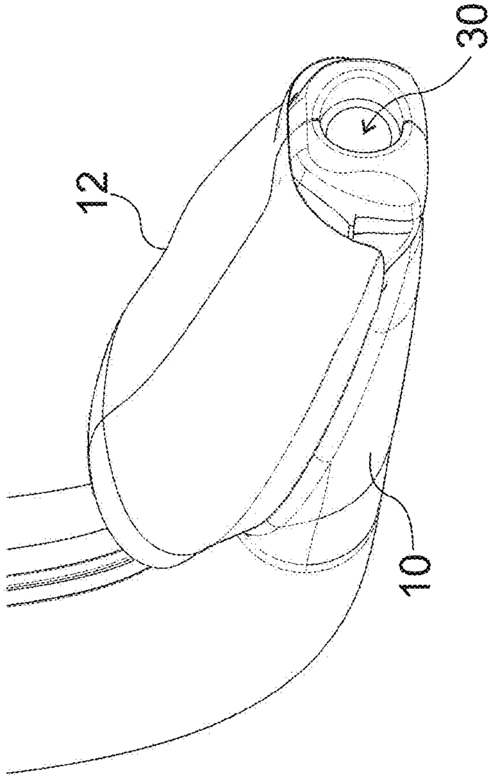
FIGS. 19-32 show section of use the first embodiment of the invention from front and spatial views.
Figure 19:
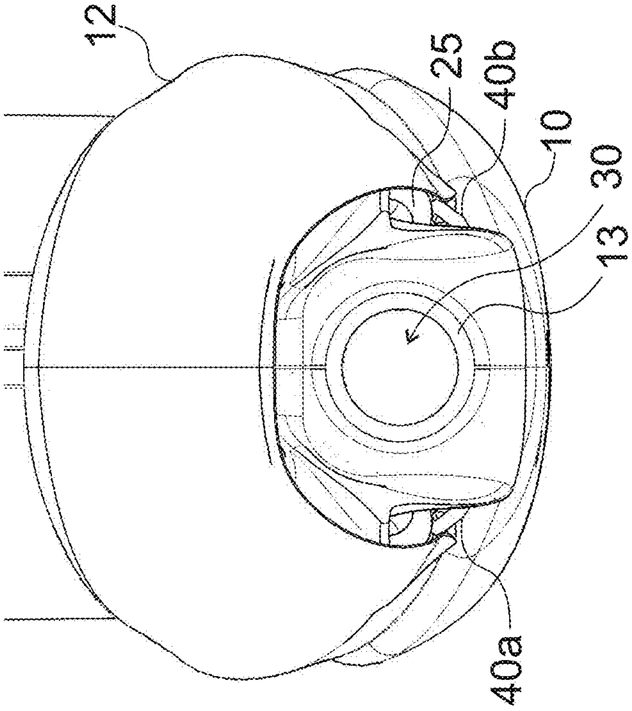

In FIGS. 19-32 various (consecutive) cross-sections of the first embodiment of the laryngeal mask are shown (strictly, FIGS. 19 and 20 are not cross-sections but views since these are the starting points of the cross-sections where sectioning is not applied yet, see FIG. 1 for comparison with FIGS. 19 and 20).

Accordingly, in FIGS. 19 and 20 a front view and a spatial view of the first embodiment are shown (see the gastric tube 13 and the gastric hole 30 denoted). FIGS. 19 and 20 show the assembled state of the first embodiment, thus the cover element 12 is connected to the head portion 10 by the help of the release threads 40. In this respect, FIGS. 19 and 20 are complementary figures to FIG. 1 and FIG. 8A, all of these figures can also be interpreted together (also with other cross-sections).

Because of the different views compared to above mentioned figures, FIGS. 19 and 19 show some additional details of the assembled state of the first embodiment of the laryngeal mask. In this view, the end of the gastric tube 13 can be seen in the front. Furthermore, more details can be seen in the portion around the gastric tube 13. Accordingly, the ends of release threads 40*a*, 40*b* can be seen (about the arrangement of these see further details below). Furthermore, the rolled annular cushion 25 can be slightly observed.

It is to be understood based on the section views of FIGS. 19-32 that the cover element 12 is arranged as follows. The cover element 12 has respective rows of holes at its two sides (edges) of its main part (cf. with FIG. 13). These rows of holes are folded onto the threading grooves 22 on the two sides of the head portion 10, respectively (cf. e.g. with FIG. 10); this is a folding with the meaning that cover element 12 encompasses, "encapsulates" the annular cushion 25, thus the rows of holes at its edges simply go between the annular cushion 25 and the threading grooves 22 (inserted between these) at the two sides of the head portion 10 (see for further details below).

Figure 22:
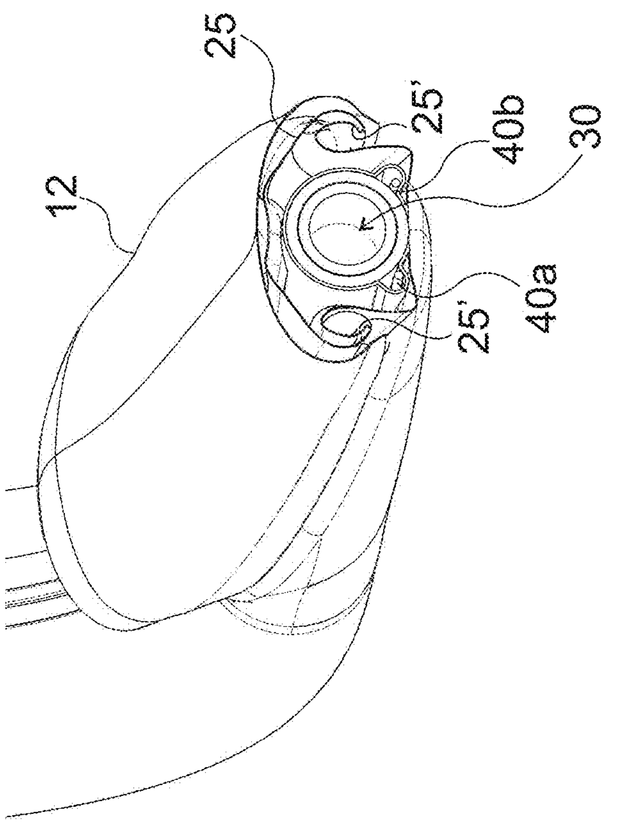
Figure 21:
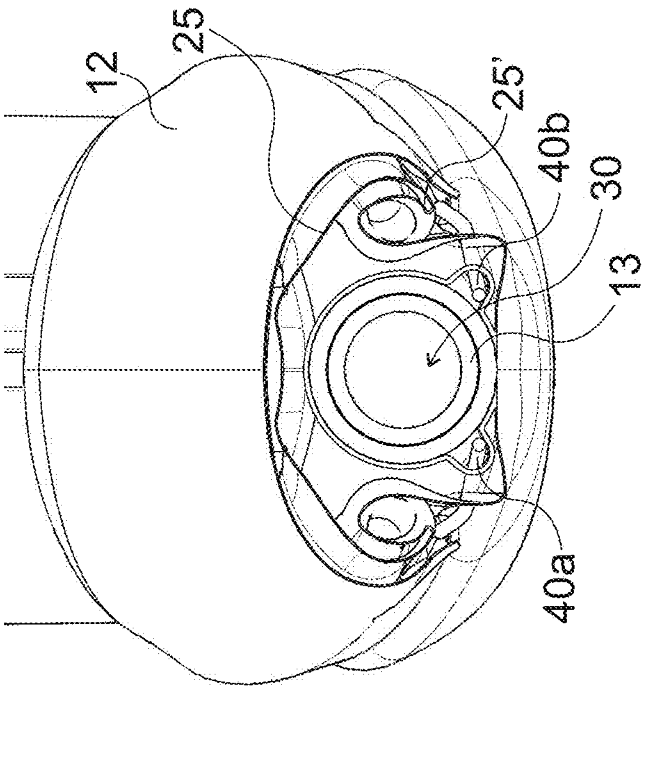

FIGS. 21 and 22 show a first cross-section of the laryngeal mask from the same view as FIGS. 19 and 20. In FIGS. 21 and 22 also the portion around the gastric tube 13 is to be observed. In this portion the rolled-up part of the annular cushion 25 can be seen, i.e. rolled-up annular cushion wings 25'—i.e. side parts of the annular cushion 25—are also denoted.

Furthermore, as an important detail, a part of the release threads 40*a*, 40*b* can be observed in both of FIGS. 21 and 22, namely (see FIG. 21) that parts which come out from below the annular cushion wings 25' and have respective ends very close to the gastric tube 13. This latter shows how the release threads 40*a*, 40*b* are inserted here. This insertion is made into the material of the annular cushion 25 (in this respect we refer to FIG. 38 with insertion places 60 for this embodiment). The two views of FIGS. 21 and 22 are shown in order to the details of the components be as understandable as possible.

The following figures show that not all of the cross-sections are illustrated from multiple views, but we included those views which are considered to be the most necessary for understanding.

Figure 23:
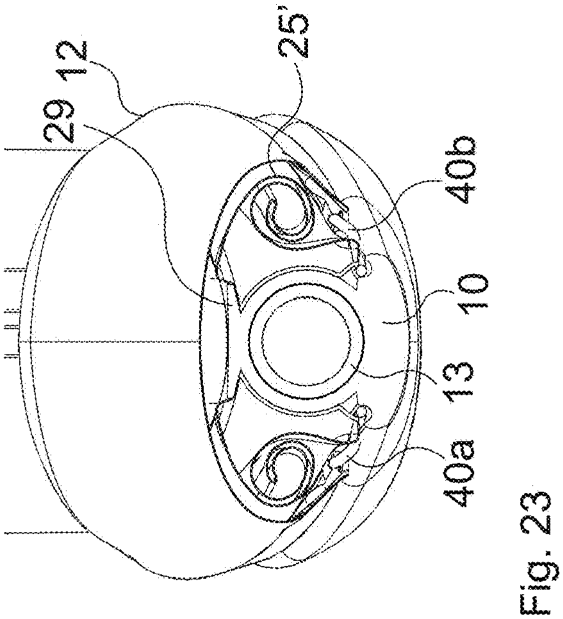

Accordingly, FIG. 23 shows a further cross-section in a front view. In this cross-section, also the portion around the gastric tube 13 is relevant. In this cross-section the rolled-up annular cushion wings 25' are observable. Furthermore, the release threads 40*a*, 40*b* are observable also in this cross-section. Comparing with FIG. 24, it can be understood that in these two cross-sections, the arrangement of the release threads 40*a*, 40*b* are shown vis-à-vis the respective threading grooves 22*a*, 22*b*.

Figure 24:
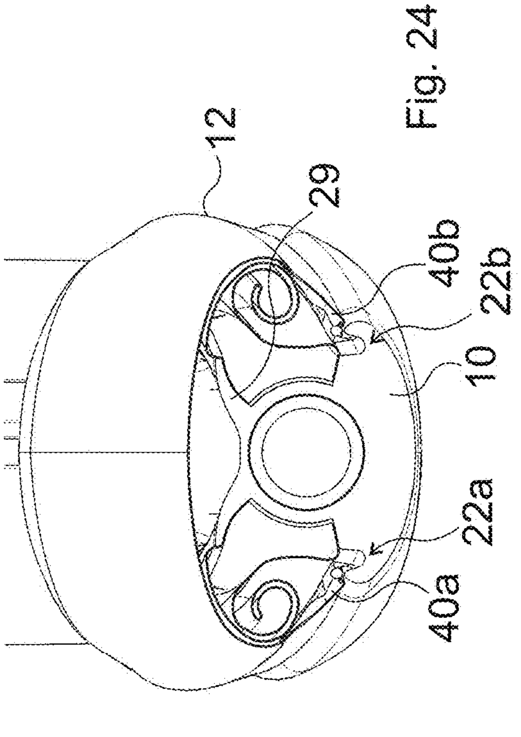
Figure 25:
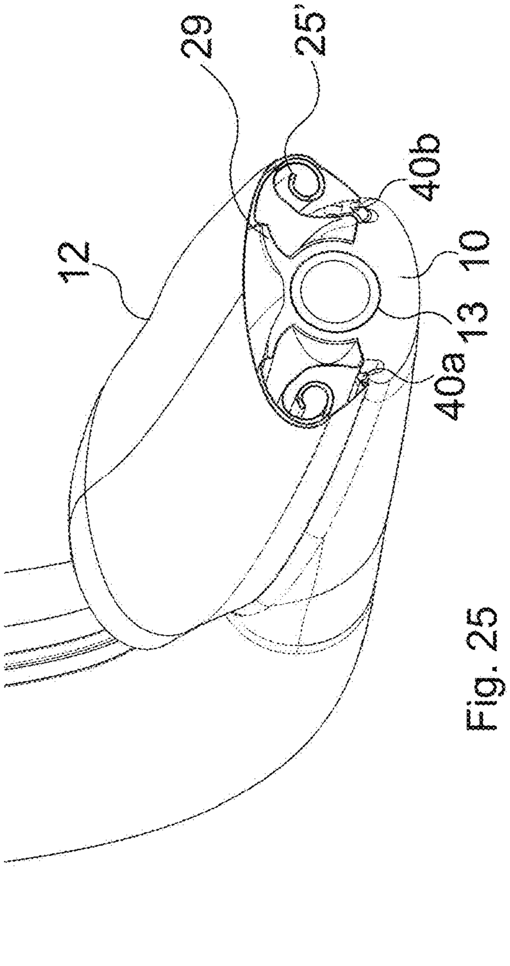

FIG. 25 shows the same cross-section as illustrated in FIG. 24 with emphasize on the details around the gastric tube 13, which illustrates according to the above that the release threads 40*a*, 40*b* run between the material of the edge the cover element 12 and the annular cushion 25.

Figure 26:
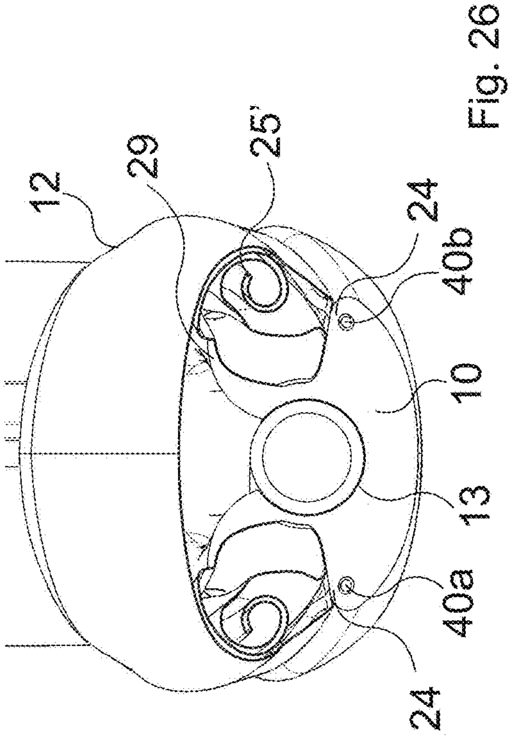

Comparing also with the next cross-section in FIG. 26, it is also observable that in the cross-section of FIG. 26, the release threads 40*a*, 40*b* run in the material of the head portion 10 just under the bridge elements 24. Hence the comparison of FIGS. 24 and 25 shows that between two bridge elements 24 (or other kind of threading element) the release threads 40*a*, 40*b* run between the materials of the cover element 12 and the annular cushion 25, but at the bridge elements 24 the release threads 40*a*, 40*b* "go out" from the cover element 12 "go (more) into" the respective threading grooves 22*a*, 22*b* and go below the bridge element 24 (in the threading groove part being under it) in order to anchor the cover element 12 to the head portion 10. FIG. 26 shows exactly in its cross-section that part of release threads 40*a*, 40*b* which are under the bridge element 24 and also those parts of release elements 40*a*, 40*b* which continuing parts thereof and run between the cover element 12 and the annular cushion 25.

Figure 27:
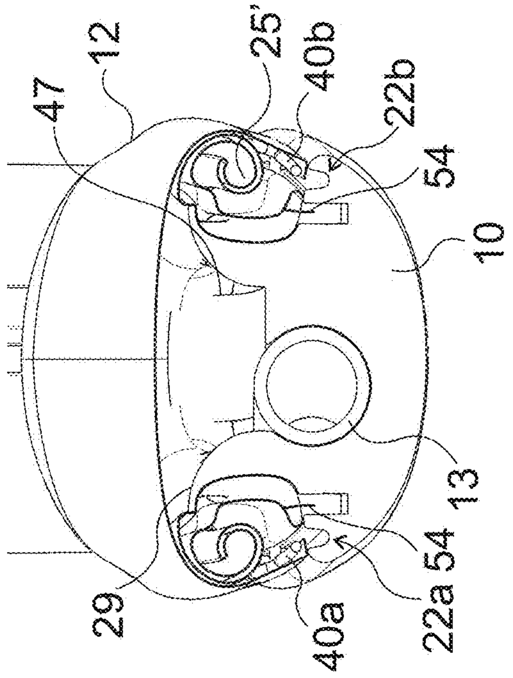

Going further with the cross-sections, this kind of running of release threads 40*a*, 40*b* is observable also in FIG. 27: the release threads 40*a*, 40*b* are between the edge parts of the cover element 12 and the material of the annular cushion 25, and not in the respective threading grooves 22*a*, 22*b*. FIG. 27 also illustrates how the configuration of the head portion 10 changes along the cross-sections. In this respect we also refer to FIGS. 23-26 where the collar 29 starts to develop.

FIG. 27 shows a further detail, namely the manner of connection of the annular cushion 25 to the head portion 10. This connection is made by the help of connection projections 54 which are connected to the respective connection grooves 38 on the two sides of the laryngeal opening 28 (see e.g. FIG. 10, for the connection projections 54 see also below).

Figure 28:
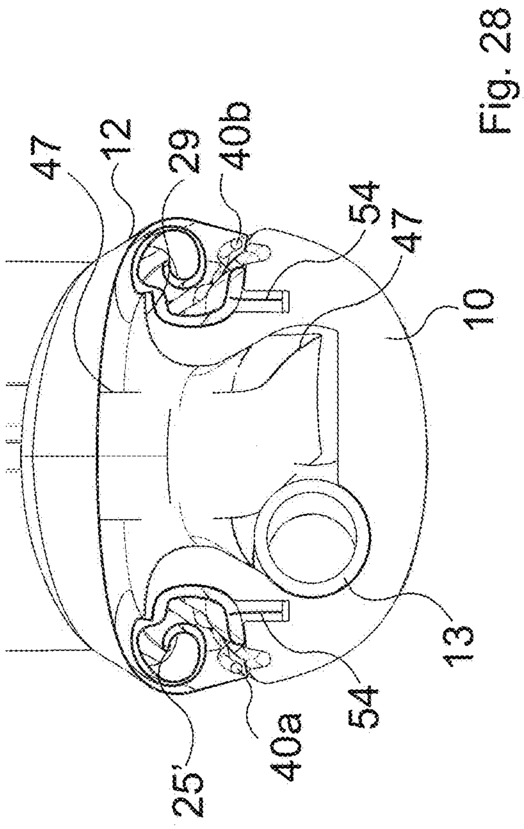
Figure 29:
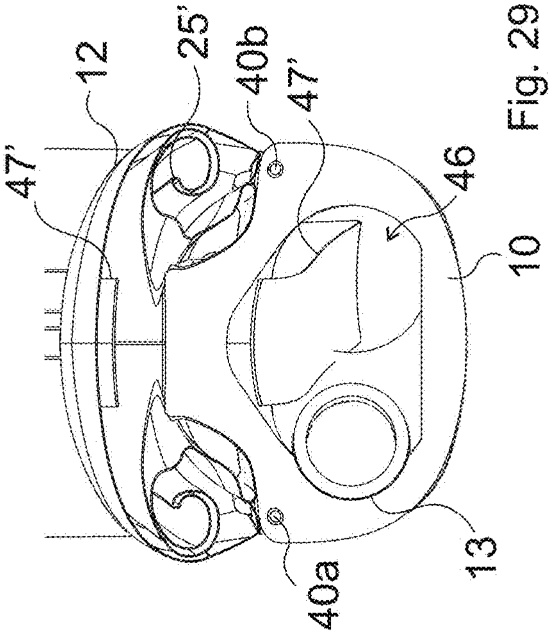
Figure 30:
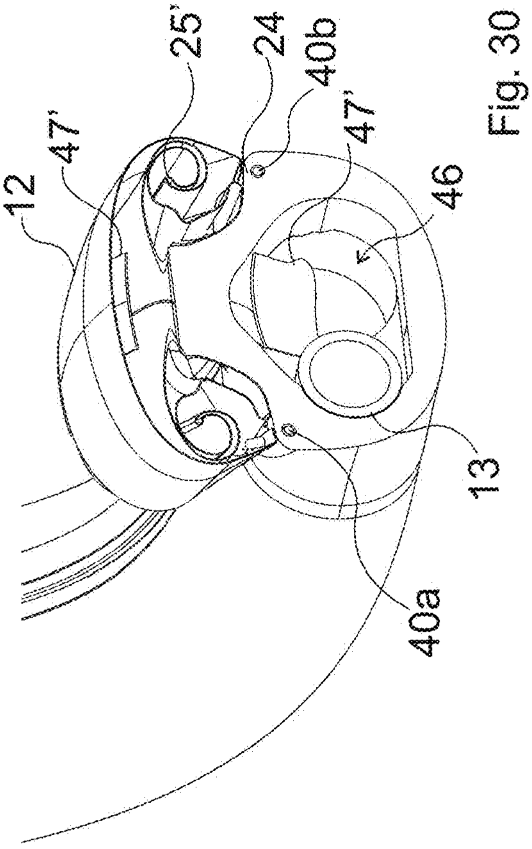

In the cross-sections of FIGS. 27-29 the puller portion 47 of the cover element 12 becomes visible since it is bent in a way that it goes from the end of the main part of the cover element 12 into the channel 46 shown in FIG. 29 (cf. FIGS. 8A-8B and 12).

In FIGS. 27-29 (see also FIG. 30) the arrangement of the gastric tube 13 vis-à-vis the head portion 10 (cf. also with FIGS. 21-26), namely that the gastric tube 13 starting from the centre at the head distal end of the head portion 10 and goes sideways in order to be run into one of the inner channels (namely inner channel 44) of the tube portion 14.

Furthermore, in FIGS. 27-30 the running of the release threads 40*a*, 40*b* is also observable outside and inside the respective threading grooves 22*a*, 22*b* in FIGS. 27-28 and FIGS. 29-30, respectively. Yet further, the rolled-up material of the annular cushion wings 25' can be observed in different cross-sections.

In FIGS. 29 and 30 also two pieces 47' of the puller portion 47 can be observed since this cross-section is close to the end of the cover element 12 where the puller portion 47 connected thereto is bent back in order to be able to go into the respective inner channel of the tube portion 14.

Also, in connection with FIGS. 27-30 the changes in the configuration of the head portion 10 are to be noted. The head portion 10 is configured so that to allow the arrangement of the gastric tube 13 and to form the collar 29 (the ending/closing of which can be observed in FIG. 28).

In FIGS. 29 and 30 we are almost in the tube portion 14, thus the collar 29 is ended there. FIGS. 29 and 30 correspond to the same cross-section.

Figure 31:
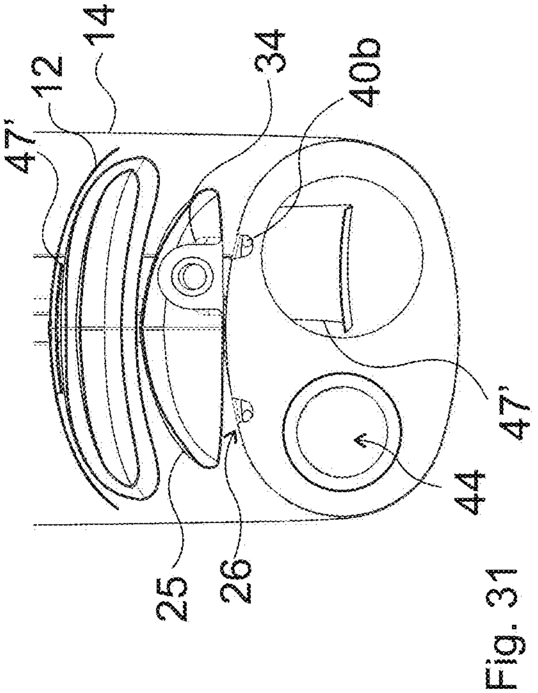
Figure 32:
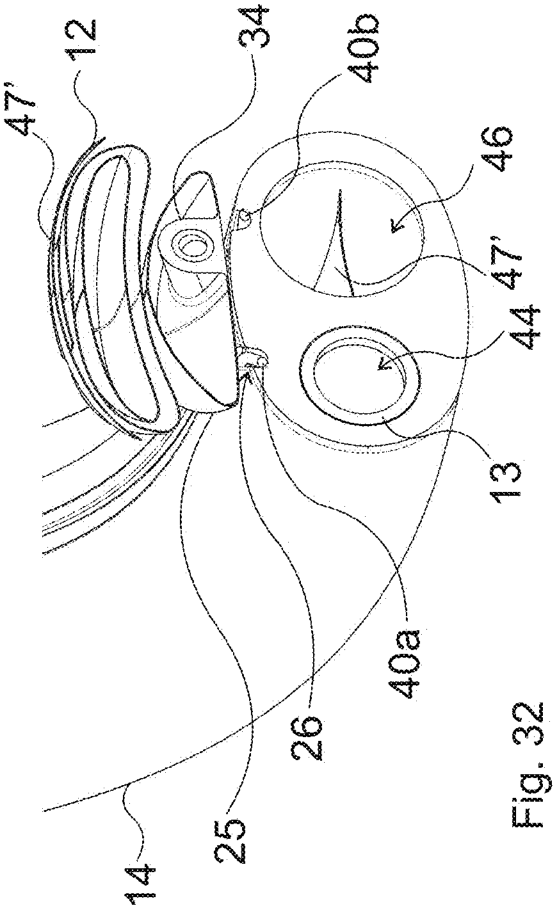

In FIGS. 31 and 32 the last cross-sections of the row of cross-sections are shown, the same cross-section in FIGS. 31 and 32. This cross-section corresponds to the end of the tube portion 14 being at the head portion 10. In accordance with this we can see the end of the gastric tube 13 as well as we can see a piece 47' of the puller portion 47 arranged in the inner channel of the tube portion 14.

Figure 39:
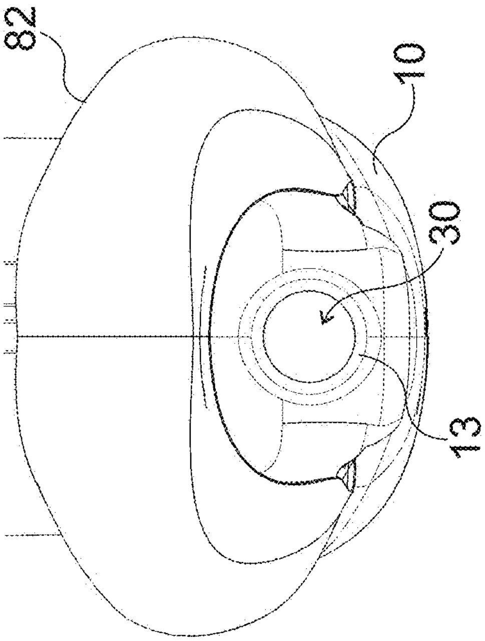
Figure 64:
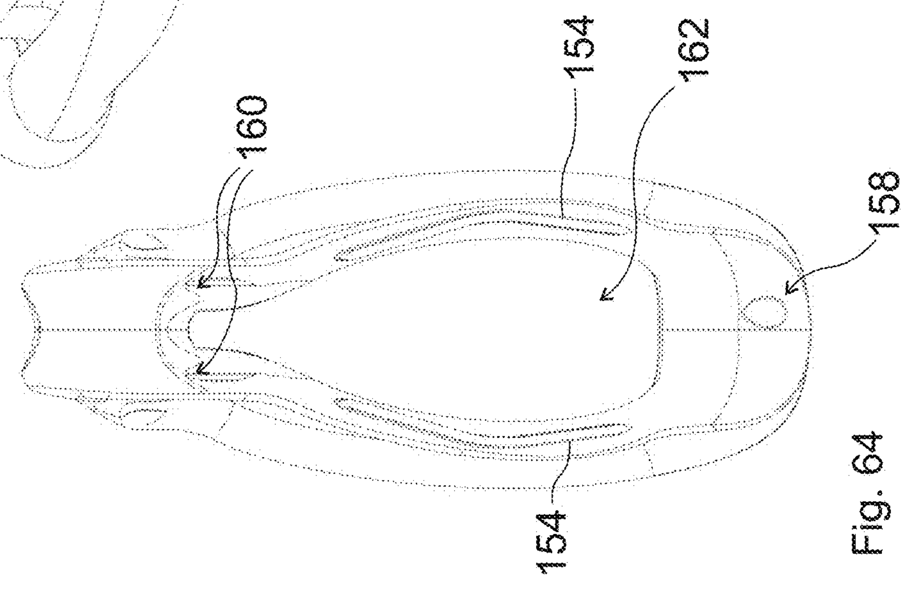
FIG. 64 shows the annular cushion of the third embodiment in a second variant from different views.

In this cross-section the details show an inflation inlet part 34 arranged at the end of the inflation tube 20 (the inflation inlet part 34 is a constructional detail which is formed inside the annular cushion 25 at the inflation hole—see the respective inflation holes 58, 158 in FIGS. 39 and 64, where the inflation tube can be inserted). This cross-section also shows that this inflation inlet part 34 is opened to the inner part of the annular cushion 25. Furthermore, at the top of the cross-section the end of the main part of the cover element 12 can be seen and a piece 47' of the puller portion 47. As a further important detail, FIGS. 31 and 32 show the release threads 40*a*, 40*b* run in threading groove pieces 26.

Herebelow, assembling of the laryngeal mask into its assembled state—see e.g. FIG. 1—is schematically described for the first embodiment (this is an exemplary way of assembling). In this disclosure it is illustrated how the cover element, as well as the release threads are arranged.

Referring to FIGS. 17A-18 by the help of which it has been illustrated how the first puller portion of the release threads as well as the second puller portion of the cover element can be connected to a pullable end element. The release threads 40*a*, 40*b* as well as the cover element 12 with the first puller portion 47 connected to the pullable end element this way are introduced into the thread channel 32 via the thread hole 39 (cf. FIGS. 9B and 14-15) and into the end tube 17, respectively.

After that the release threads 40*a*, 40*b* are pulled through the thread channel 32, as well as the cover element 12 with the first puller portion 47 is pulled through the tube portion 14, namely its channel 46 (cf. the latter with FIG. 8A).

The cover element 12 is fitted to its place and the release threads 40*a*, 40*b* are threaded started from the end of the threading grooves 22*a*, 22*b* being at the thread channel 32. This threading is performed in an alternating manner (see the release threads configured to be alternating in FIG. 7):

- the release threads 40*a*, 40*b* come into between the annular cushion 25 and the cover element 12;
- at the first hole from the row of holes the release threads 40*a*, 40*b* go below the cover element 12 and also go below the bridge element 24 which is closest to the thread channel 32;
- after that the release threads 40*a*, 40*b* go through the next hole into between the annular cushion 25 and the cover element 12 and run here until the next bridge element 24 surrounded by two holes and there go below the bridge element 24 and come up via two consecutive holes of the cover element;
- this last step is repeated until the last bridge element (farthest from the thread channel 32) is passed, after which the release threads 40*a*, 40*b* go into between the annular cushion 25 and the cover element 12, and the end of the release threads 40*a*, 40*b* is cut if these are too long and inserted into the annular cushion to their insertion places 60 (cf. FIG. 38).

It is noted that more generally, alternating manner for threading means that in many cases, there are two holes in the cover element around a threading element—i.e. in accordance where the cover element is to be placed—and to the first hole and from the other hole the release thread runs within the cover element, but at the threading element—going out in the first hole and coming back in the another hole—the release thread goes through the threading element (i.e. goes below the bridge element in the threading groove) thereby anchoring to that threading element. Furthermore, this is repeated for the other similar type (pass-through type) threading elements.

In this way the assembled state is ready, the cover element 12 become fixed to the head portion 10 by means of the release threads 40*a*, 40*b*.

Figure 33:
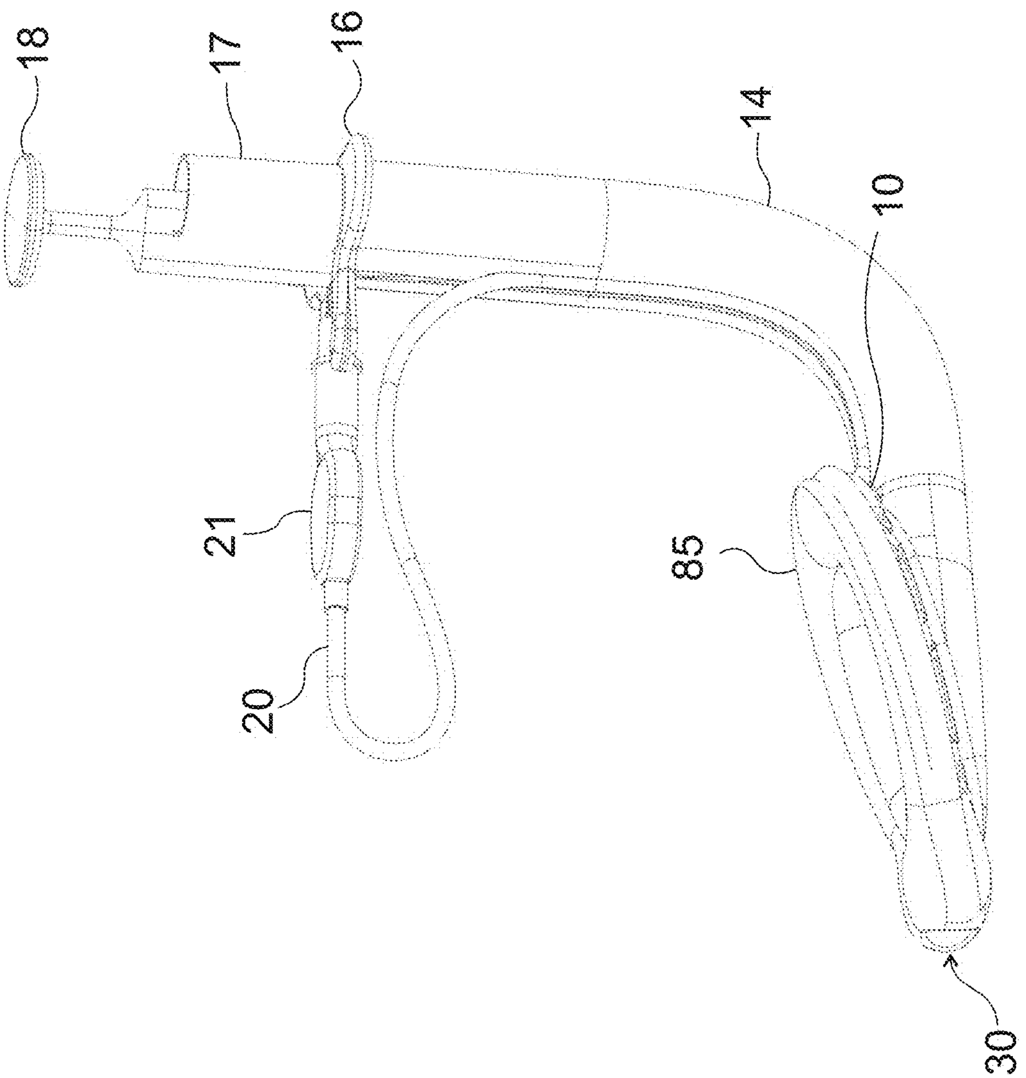
FIG. 33 shows the second embodiment of the invention being different in the arrangement of the annular cushion from the first embodiment.
Figure 34:
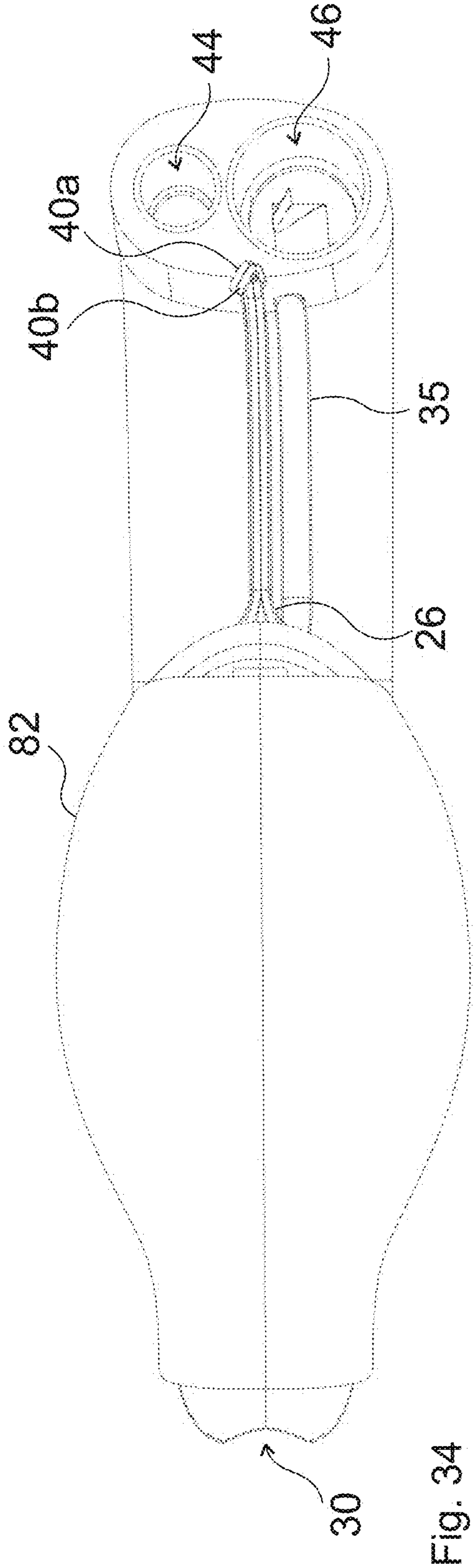
FIGS. 34 and 35 show the second embodiment of FIG. 33 from an upper view with and without cover element.
Figure 35:
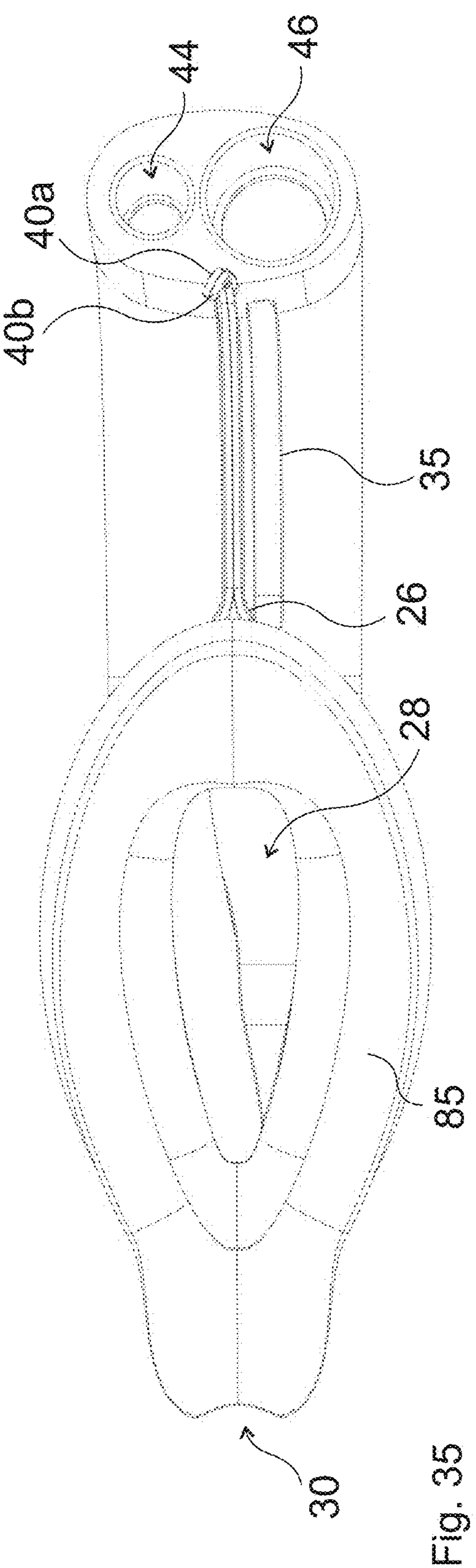

FIGS. 33-38 illustrate a second embodiment of the laryngeal mask according to the invention, differing from the first embodiment only in that the second embodiment comprises an annular cushion 85 having a folded configuration when it is under the cover element, and not rolled up configuration (see the gastric hole 30 denoted in FIGS. 33-35). The manner of folding is illustrated also in other figures of the second embodiment, and in details in FIGS. 39-54. In general, instead of rolling up, the material of the annular cushion 85 is folded onto each other as layers as the various cross-section illustrate in FIGS. 39-54. In the inflated state there is no substantial different based on the "manner of packing" (i.e. rolled up or folded packing).

In FIGS. 34-35 the second embodiment of the laryngeal mask is shown in an upper view with and without a cover element 82, similarly to FIGS. 8A-8B. It is observable in FIG. 34, how the cover element 82 is covered, as well as it is illustrated in FIG. 35, how the cover element 82 is folded (being in the same state as if it would be covered). Also, a thread channel (like the thread channel 32) is not shown in this view (it is not applied or simply removed to show that section the release threads 40*a*, 40*b*).

Figure 36:
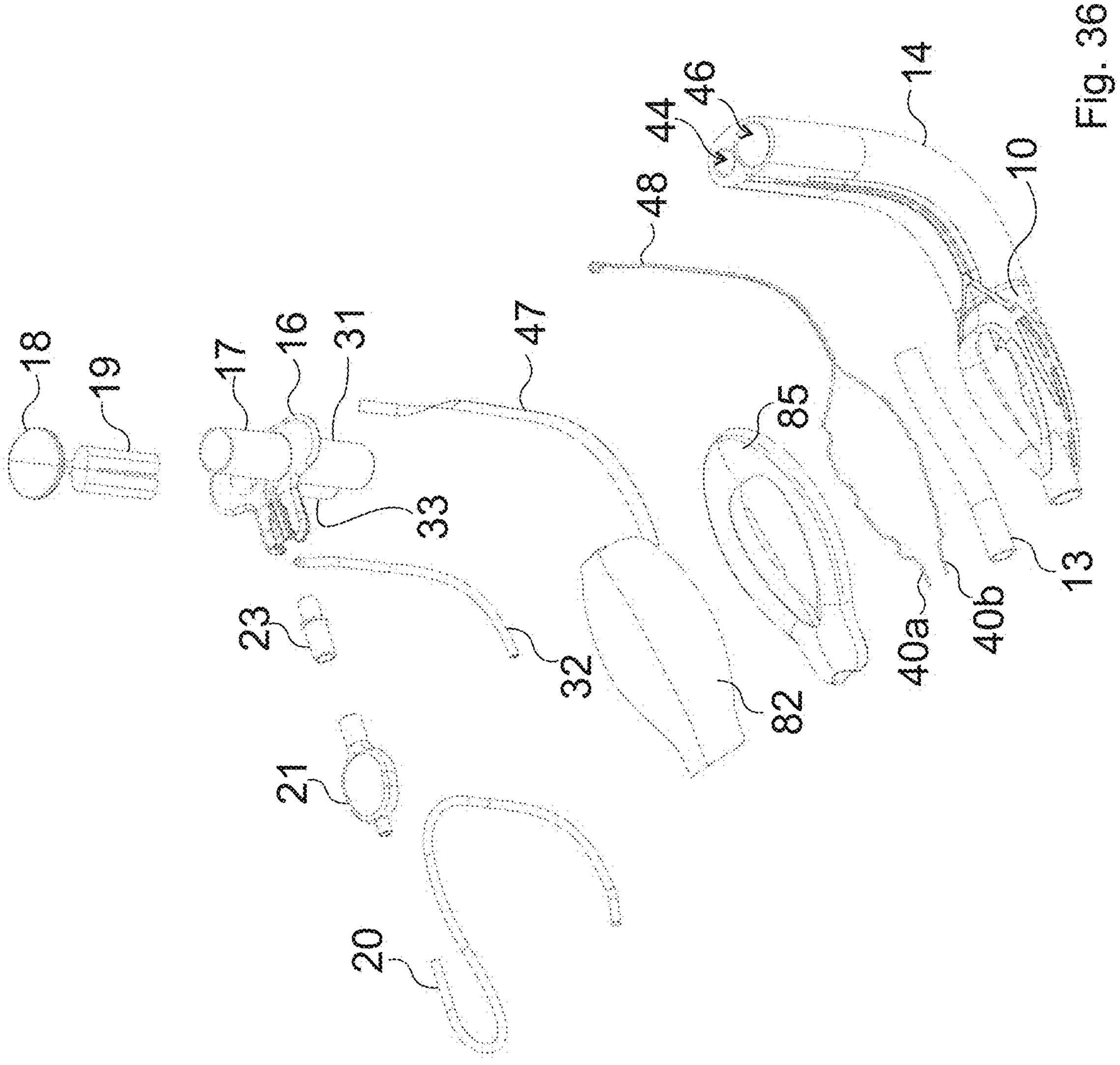
FIG. 36 shows the second embodiment of the invention in an exploded view.

FIG. 36 shows an exploded view-similarly to FIG. 12-of the second embodiment. Due to the similarity, FIG. 36 can also be interpreted by the help of the description of FIG. 12 above. It can be seen that mainly the annular cushion 85 (folded differently) means the difference from FIG. 12, according to which a somewhat different cover element 82 is to be utilized, which can preferably tightly cover the annular cushion 85.

The other components are shown in FIG. 36 from a different view, but it can be observed that the same components are included as in the first embodiment.

Figure 38:
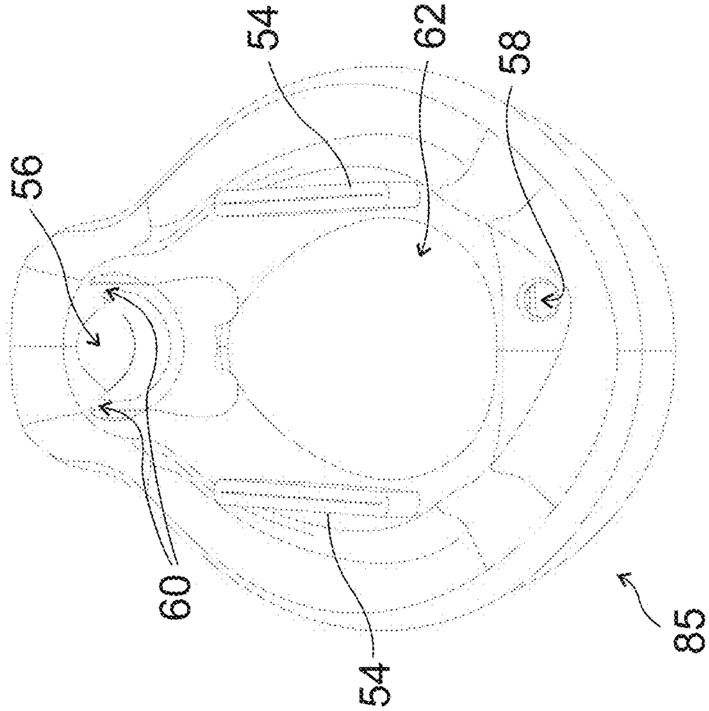
FIGS. 37-38 show the annular cushion separately of the second embodiment of the invention in different views.
Figure 37:
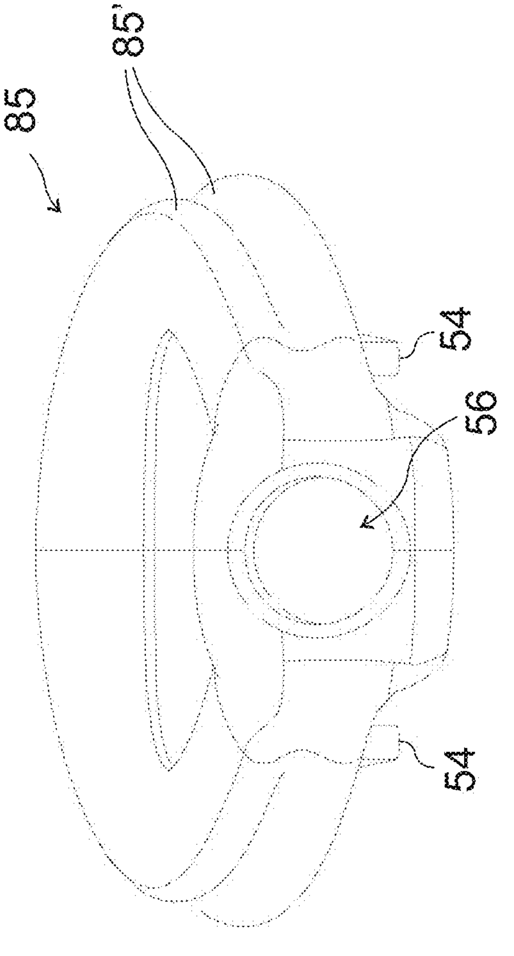

In FIGS. 37-38, the annular cushion 85 is shown in different views in its uninflated state, i.e. also the folding of the annular cushion 85 can be observed (see annular cushion wings 85' in FIG. 37).

Another detail which can be observed clearly based on the different views of FIGS. 37-38 is the arrangement and configuration of connection projections 54 (see in particular FIG. 38). These are similarly configured that in the first embodiment (that is why the same reference number has been utilized for them; cf. FIG. 27-28, where the connection projections 54 are denoted).

In FIGS. 37-38 it can be observed that the connection projections 54 are arranged on the two sides of a cushion opening 62, which will fit to the laryngeal opening when the annular cushion 85 is fitted onto the head portion 10. The connection projections 54 are connected into the respective connection grooves (cf. with FIG. 10 where a connection groove 38 can be observed).

For assembling the laryngeal mask, preferably liquid glue (adhesive; in the following: simply, glue) can be applied in various steps of manufacturing. First, the annular cushion 25 can be preferably pulled onto the head portion 10 from the distal part (inserting the distal tip into the gastric hole-of the annular cushion), the pulling can be performed so that preferably glue is applied to the portion between the distal tip and the nearby part of the collar 29. After that the connection projections 54 can be connected into the connection grooves 38 by applying glue. Preferably, glue can be applied around the end of the gastric tube 13 (see elsewhere for the insertion thereof) at the head distal end and around the collar 29, where these are bounded by the material of the annular cushion 25. The connection projections 54 may preferably also help to remove the manufactured annular cushion 24 from the mold (the annular cushion 25 can be grabbed at the connection projections 54).

FIGS. 37-38 also show a gastric hole 56 and insertion places 60 (see FIG. 38) wherein the respective (free) ends of the release threads 40*a*, 40*b* can be inserted. FIG. 38 also shows an inflation hole 58 on the annular cushion 85 through which it can be inflated.

Figure 40:
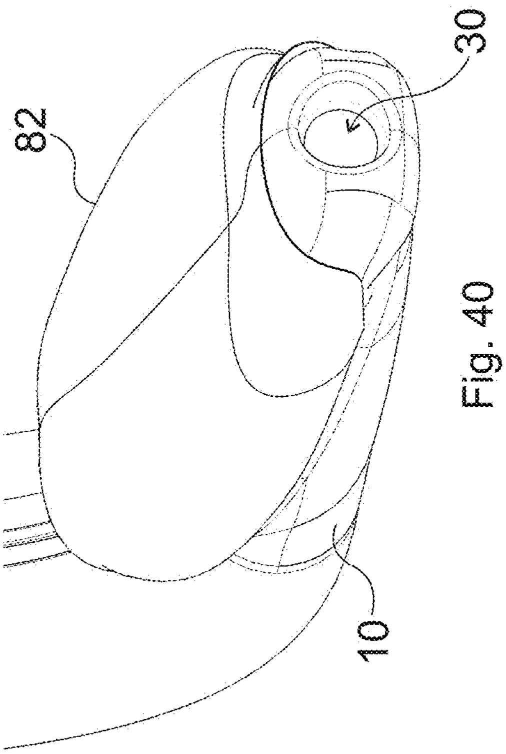
FIGS. 39-54 show section of use the second embodiment of the invention from front and spatial views.

In FIGS. 39-54 different cross-sections of the second embodiment of the laryngeal mask are shown from front and spatial views, starting also with a spatial view having no section (these are FIGS. 39-40; see the gastric tube 13, as well as the gastric hole 30 denoted).

The comparison of FIGS. 39-40 to FIGS. 19-20 of the first embodiment show that the front configuration of the cover element 82 is different from that of cover element 12 (the second embodiment is a little bit more closed at the front by the cover element 82). In these views the gastric tube is in the centre as in the above cross-sections, and also its arrangement within the head portion 10 can be observed by the help of the following cross-sections.

Figure 42:
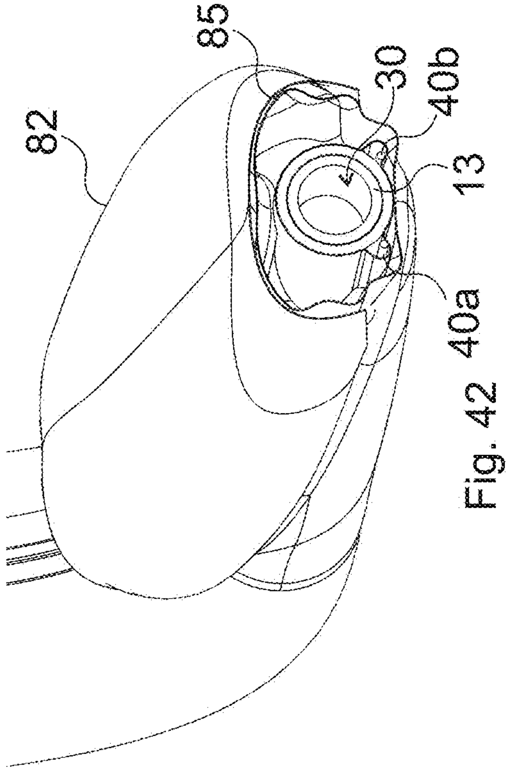
Figure 41:
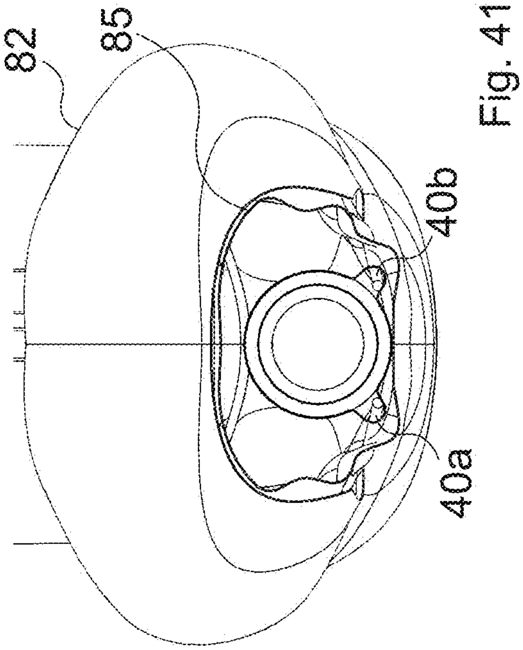

In FIGS. 41 and 42 a first cross-section is shown in two views. In this cross-section an end portion of the release threads 40*a*, 40*b* can be observed. These run close to the gastric tube similarly to the first embodiment. In FIGS. 41-42 a slight folding of the annular cushion 85 can be observed.

Figure 44:
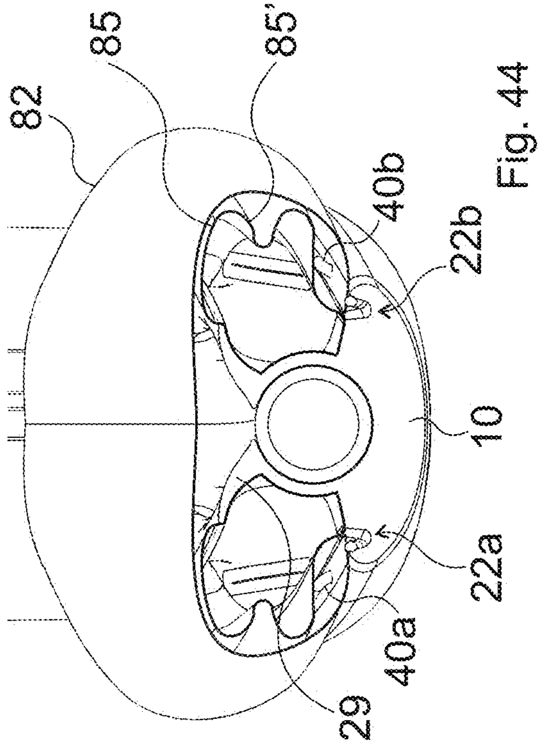
Figure 43:
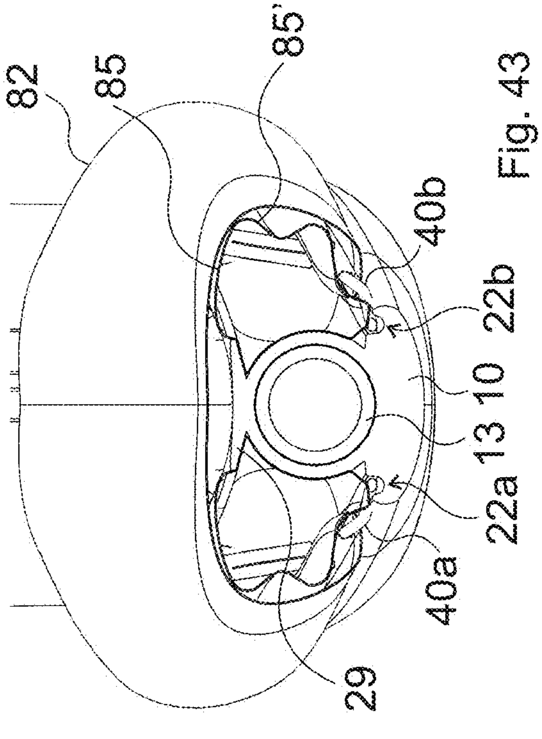
Figure 45:
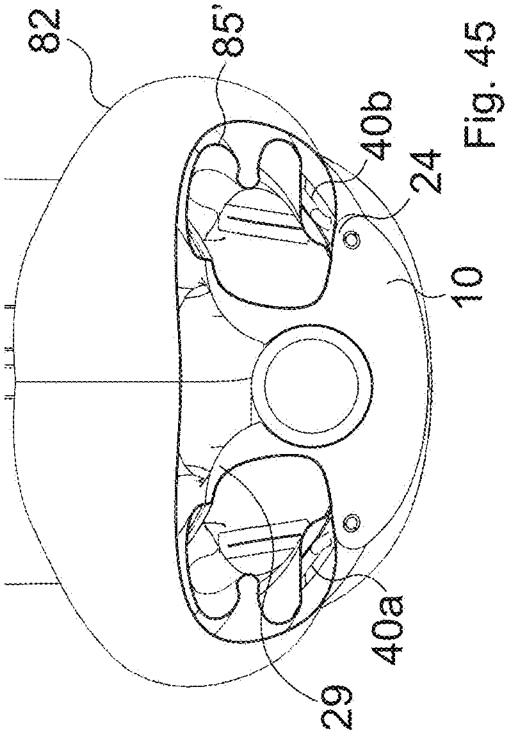

In FIGS. 43-45 further cross-sections are shown.

In FIG. 43 also an end portion of the release threads 40*a*, 40*b* can be observed. In this cross-section, the section part of the head portion 10 is shown and the release threads 40*a*, 40*b* run in the respective threading grooves 22*a*, 22*b* of the head portion 10. The running of the release threads 40*a*, 40*b* is good to be observed by the comparison of FIGS. 43-45.

In FIG. 45 the cross-section is at a bridge element 24, i.e. at this cross-section the release threads 40*a*, 40*b* run in the threading grooves 22*a*, 22*b*. Comparing with the cross-section of FIG. 43 closer to the front, it can be seen in FIG. 44 that the release threads 40*a*, 40*b* tend to go under the bridge elements 24, and we can see a farther part of the release threads 40*a*, 40*b* in FIG. 44 showing that these run between the cover element 82 and the annular cushion 85 and it can be also observed in FIG. 44 according to the arrangement of the release threads 40*a*, 40*b* that these just go through respective holes of the cover element 82.

Figure 46:
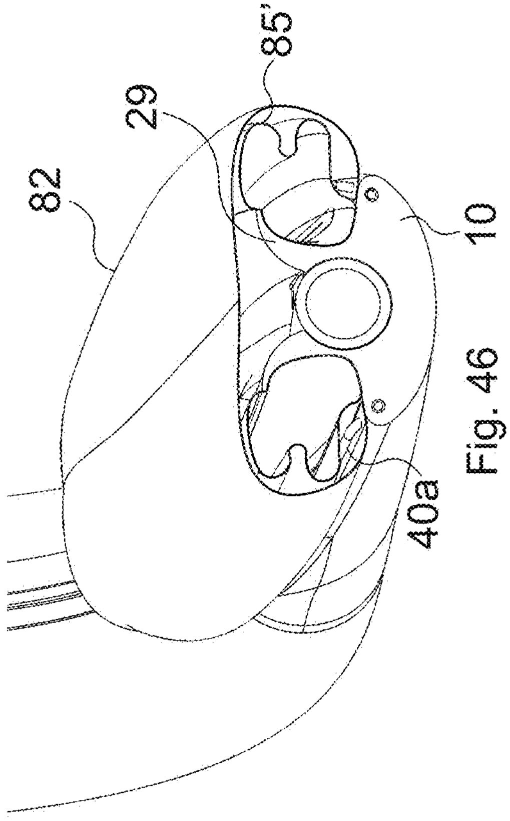

In FIGS. 43-45 the formation of the annular cushion wings 85' can be observed, i.e. these are folded more and more in the cross-sections farther and farther from the front (head distal end) of the laryngeal mask. FIGS. 45 and 46 show the same cross-section from different views by the help of which the collar 29 can be better observed.

Figure 47:
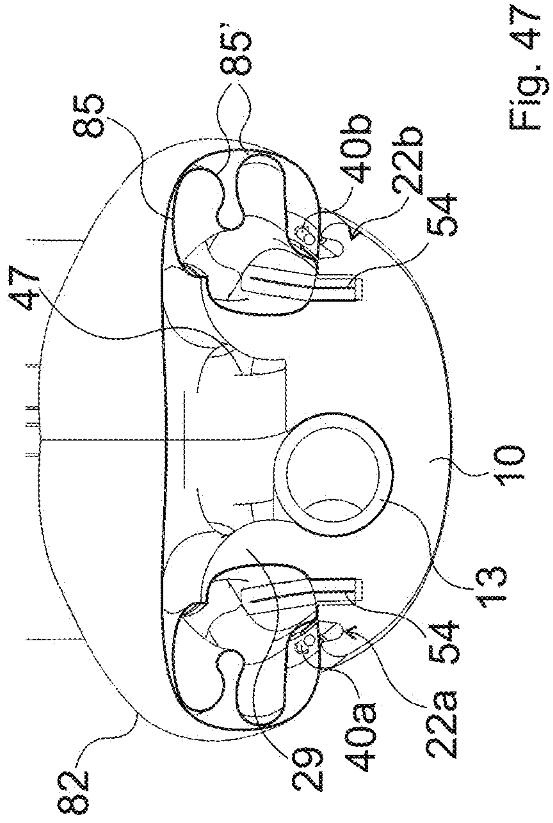
Figure 48:
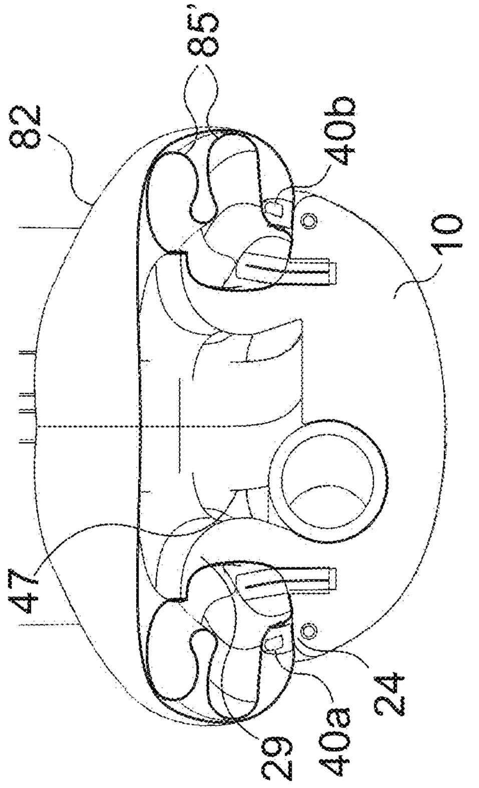
Figure 49:
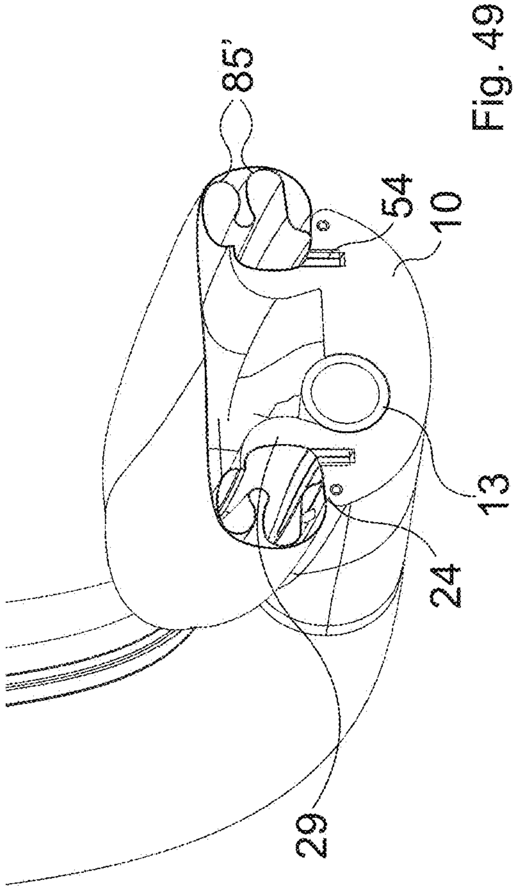
Figure 50:
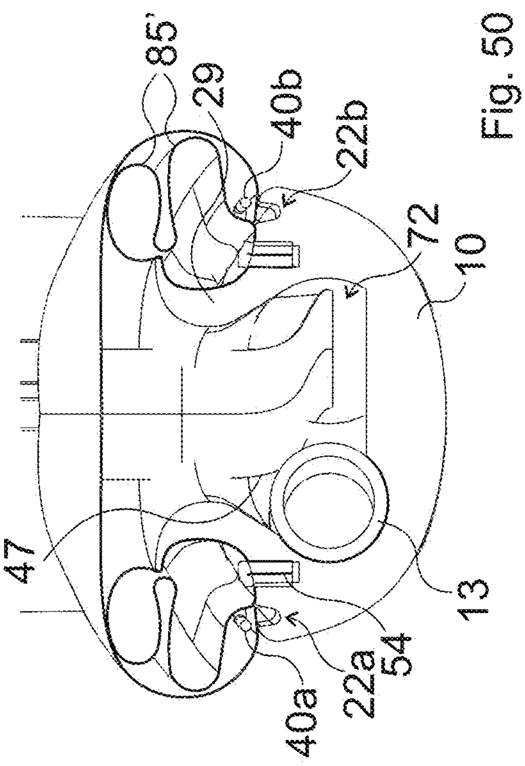

In FIGS. 47-50 further cross-sections are shown (FIGS. 48 and 49 correspond to the same cross-section).

In FIG. 47 many details of the configuration can be observed. In connection with the running of the release threads 40*a*, 40*b*, it can be observed in FIG. 47 that the these run between the material of the cover element 82 and the material of the annular cushion 85. This can be clearly observed since there is the material of the cover element 82 between the sectioned end of the release threads 40*a*, 40*b* and the threading grooves 22*a*, 22*b*. These can be observed also in FIG. 50, and if FIGS. 47-50 are compared to each other, the way of the running (i.e. the routing) of the release threads 40*a*, 40*b* between the states of being outside the threading grooves 22*a*, 22*b* and going to the threading grooves 22*a*, 22*b* under the bridge element 24 can be observed.

Moreover, FIGS. 47-50 illustrate the arrangement of gastric tube 13 (how it goes from the centre to the one of the inner channels of the tube portion 14). Furthermore, the puller portion 47 is also observable in many of these figures, as bent from the end of the main part of the cover element 82 to the appropriate inner channel of the tube portion 14. The folding of the annular cushion wings 85' can be observed also in these cross-sections.

In FIG. 47 the connection projections 54 can also be observed, both in the cross-section and—according to the view—the continuation of these can be seen.

Figure 51:
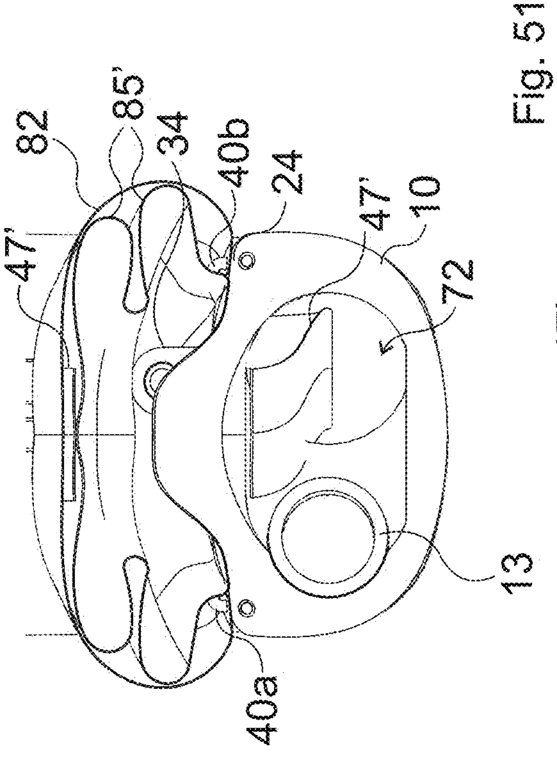
Figure 52:
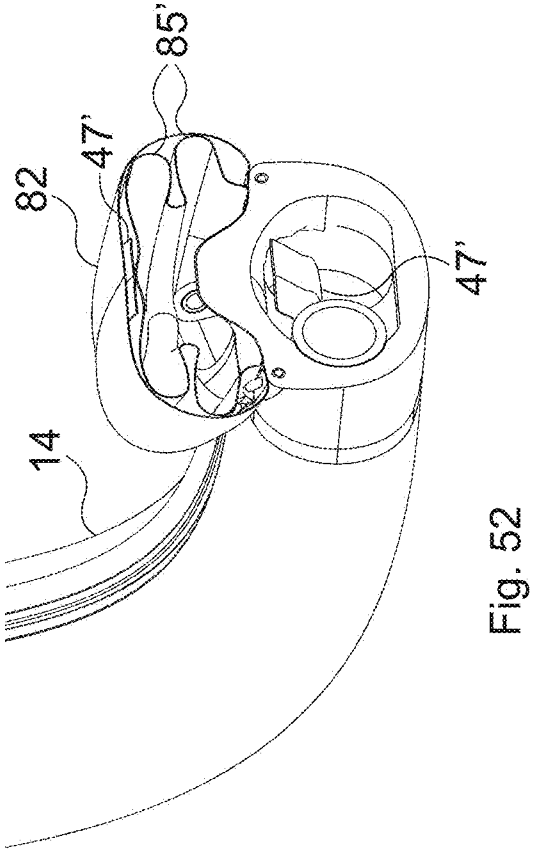

A further cross-section of the head portion 10 being almost at the tube portion 14 can be observed in FIGS. 51-52. These figures correspond to the same cross-section showing that the gastric tube 13 has reached the respective inner channel of the tube portion 14. It is also illustrated that the puller portion 47 of the cover element is just sectioned here since two pieces 47' of it can be observed in the cross-section.

Furthermore, the cross-sections of FIGS. 51-52 go through bridge elements 24, and it can be seen that the release threads 40*a*, 40*b* just go down from between the cover element 82 and the annular cushion 85 at the bridge elements 24.

Yet further, the inflation inlet part 34 can also be observed in FIGS. 51-54 and FIGS. 51-52 show the annular cushion wings 85' in this cross-section.

Figure 53:
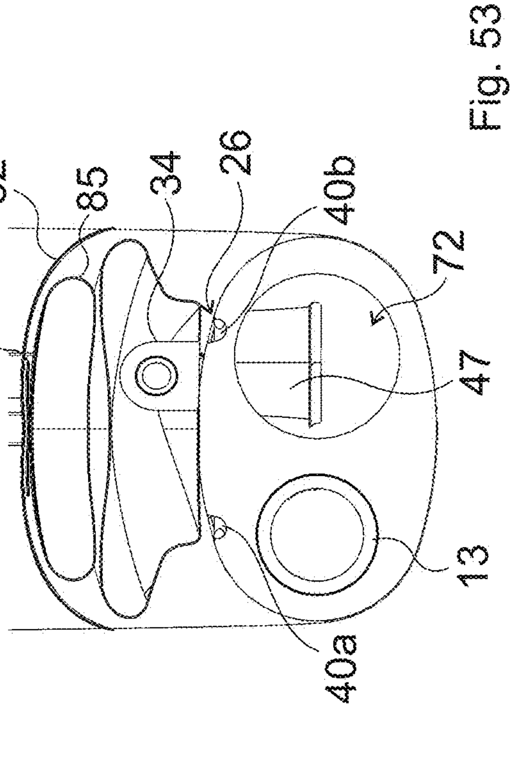

The last cross-section of the second embodiment of the laryngeal mask is shown in FIGS. 53-54. This cross-section is taken just at the start of the tube portion 14 (i.e. where the head portion 10 and the tube portion 14 is connected to each other; these are preferably moulded together as touched upon above, so here is the boundary between two components forming preferably a single part; thus, this is the preferred meaning of that these are connected to each other).

Similarly to FIGS. 31-32, this cross-section—being the same in FIGS. 53 and 54—illustrate that the inner channels of the tube portion. In the first inner channel 44 the gastric tube is connected into, while in the second inner channel 46, the puller portion 47 is inserted (two section parts of puller portion 47 can be observed also in these figures).

Furthermore, it can be observed also in FIGS. 53 and 54 that this portion of the release elements 40*a*, 40*b* run in threading groove pieces 26. In particular in FIG. 54 it is illustrated further that the threading groove pieces 26 go to the same channel for leading further the release threads 40*a*, 40*b* (cf. FIGS. 34-35 where these go together, preferably in a thread channel).

In FIGS. 53 and 54 the end part of the cover element 82 can also be observed, as well as also the end part of annular cushion 85.

In FIG. 55, the inflated state of laryngeal mask can be observed. In the details of this state, there is no difference between the first and second embodiment, because in this state the annular cushion is not packed (rolled up or folded according to the two embodiments). Thus, it has been chosen to denote the annular cushion 25 in FIG. 55, as well as in FIG. 56 showing a longitudinal cross-section of the laryngeal mask, cutting the gastric tube 13 into halves at the head distal end.

In FIGS. 55-56, many details of the inflated state can be observed. FIG. 55 shows a cross-section in which the insertion places 60 near the gastric tube 13 can be observed, into which the release threads 40*a*, 40*b* have been inserted in the uninflated state. Naturally, in the inflated state of FIG. 55, in which we can watch the inner side of the annular cushion, the release threads 40*a*, 40*b* have been removed, and also the threading grooves 22 cannot be observed, since these latter are covered by the inflated annular cushion 25 (the threading grooves 22 are formed in the head portion 10 in such a part, which will be covered by the inflated annular cushion 25; it is noted that the cover element 12 has been inserted between the material of the annular cushion 25 and those part of the head portion 10 in which the threading grooves 22 are formed).

Furthermore, according to the inflated state, the collar 29 of the head portion 10, as well as the reception recesses 15*a*, 15*b* of both sides formed between the main part of the head portion 10 and the collar 29 are clearly visible in this view. The visibility of these is helped by the inflated state and, therefore, also by that the material of the annular cushion 25 is not arranged in the reception recesses 15*a*, 15*b* in this state.

It is noted with emphasis with a reference to the view of FIG. 55, that a lot of space is available for the packing of material of the annular cushion 25 by the forming of the reception recesses 15*a*, 15*b* in the illustrated configuration of the head portion 10 (and also in other embodiments of the invention), between the main part of the head portion 10 and the collar 29 of the head portion 10.

In FIG. 56, the above circumscribed cross-section is shown. This cross-section cuts the gastric tube 13 (see also the gastric hole 30 denoted) since it bends from the center of the head portion 10. It is also shown in FIG. 56 that the gastric tube 13 start slightly inner than the material of the annular cushion 25 at the head distal end.

Furthermore, the view of FIG. 56 illustrates the details of the connection between the head portion 10 and the annular cushion 25 (this can be interpreted based on their reference numbers and the arrangement of the collar 29 being part of the head portion 10). Under the place of the reference number of the annular cushion 25 in the figure, it can be observed that there is a passage 57 in the inner space of the annular cushion 25 connecting other parts of the inner space thereof also at the head distal end. It is the laryngeal side with the laryngeal opening where the passage 57 is formed on the annular cushion, and therefore, there the cushion can be inflated—i.e. has an inner space—on the whole circumference (i.e. it is air-fillable on the whole circumference).

Figure 67:
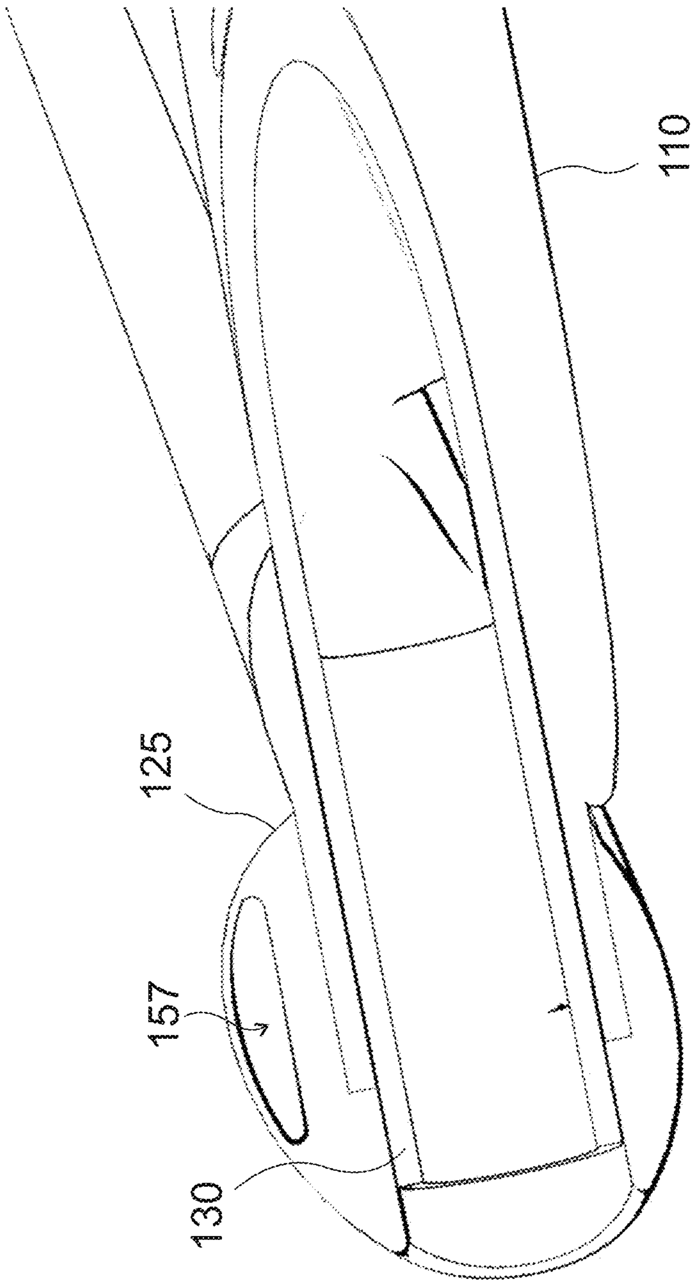
FIG. 67 shows a longitudinal sectional view of the third embodiment.
Figure 69:
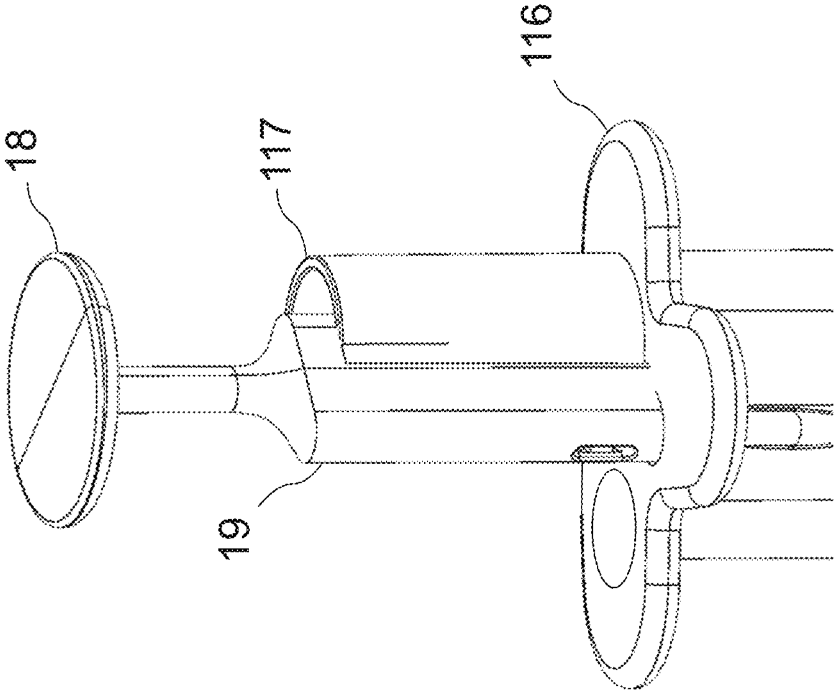
FIGS. 68-70 show the connector element of the third embodiment of the invention.
Figure 68:
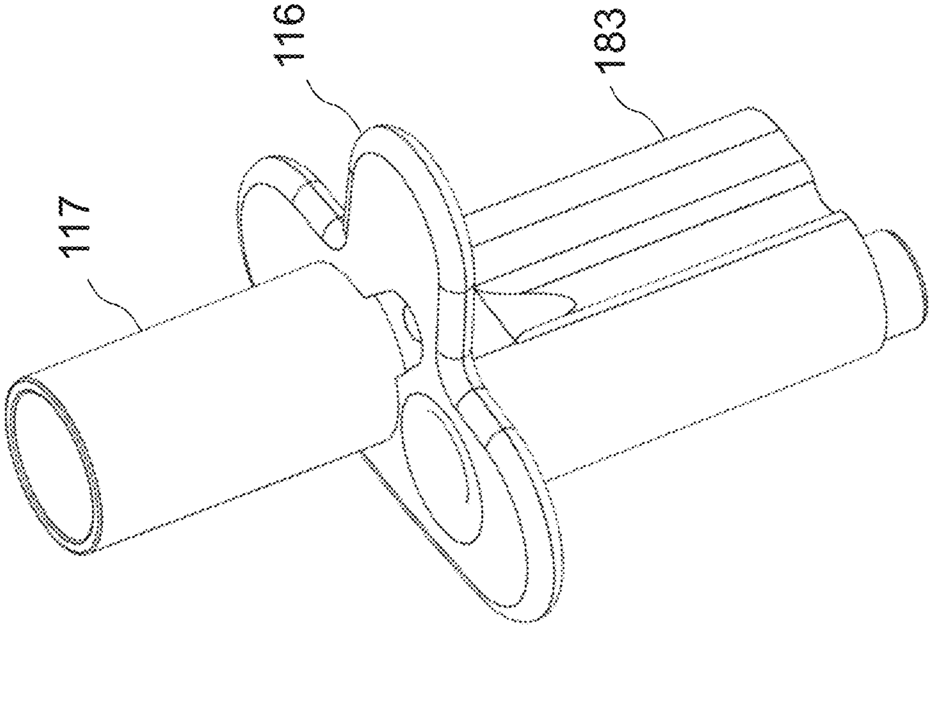
Figure 70:
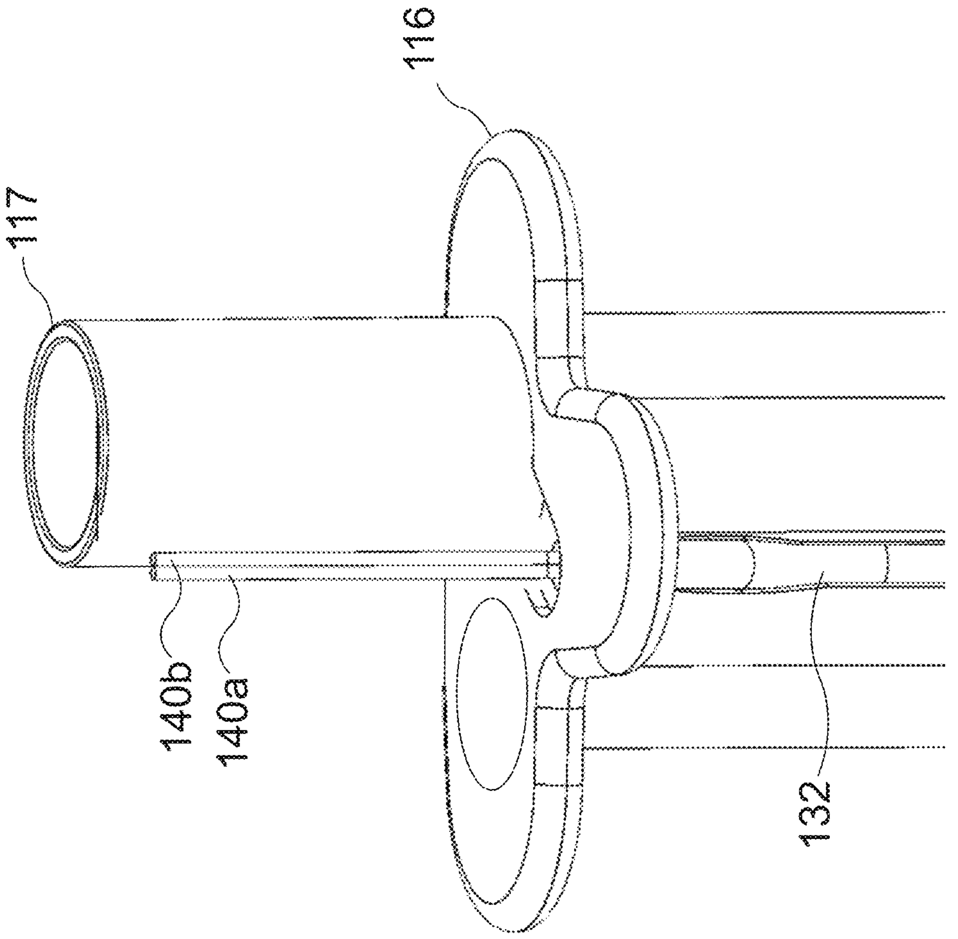

In FIGS. 57-74 the third embodiment of the laryngeal mask is illustrated, within this in FIGS. 68-70 a connector element 116 (similar to the connector element 16) is illustrated.

FIG. 57 is an upper view showing a head portion 110 and an tube portion 114 of the third embodiment, these (in particular the tube portion 114) configured very similarly to the head portion 10 and the tube portion 14 of the first embodiment. The difference between the first and second embodiment and the third embodiment can be observed in FIG. 57, namely the difference is in the configuration of threading grooves 122*a*, 122*b* (see FIG. 59 where is shown that these can be denoted commonly as threading grooves 122).

The threading grooves 122*a* and 122*b* run into each other at the head proximal end of the head portion 110, and these are in direct connection with the thread channel 132 (the latter is preferably arranged in a threading groove). The deepened threading grooves 122*a*, 122*b* has the cross-section of a turned 'D', i.e. its bottom is rounded. The bridge elements 124 (similarly to bridge elements 24 and 424; these can also be called anchors) are in the plane of the respective surface of the head portion 110, do not protrude.

In the embodiment shown in FIG. 57 three bridge elements 124 are arranged on each side of the laryngeal opening as threading elements (the bridge elements 24 of the first and second embodiments are arranged similarly), namely one close to the head distal end, where the distal tip 145 starts, one at the middle of this side of the head portion, and one close to the head proximal end, approximately in the line of the head proximal end of the collar.

If FIG. 57 is compared to FIG. 9A, it can be observed that bridge elements 124 are arranged similarly as the bridge elements 24 of the first embodiment, but the third embodiment do not comprise threading groove piece 26, but instead of its threading grooves 122 continues along the edge of the head portion 110 until their junction is reached (threading grooves 122*a* and 122*b* go into each other) at a thread channel 132. This can be used in other embodiments also: the head portion is considered to have an end at the tube portion and if this is considered, it can be said that the threading grooves 122 go tangential direction in the head portion 110 (the head portion preferably has an ovoid shape in all embodiments, which shape has two special points, these are called head distal and proximal ends). It can be observed in FIG. 57 that the threading grooves 122 run similarly as the collar 143 from the upper view; the threading grooves 122 run closer to the collar 143 at the distal tip 145 and farther from the collar 143 at the head proximal end of the head portion 110.

In FIG. 57 release threads 140*a*, 140*b* are shown as well as their ends at the outer end of tube portion 114. FIG. 57 shows also an inflation tube groove 134 for an inflation tube (cf. with e.g. FIG. 1, where the inflation tube 20 is arranged). At the outer end of the tube 114 a first inner channel 144 and a second inner channel 146 can be observed, these have the same roles as the inner channels 44, 46 in FIG. 9A. It is noted that in FIGS. 57-60 the main part of the laryngeal mask is shown without the annular cushion similarly to some figures of the previous embodiments.

Thus, in the first, second and third embodiments, preferably, at least one thread channel is formed along the tube portion (inside or outside) or connected to the tube portion along the tube portion, and the first release thread and the second release thread are arranged in the at least one thread channel. In these embodiments, the release threads are arranged in a common thread channel, but the respective released threads may also be arranged in separate thread channels also. In this respect, we refer to FIGS. 88A-88E, in particular FIG. 88E, where two thread channels are arranged for the two release threads. Accordingly, at least one thread channel means that one or—according to the number of the release threads—two.

Figure 58:
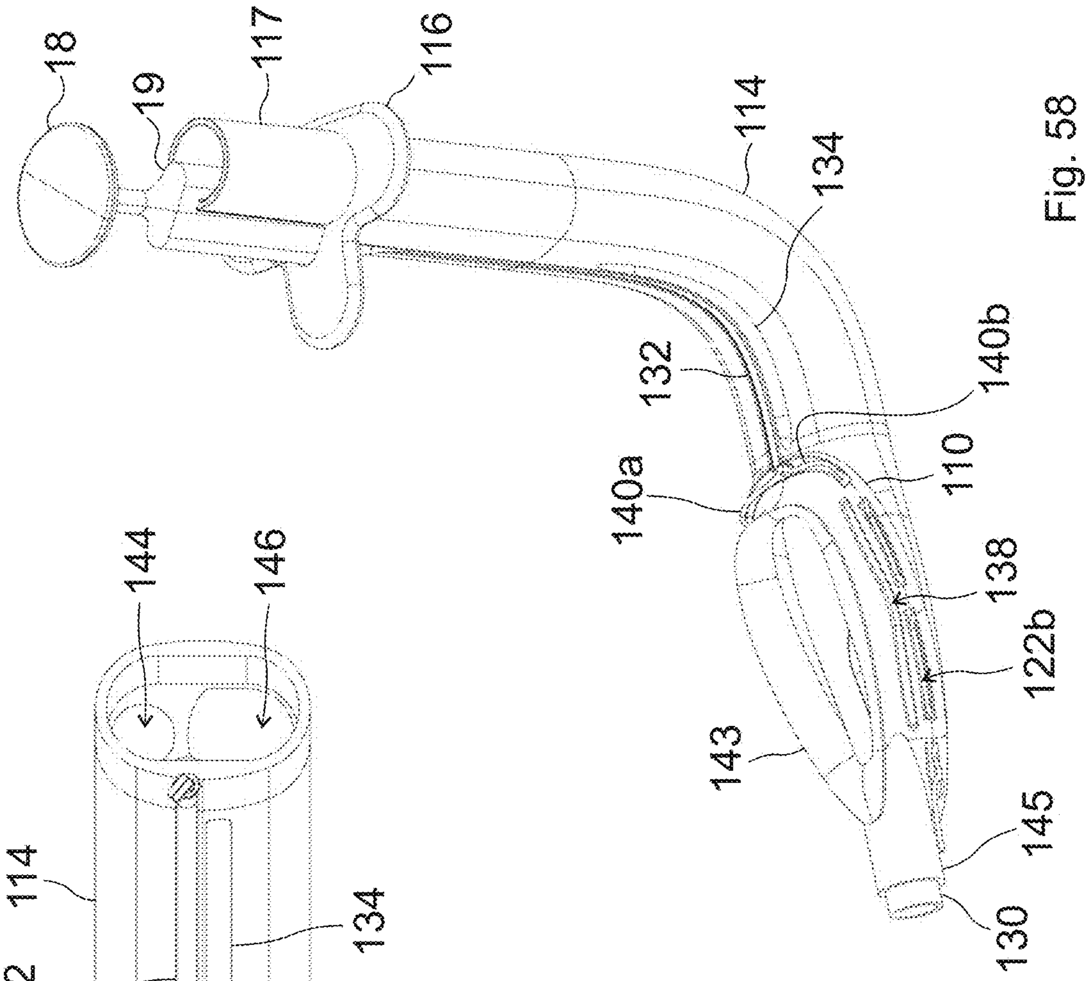
FIG. 58 shows the third embodiment of FIG. 57 from a spatial view with release threads.

In FIG. 58, the third embodiment of the laryngeal mask can be observed in a further spatial view. In this view the release threads 140*a*, 140*b* are also shown as if the annular cushion would be arranged, as if it would be in the assembled state (similarly to some of the above views). In FIG. 58 also a gastric tube 130 is denoted, as well as a distal tip 145. Furthermore, in FIG. 58 a connection groove 138 is shown, which differs from the connection groove 38 in that this is not a straight groove but the connection groove 138 has a slight bending. For the connection grooves 138 see also FIG. 57.

In FIG. 58, furthermore, the connector element 116 can be observed with an end tube 117 and the pullable end element 19 having the handle 18.

Figure 60:
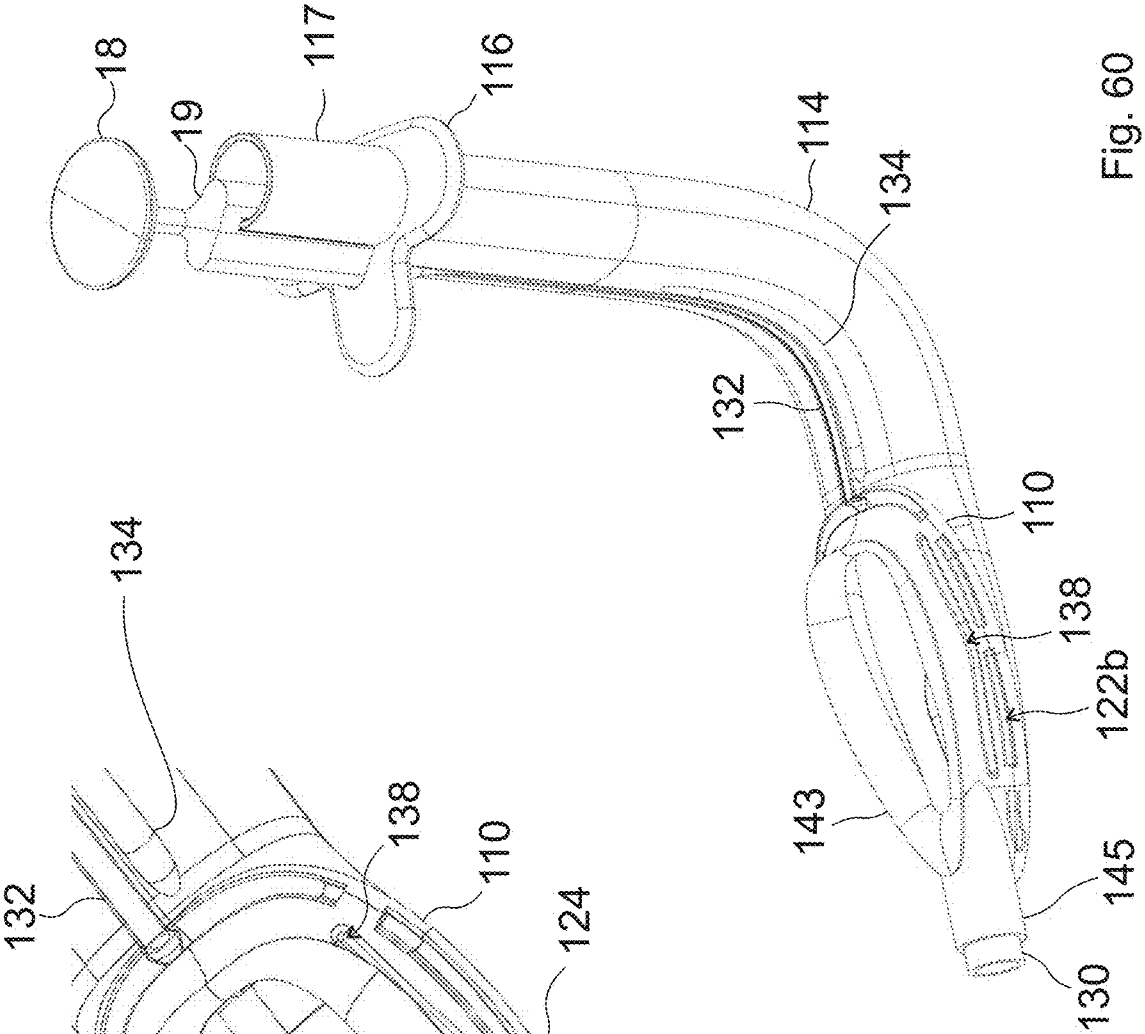
FIG. 60 shows the third embodiment of the invention from a spatial view without release threads.
Figure 59:
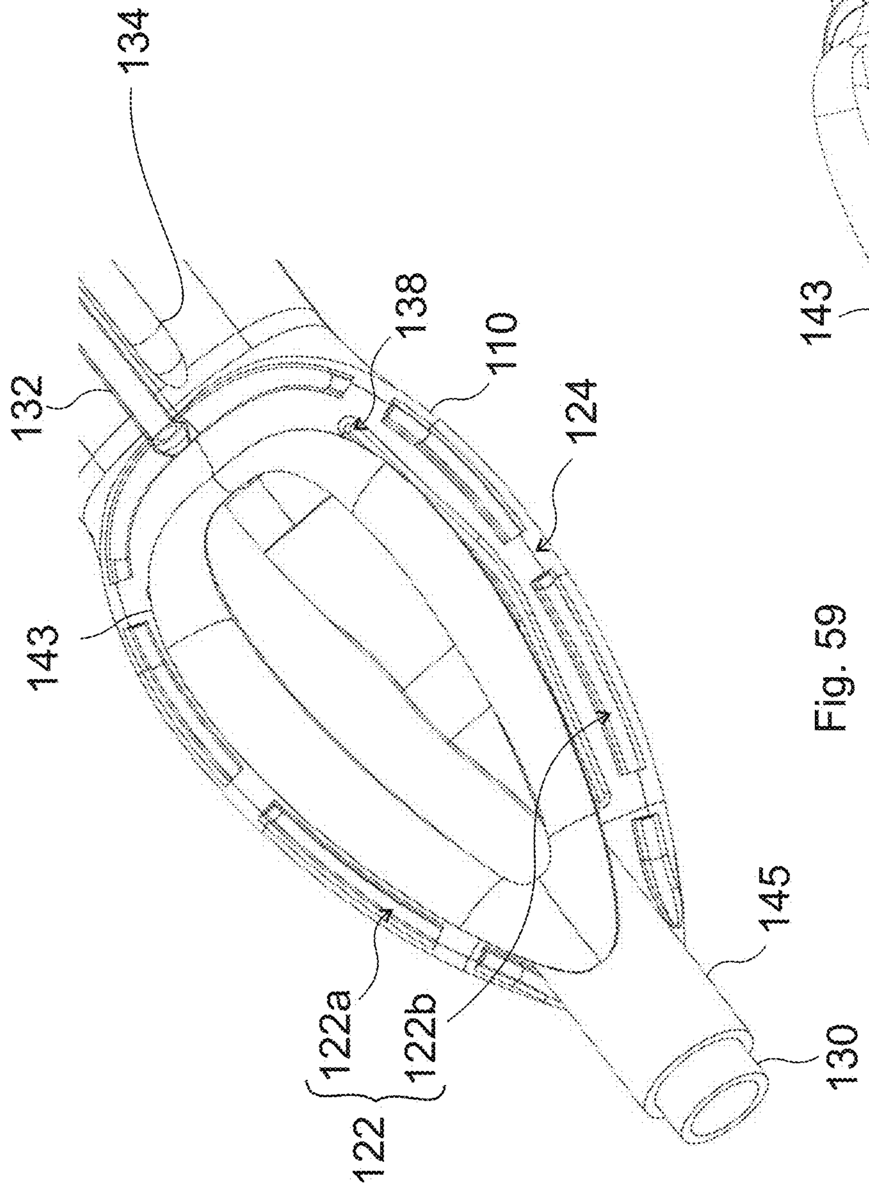
FIG. 59 shows the head portion of the third embodiment of the invention from a spatial view without annular cushion.

In FIGS. 59-60 the third embodiment of the laryngeal mask is illustrated without the release threads 140*a*, 140*b* from an upper view and in a similar view as FIG. 58, respectively.

In FIG. 59 the threading grooves 122*a*, 122*b* (as well as their common notation as threading grooves 122) as well as the thread channel 132 can be better observed because of the removal of the release threads 140*a*, 104*b*, see also the opening of the thread channel 132 at the junction of the threading grooves 122. Furthermore, the connection groove 138 can be observed from a further view; this view shows that its configuration has a similar—i.e. slightly bent, curved-line as the line of the collar 143 above it. In FIG. 60 similar details can be observed.

Figure 62:
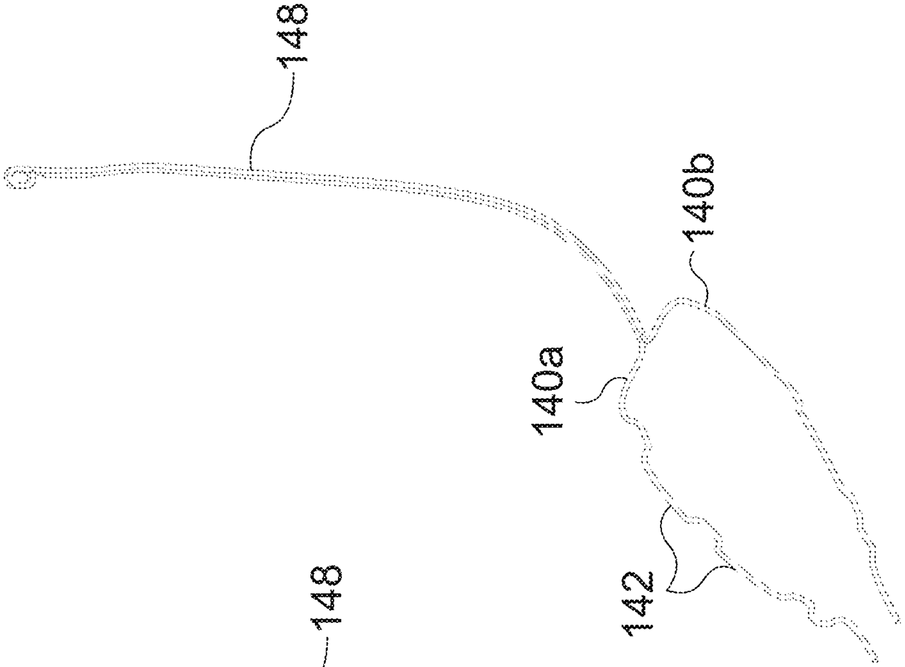
FIGS. 61 and 62 show a single release thread and release threads, respectively.
Figure 61:
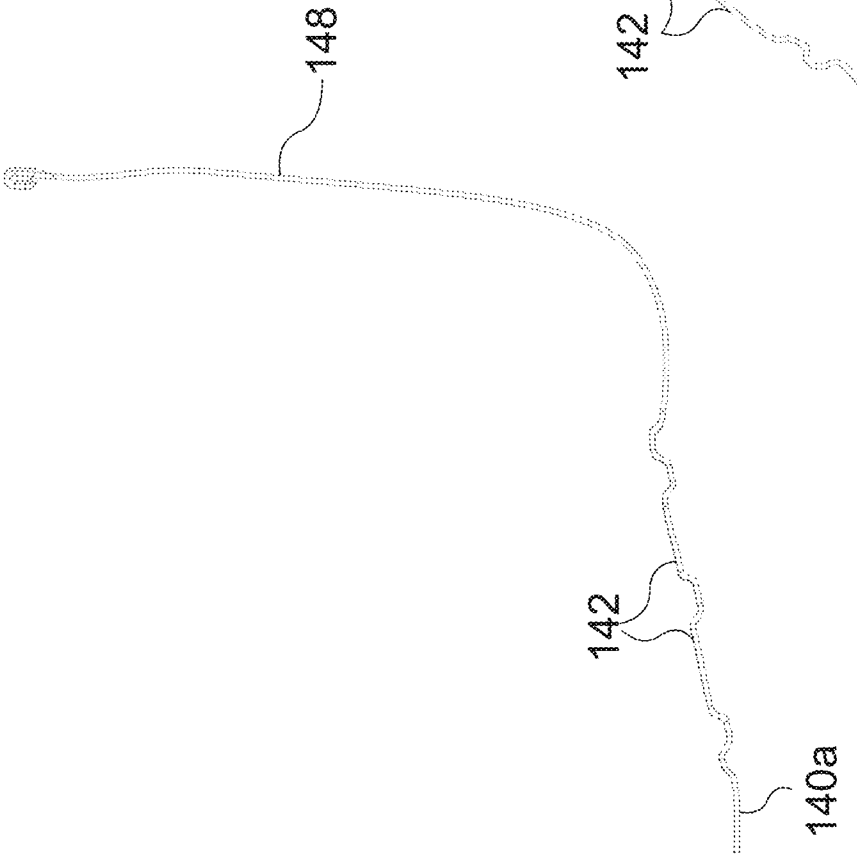

In FIGS. 61 and 62 the release thread 140*a* and both release threads 140*a*, 140*b* are illustrated, respectively. The release threads 140*a*, 140*b* are illustrated as if these would be in the assemble state as bends 142 are illustrated in FIG. 61 (these figures can be compared to FIGS. 6-7, see also a first puller portion 148).

Figure 63:
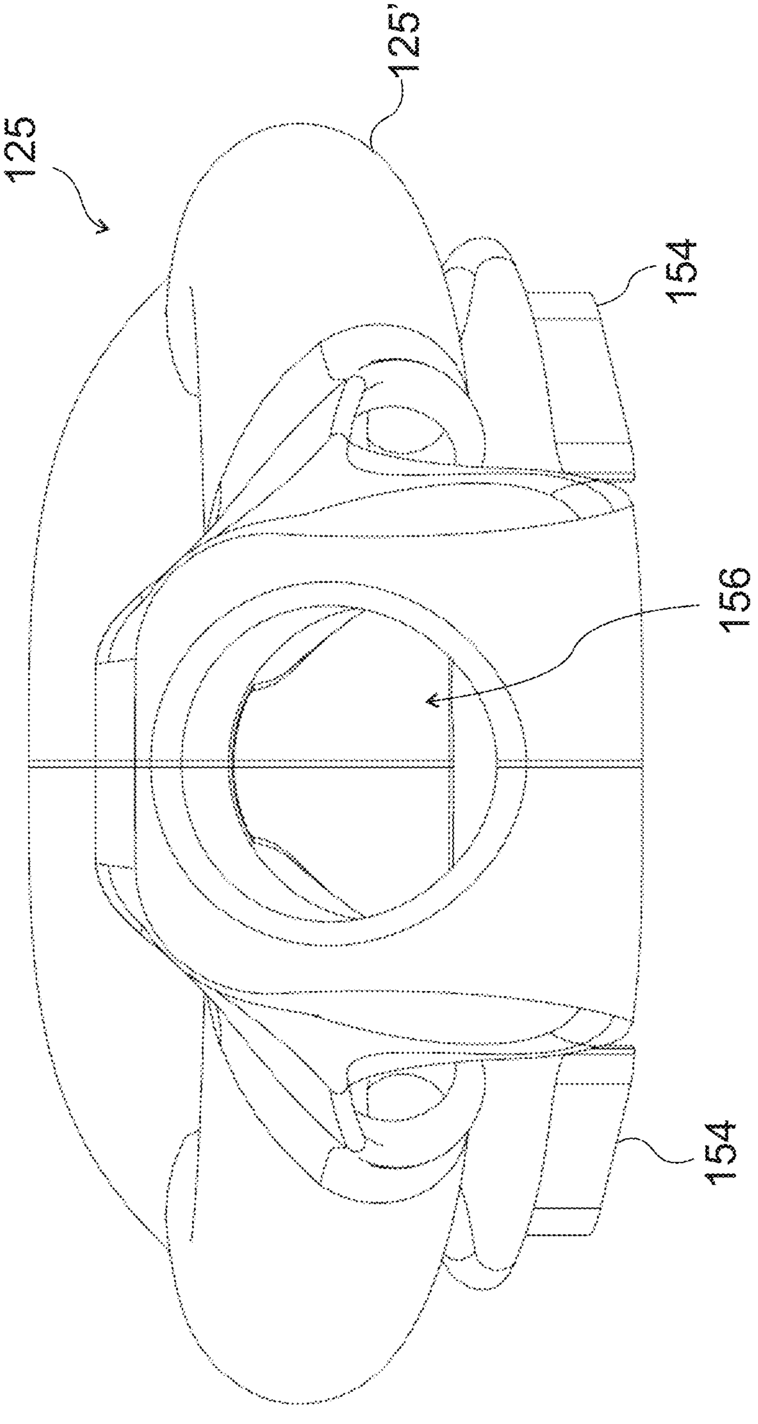
FIG. 63 shows the annular cushion of the third embodiment in a first variant.
Figure 66:
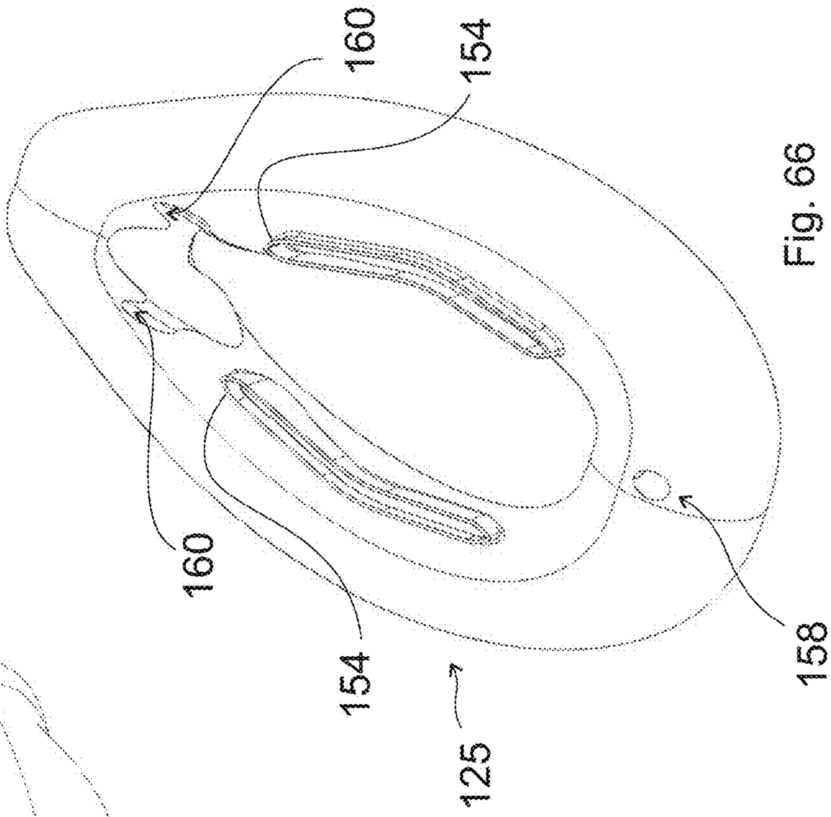
FIG. 66 shows the annular cushion of the third embodiment in an inflated state.
Figure 65:
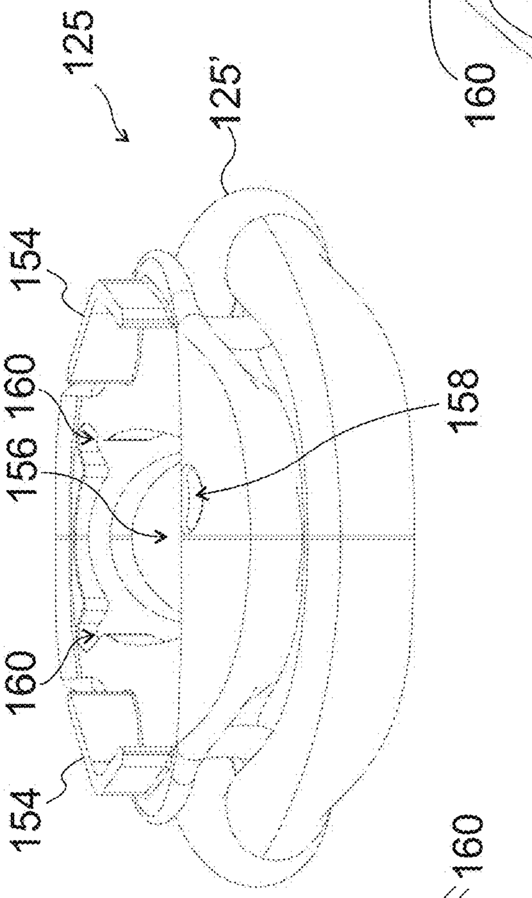
FIG. 65 shows the annular cushion of the third embodiment in the first variant from a further view.

In FIGS. 63-66 an annular cushion 125 of the third embodiment of the laryngeal mask is illustrated in different views and in two variations, since FIGS. 63 and 65 show a rolled-up configuration for the annular cushion 125, but FIG. 64 shows the annular cushion 125 in a folded configuration, as well as FIG. 66 shows the annular cushion in an inflated state. Regarding these, it is noted that FIGS. 63-65 show the annular cushion 125 in a packed state as if these would be in the assembled laryngeal mask covered by a cover element.

FIG. 63 shows the following details of the annular cushion 125, namely rolled-up annular cushion wings 125', as well as a gastric hole 156 for letting through the gastric tube 130 (its end arranged therein). Furthermore, connection projections 154 are also observable is this view (for the latter see the further figures).

In FIG. 64 the annular cushion 125 is shown in a view from its bottom. Thus in FIG. 64 the connection projections 154 can be observed, these have a configuration according to which these can be inserted to connection grooves 138 shown in FIGS. 57-60.

Furthermore, in FIG. 64 insertion places 160 are denoted (cf. with insertion places 60 in FIG. 38). Yet further an inflation hole 158 is also shown in these figures. It is denoted in the figures that annular cushion 125 encompasses (surrounds) a cushion opening 162.

FIG. 65 shows also the variant of FIG. 63 with rolled-up annular cushion wings 125' in a further view with details shown in FIG. 64 having similar details being independent from the configuration of the annular cushion wings.

In FIG. 66 the annular cushion 125 is shown in an inflated state. In this view the insertion places 160 can be observed well. FIG. 66 shows configuration details also for connection projections 154, which have also the same configuration everywhere but in FIGS. 64-65 the details—i.e. the inner structure—thereof are not illustrated.

FIG. 67 show a similar section as FIG. 56 but for the third embodiment, showing also a passage 157 for the inner space of the annular cushion 125 at the head distal end. Comparing passages 57 and 157 to each other, it can be seen that the cross-section of the passage 57 at the head distal end (i.e. this is here the cross-section of the annular cushion) is larger than the cross-section of the passage 157. Moreover, the passage 57 is more shifted in the direction of the head distal end which helps to have a better sealing of the annular cushion in use with the embodiment having the passage 57.

FIGS. 56 and 67 show that preferable the material of the annular cushion extends further out than the material of the head portion in order to facilitate avoid traumatic effects and have better seal.

FIGS. 68-70 illustrate the connector element 116, which can be inserted to the end of the tube portion 114. FIG. 68 shows the connector element 116 as a whole as an insertable component having an insertable part 183 (cf. with FIG. 57, in which the inner channels 144, 146 begin a little bit lower within the tube portion 114 in that view in order that the connector element 116 can be inserted into the insertion space formed in this way at the end of the tube portion 114).

FIG. 69 shows the connector element 116 with the pullable end element 19 inserted onto the end tube 117.

In FIG. 70 the pullable end element 19 is removed, but the release threads 140*a*, 140*b* inserted into the pullable end element 19 in the previous view are illustrated, illustrating that the release threads 140*a*, 140*b* come out from the thread channel 132 going through a thread hole which can be observed in FIG. 15 in the connector element 16 (see also FIG. 68). The release threads 140*a*, 140*b* are illustrated with free ends but this is only for illustration: these can be separate threads but also part of a single thread.

The connector element 116 in FIGS. 68-70 has a similar configuration to the connector element 16 illustrated in FIGS. 14-16B, the same details written above in connection FIGS. 14-16B are applicable also to FIGS. 68-70.

In FIGS. 71-79 a fourth embodiment of the laryngeal mask is illustrated.

It is noted in connection with the previous embodiments (namely, first, second and third embodiments, and preferably in fifth, sixth and seventh embodiment) that in those, preferably, a closed-type annular cushion is utilized which is connected onto the head portion as a unit (we refer to FIGS. 36-38 and FIGS. 63-66). This means that the inner space (i.e. the space to be inflated) is substantially closed (substantially means that it is closed except the inflation hole), in other words, in these embodiments we have a self-defined annular cushion: the side of it is connected to the corresponding part of the head portion, preferably, into the reception recess part, on the portions where these are applied beside the laryngeal opening. This type of annular cushion can be separately manufactured, and it is considered airtight in itself (when the inflation hole is closed). For gluing, i.e. adhesion of the annular cushion to the head portion, see above. As an advantage, there is no need for applying for the closed-type annular cushion adhesion for in order to seal the inner space of the annular cushion since it is already closed in the above meaning.

Alternatively, in this (namely, fourth embodiment) and other conceivable embodiments an opened-type annular cushion is utilized, in other words, half-closed (it has a shape of a large C letter in its cross-section, where the ends of the C-shape are to be connected to the head portion), which is to be connected—for example by gluing, i.e. adhesion—preferably to the edge of the collar and to a portion close to edge of the head portion so that not to hinder the usage of the loops or threading groove, since these latter are for fixing the cover element which is intended to encompass the annular cushion at these sections. The annular cushion is to be connected to the head portion-beside the connection mentioned above—at the head proximal end also preferably by gluing (e.g. in the present embodiment it is connected to annular cushion holding configuration 222).

Figure 72:
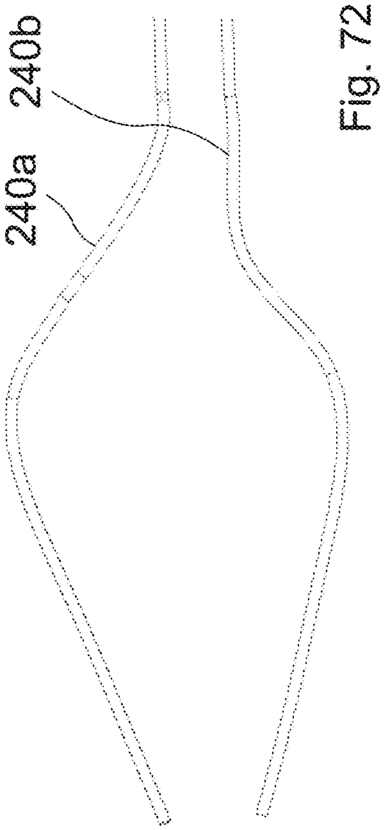
FIG. 72 illustrates the release threads of the fourth embodiment.
Figure 71:
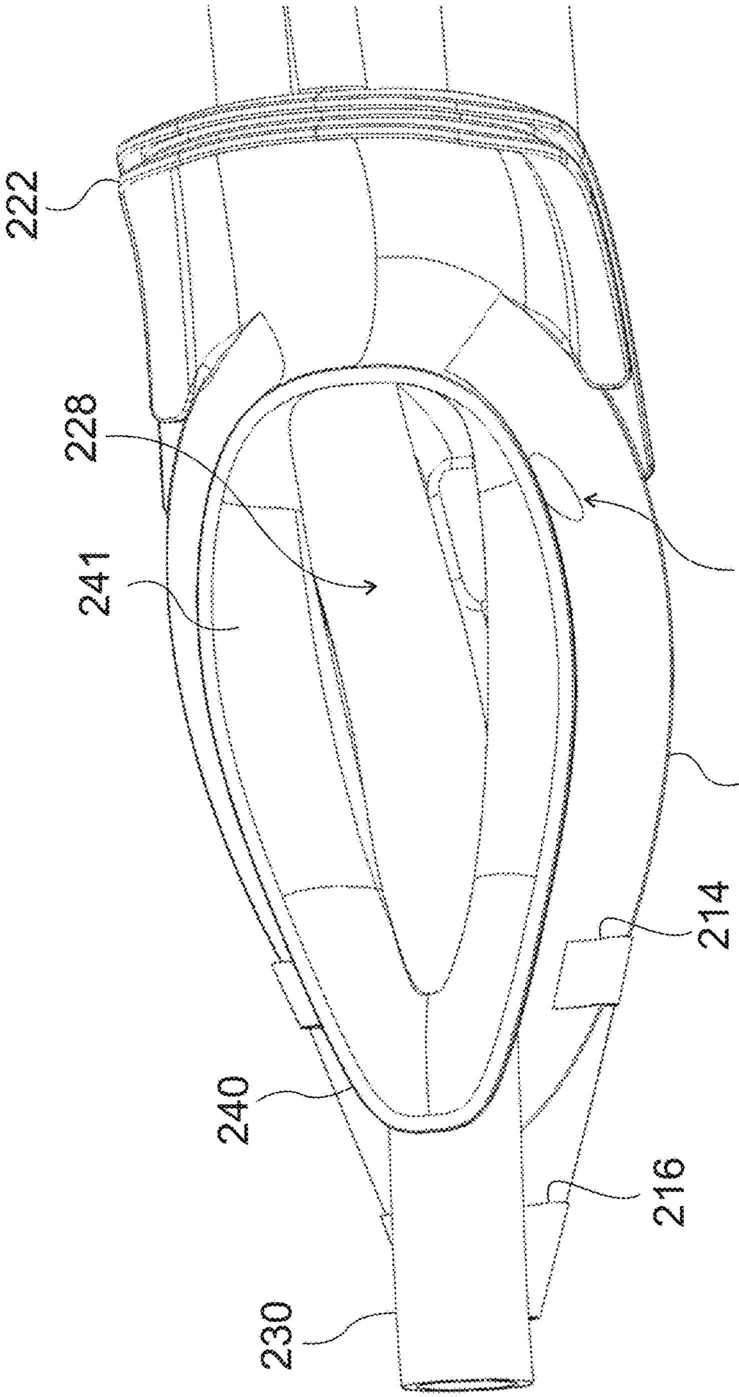
FIG. 71 illustrates a fourth embodiment of the invention without the annular cushion in a spatial view.

FIGS. 71 and 72 together show that in this embodiment the running of release threads 240*a*, 240*b* are determined in a different way than in the previous embodiments. In the fourth embodiment of FIG. 71 the release thread 240*b* will enter in an entering hole 213, pass through a first loop 214 and inserted into a second loop 216. The release thread 240*a* runs in a similar way in the other side of the head portion 210 (behind the collar in the figure). Accordingly, with the help of this fixing of the release elements 240*a*, 240*b* the cover element (not illustrated) will be held in its place while packing the annular cushion element.

It is noted that with the help of the loops 214, 216—similarly to the embodiments with the corresponding threading groove—the cover element is fixed within the reception recess, i.e. the cover element does not cover the head portion edge, i.e. does not get onto the other side of the head portion (but it is connected to its side with the laryngeal opening).

In FIG. 71 a distal tip 230 is shown, as well as a collar 241 is illustrated. Furthermore FIG. 71 shows annular cushion holding configuration 222 which have a double wall to insert the material of the annular cushion between these.

According to the above, in the present embodiment two loops (namely, loops 214 and 216) are arranged at both side of the laryngeal opening as threading elements. One of the loops, namely the loop 216 is arranged at the distal tip 230, into the loop 216, the release threads 240*a*, 240*b* are only inserted and do not pass through. The other loop, namely the loop 214 is also closer to the head distal end, approximately where the distal tip 230 starts.

Figure 73:
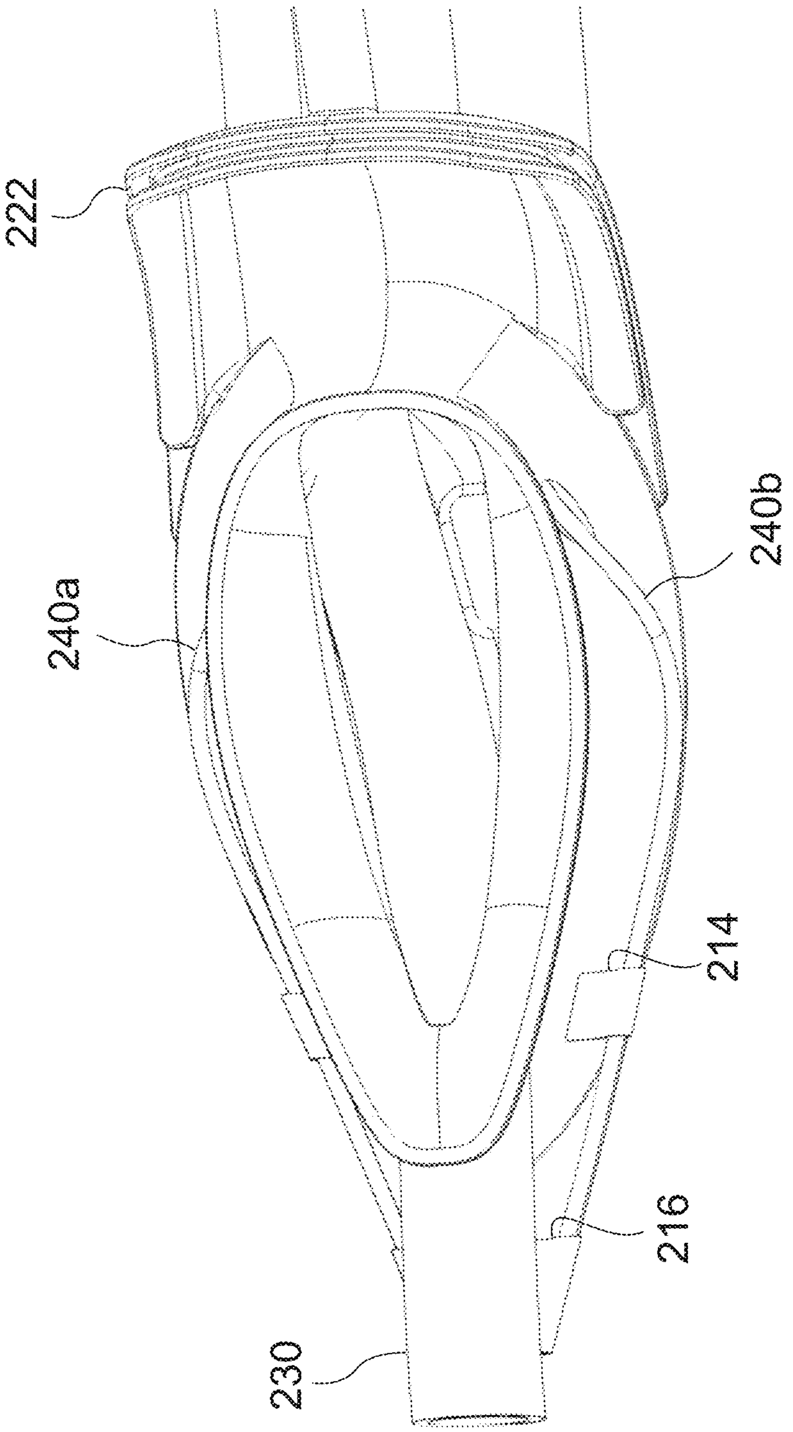
FIG. 73 shows the fourth embodiment of FIG. 71 with release threads from spatial view.

FIG. 73 illustrates the arrangement of the release threads 240*a*, 240*b* as discussed above.

Figure 74:
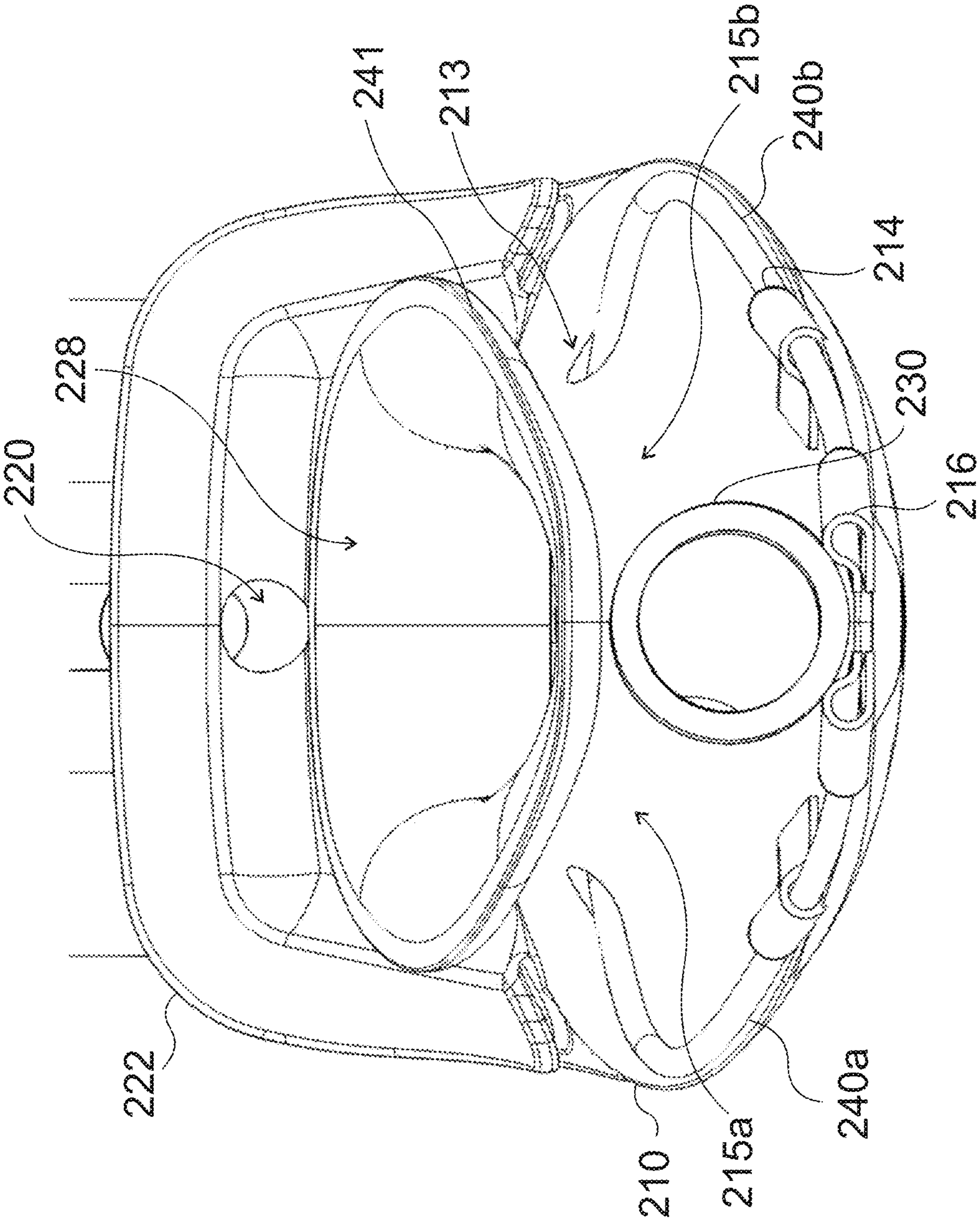
FIG. 74 shows the fourth embodiment of the invention from a front view without the annular cushion and with release threads.

FIG. 74 shows a front view of this embodiment in which the arrangement of the release threads 240*a*, 240*b* can be observed. It is noted that the release threads 240*a*, 240*b*—as mentioned above—are arranged in the assembled state of the laryngeal mask, i.e. when an annular cushion and a cover element, which latter is connected the head portion 210 by the help of release threads 240*a*, 240*b*, but the annular cushion and the cover element have been removed from FIGS. 73 and 74 for illustrative reasons.

In FIG. 74 also the distal tip 230 can be observed, and that the collar 241 forms with the head portion 10 well-defined reception recesses for accommodating the material of the annular cushion applied in this embodiment.

Furthermore, it is illustrated in FIG. 74 that an input hole 220 for introducing air into the annular cushion is formed on the cushion holding configuration 222. Since the arrangement of the release threads 240*a*, 240*b* is shown in FIG. 74, also the configuration of the loops 214, 216 is illustrated in this embodiment. Also, a first reception recess 215*a* and a second reception recess 215*b* can be observed in FIG. 74, as well as see in FIGS. 71 and 74 a laryngeal opening 228 of this embodiment.

Figure 75:
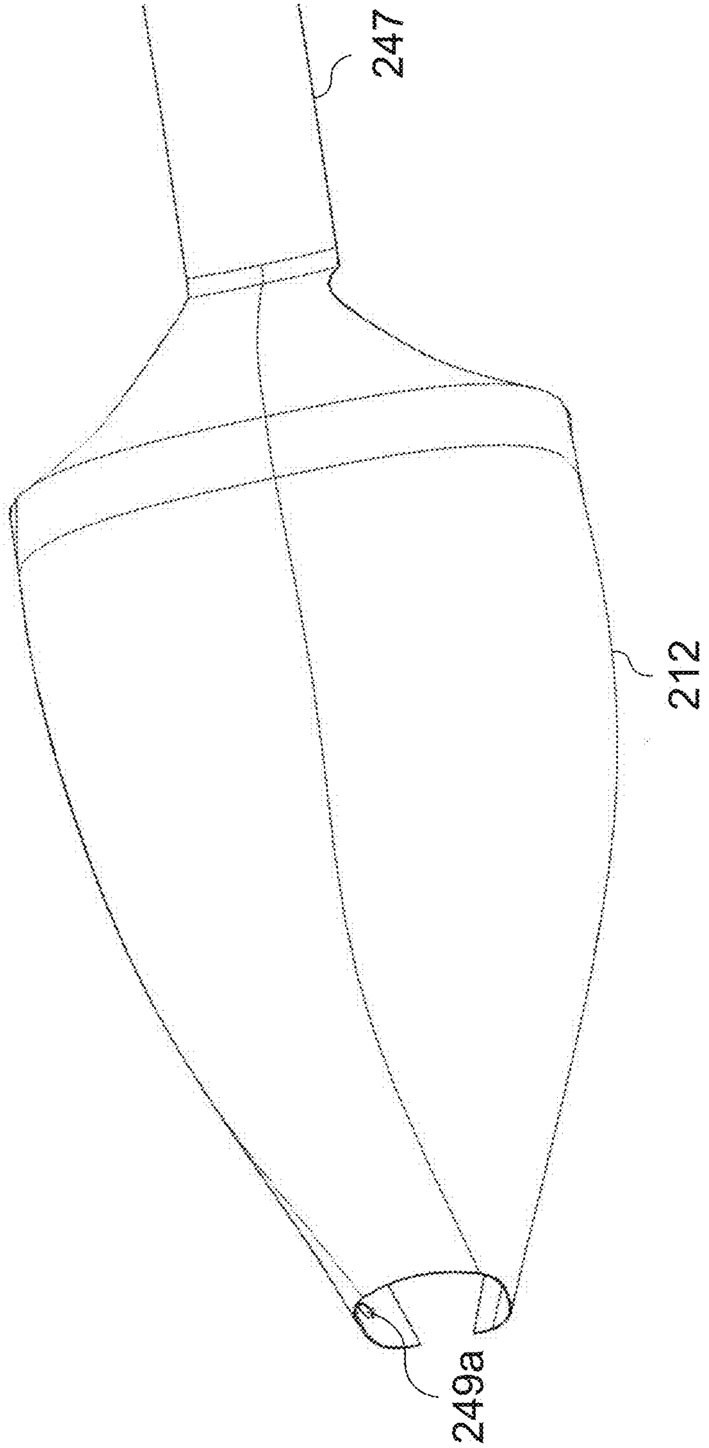
FIGS. 75 and 76 illustrate the cover element of the fourth embodiment of the invention in different views.
Figure 76:
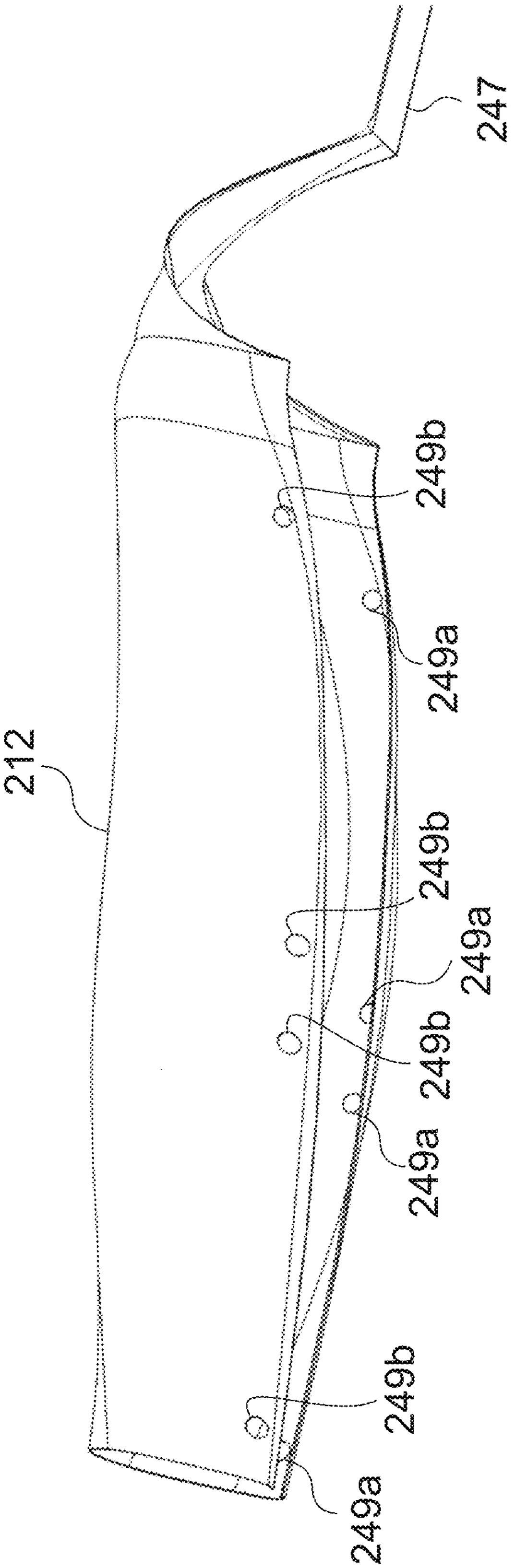

FIGS. 75-76 show a cover element 212 applicable in the fourth embodiment illustrated in FIGS. 71-74. In FIG. 75 a single threading hole 249*a* (of the first row) is observable and also a puller portion 247 connected to (the main part of) the cover element 212 is shown. In FIG. 76 a first row of threading holes 249*a* and a second row of threading holes 249*b* are illustrated on both cover element edges of the main part of the cover element 212 (cover element edges 253*a*, 253*b* are shown in FIG. 77).

Figure 79:
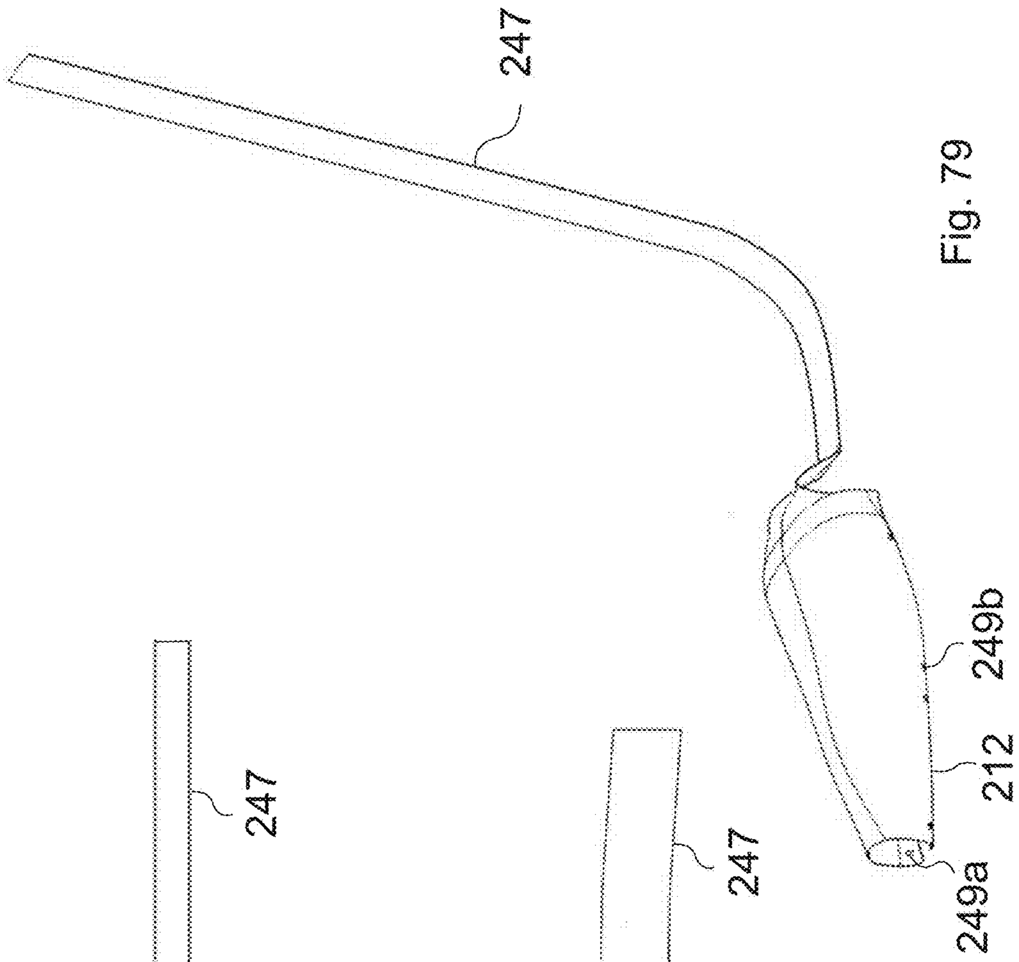
FIGS. 78 and 79 illustrate the cover element of the fourth embodiment from further views.
Figure 78:
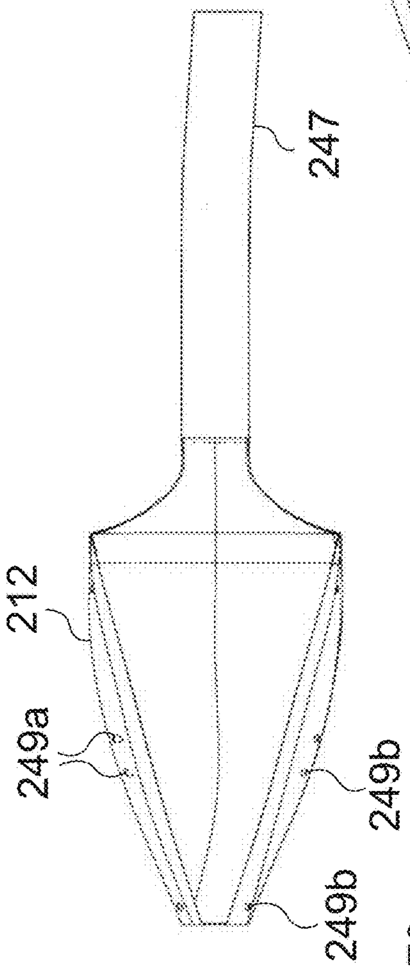

FIGS. 77-79 show further views of the cover element 212. In FIG. 77 the cover element 212 is laid out, and the threading holes 249*a* of the first row and the threading holes 249*b* of the second row, as well as a first cover element edge 253*a* and a second cover element edge 253*b* are shown in this laid out illustration. FIG. 78 shows the cover element 212 from above and FIG. 79 shows it in a spatial view illustrating its arrangement as if it would be in an assembled state (with that shapings, bends), showing the puller portion 247 in its whole length.

It is noted in connection with the fourth, fifth, sixth and seventh embodiments that in these the release threads can be led to the tube proximal end of the tube portion in the so-called airway channel (see e.g. channel 46 in FIG. 12 for such a channel), or, similarly to the first, second or third embodiments (for this the release threads have to be led from the loops or threading groove to the outside of the tube portion at its beginning), the structures shown there outside the tube portion (see e.g. thread channel 32) can be also utilized in these embodiments (see entering holes 213, 313 on the wall of the reception recess, it is the choice to where these holes are connected, where the corresponding tunnel leads to, inside or outside the tube portion). It is noted that the choice does not affect the joint pulling since in both case the first and second puller portions are led outside the device (in order to be pullable at the tube proximal end of the tube portion).

FIGS. 80-83 illustrate a fifth embodiment having a head portion 310, an tube portion 314 and a cover element 312.

In FIG. 80 the cover element 312 is placed onto the head portion only illustratively for two reasons. The first reason is that there is no annular cushion arranged in FIG. 80 for illustrative reasons, and naturally the cover element 312 should be arranged onto an annular cushion element. The second reason is that the cover element 312 is not arranged in a very exact position of it, but the exact positioning of the cover element 312 is influenced by the location of the holes at the edges of the cover element 312 and positions of the loops (of which loops a loop 317 can be observed in FIG. 80).

In FIG. 80, furthermore, a puller element 347 of the cover element 312 can be observed, which is bent and leaded to the inner channel of the tube portion 314. A gastric tube 330 is also illustrated in FIG. 80. Furthermore, in FIG. 80 the arrangement of the release threads is illustrated, namely a release thread 340*b* can be observed in FIG. 80, this comes out from an entering hole 313 and goes into the loop 317 and after that it connects the cover element 312 to the head portion 310.

Figure 81:
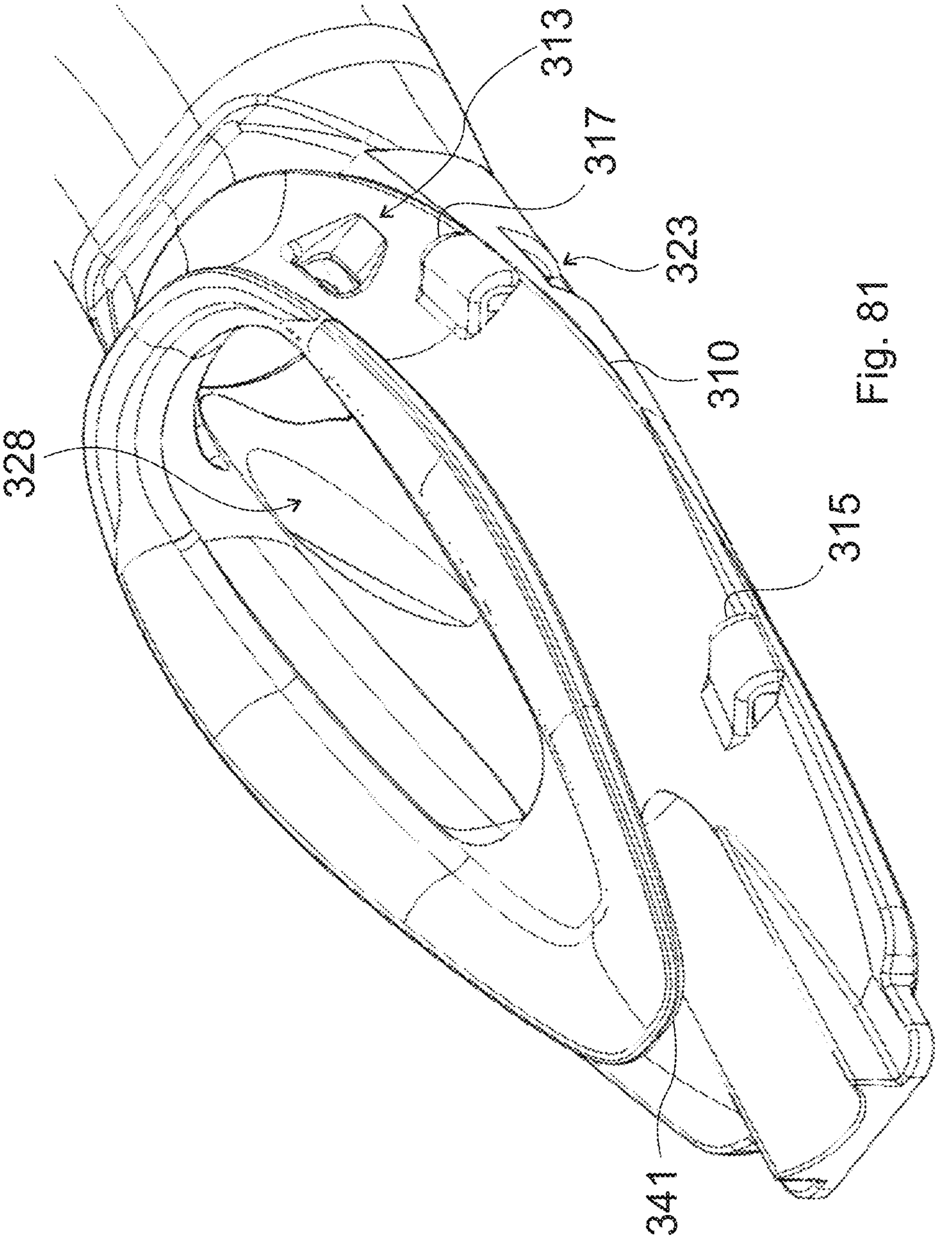
FIG. 81 shows the fifth embodiment of the invention without the annular cushion, the cover element and the release threads from a spatial view.

In FIG. 81 spatial view of the head portion 310 is shown. Because of the removal of the cover element 312, a further loop 315 can be observed, and the front configuration of the head portion 310 being at the head distal end is shown. This front configuration is formed this way to accommodate the gastric tube, as well as (see also FIG. 81) the ends of the release threads are led here. Thus, the running of the release threads can be interpreted based on FIG. 81, i.e. the release thread will come out from the hole 313, go through the loops 315 and 317 and will end at the head distal end inserted into the material of the annular cushion (we hereby also refer to FIG. 83).

In FIG. 81 furthermore a collar 341 of the head portion 310 can be observed which is configured similarly as the collars of the previous embodiments, in particular at its part being between the head distal and the proximal ends (i.e. at the reception recess). Furthermore, a cut-out 323 corresponding to the loop 317 can be observed (these require an open-bottom design for tooling). The collar 341 encompasses a laryngeal opening 328 in this embodiment.

According to FIG. 81, in this embodiment two loops (namely loops 315 and 317) are arranged on each side of the laryngeal opening as threading elements. Both of these loops are configured so that the release thread can be passed through these. In this case the release threads run on the surface of the head portion 310 (namely, the surface of the reception recess of the head portion 310), it is noted in connection with this that a respective part of the cover element is arranged between the respective part of the release thread and the surface of the head portion.

Figure 82:
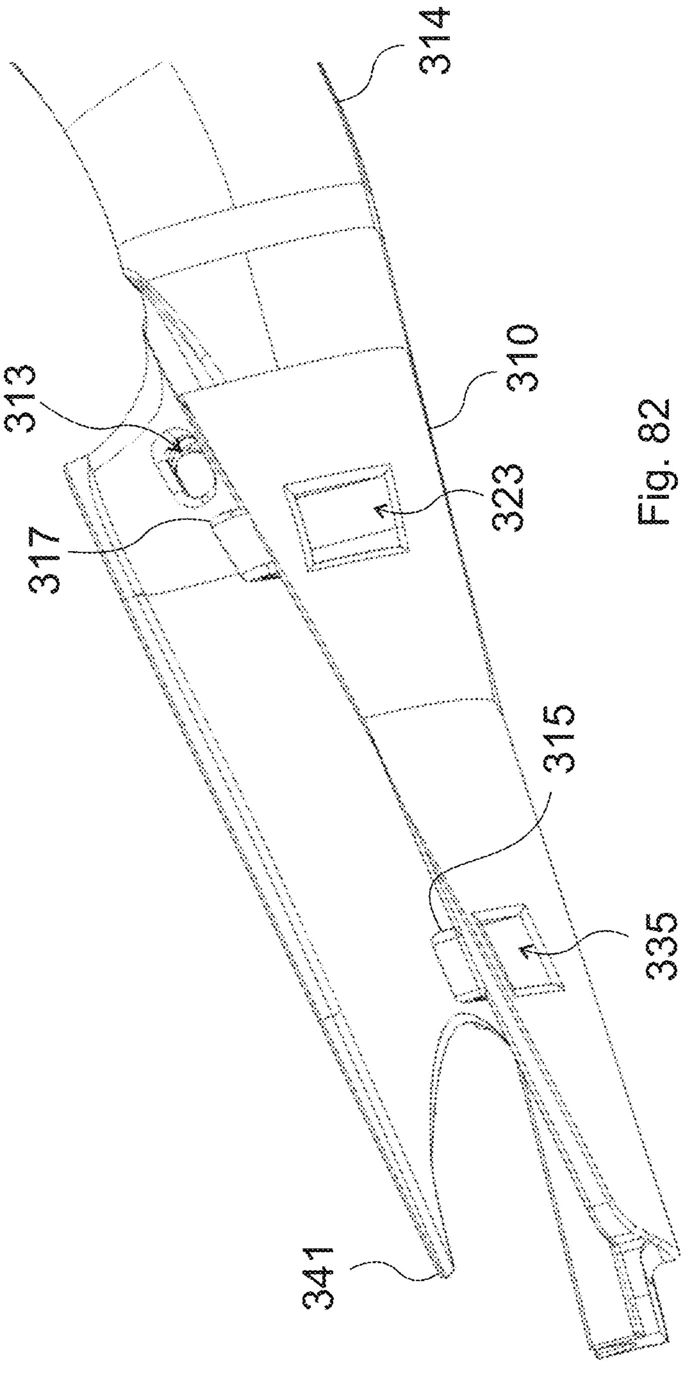
FIG. 82 shows the status shown on FIG. 81 in a side view.

FIG. 82 shows the head portion 310 of the fifth embodiment in a side view. In FIG. 82 thus the cut-out corresponding to both of the loops can be observed, i.e. the cut-out 323 for the loop 317, as well as a cut-out 335 for the loop 315. Furthermore, the hole 313 is clearly visible.

The configuration of the collar 341 shows that there is space at the head distal end for accommodating the gastric tube as well as (also in comparison with FIG. 81) that the reception recess (not denoted by reference number, since only one of the first and second reception recesses can be observed in the figures of this embodiment) is formed at the two sides of the collar and from this view it can be seen that at the head proximal end there is no reception recess portion (on that portion there is substantially no indenture, but surface around the collar is substantially only arched), but the annular cushion will be arranged simply onto the curved part of the head portion 310 there (cf. also with FIG. 81).

Figure 83:
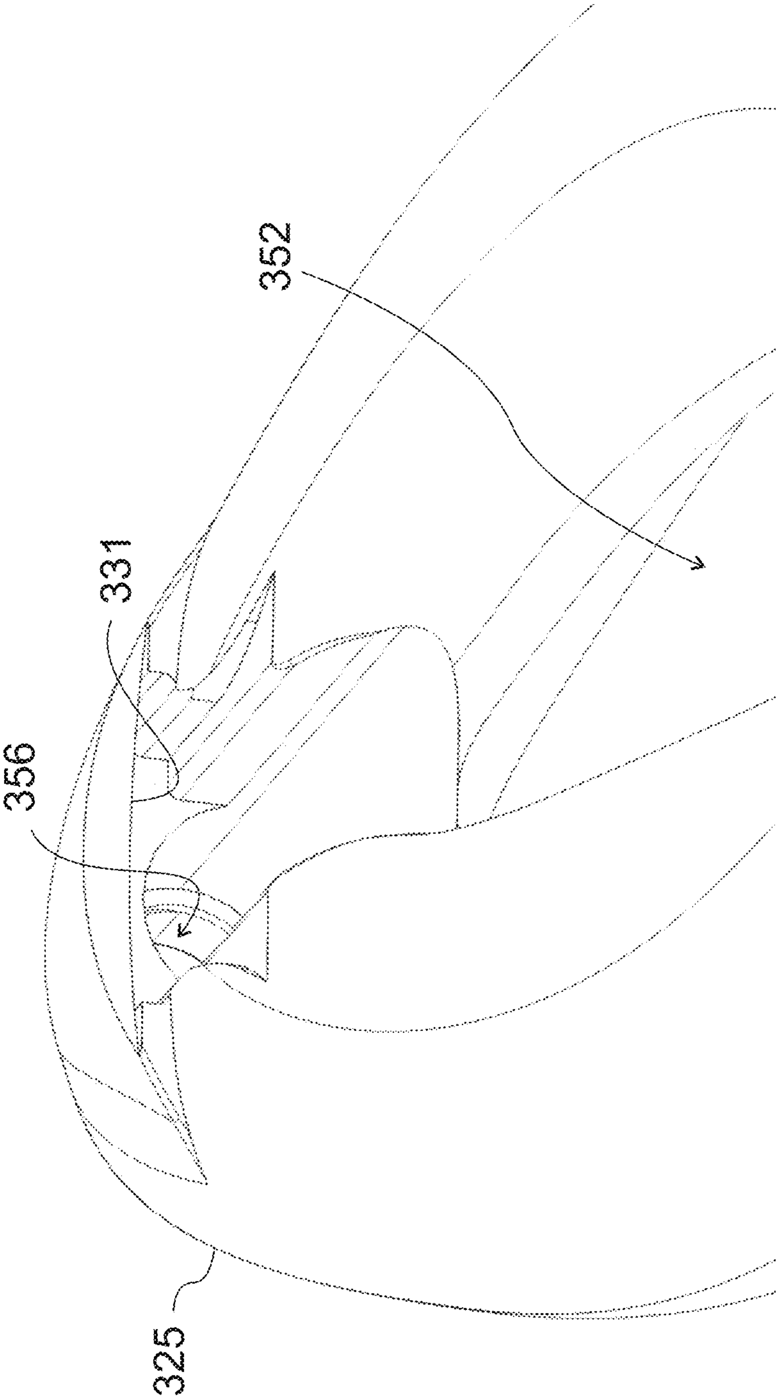
FIG. 83 illustrates the annular cushion of the fifth embodiment.

FIG. 83 illustrate an annular cushion 325 corresponding to the fifth embodiment of the laryngeal mask. FIG. 83 illustrate the annular cushion 325 in an inflated state. FIG. 83 shows a gastric hole 356 for accommodating the gastric tube, as well as a cushion opening 352 (cf. e.g. with the cushion opening 162). Furthermore FIG. 83 shows that a hood 331 is formed on the annular cushion 325 with the help of which there are formed insertion places for accommodating the release threads (cf. with the insertion places 60 in FIG. 38 and the insertion places 160 in FIGS. 64-66).

Figure 84:
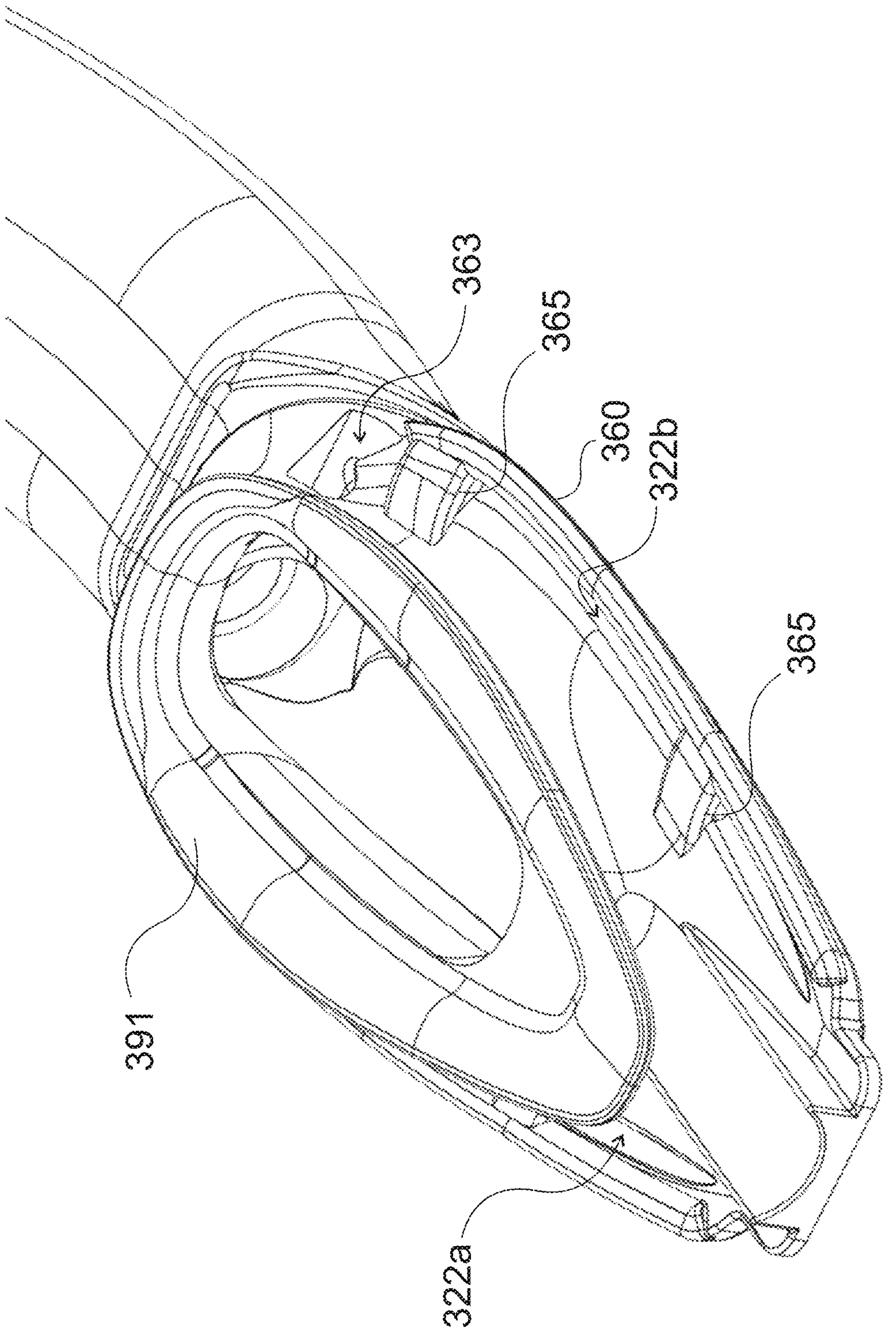
FIG. 84 illustrates a sixth embodiment in a spatial view.

FIG. 84 illustrate a sixth embodiment of the laryngeal mask. The configuration of this embodiment is similar to the fifth embodiment shown (considering the comparison of FIGS. 81 and 84), but also to the first-third embodiments (in respect of the bridge elements and the threading grooves, see the details below). Thus, this embodiment can be considered as of hybrid type.

The sixth embodiment of the laryngeal mask has a head portion 360 with a collar 391 (reception recess is formed around the respective parts of the collar 391). Furthermore, in this embodiment threading grooves 322*a* and 322*b* with bridge elements 365 are formed for release threads. The bridge elements 365 are the threading elements in this embodiment. When the threading elements are formed over a threading groove, these called bridge elements, the arrangement of these is very similar to the loops 315, 317 in FIG. 81 (accordingly, the bridge elements 365—and the bridge elements in general—could also be considered as loops).

In case of the embodiment corresponding to FIG. 81, the release thread run on the inner surface of the reception recess. However, in the embodiment of FIG. 84, the bridge elements 365 have a flat surface being in line with the surface of the reception recess. Thus, similarly to other embodiments with threading groove, the release thread runs—in the respective sections—in the wall of the reception recess, deepened to its material.

Figure 85:
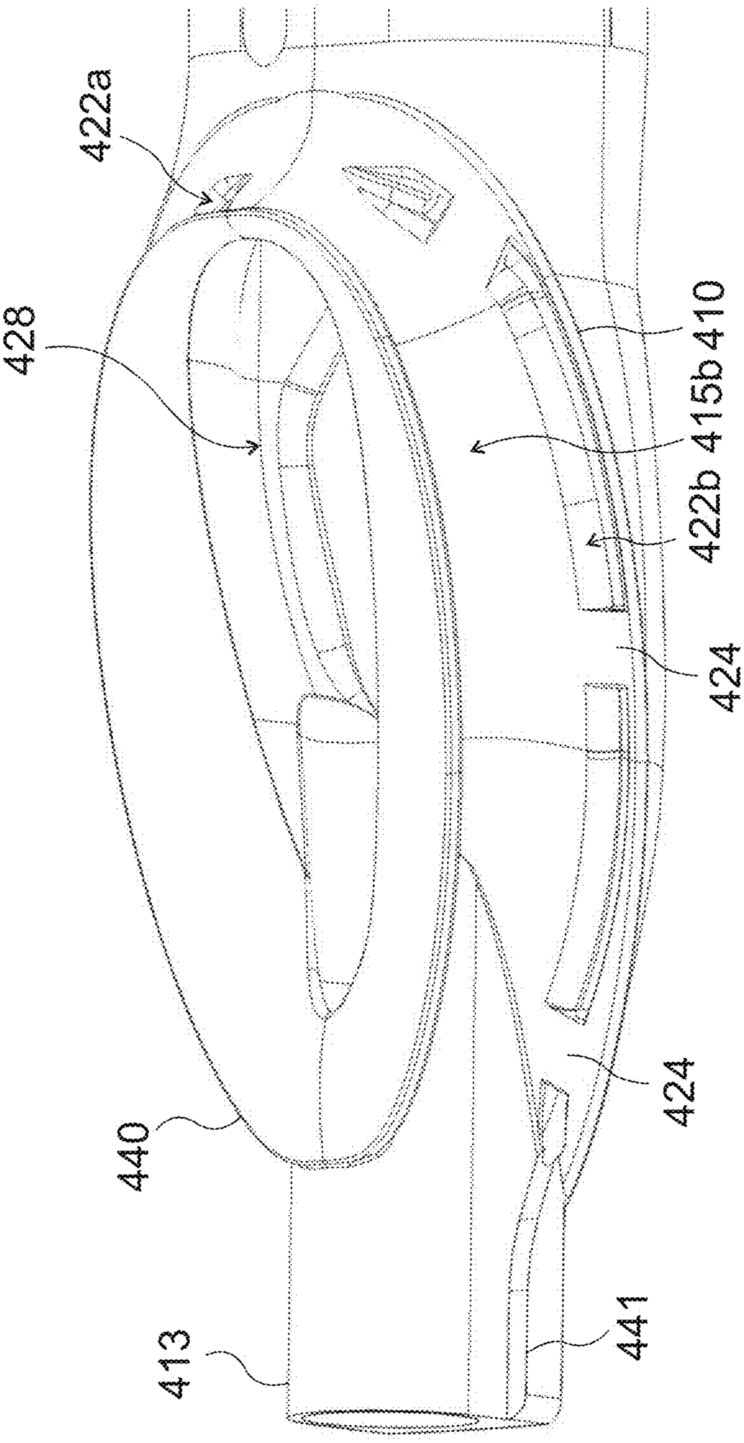
FIG. 85-87 illustrate a seventh embodiment of the invention without annular cushion in different views.
Figure 86:
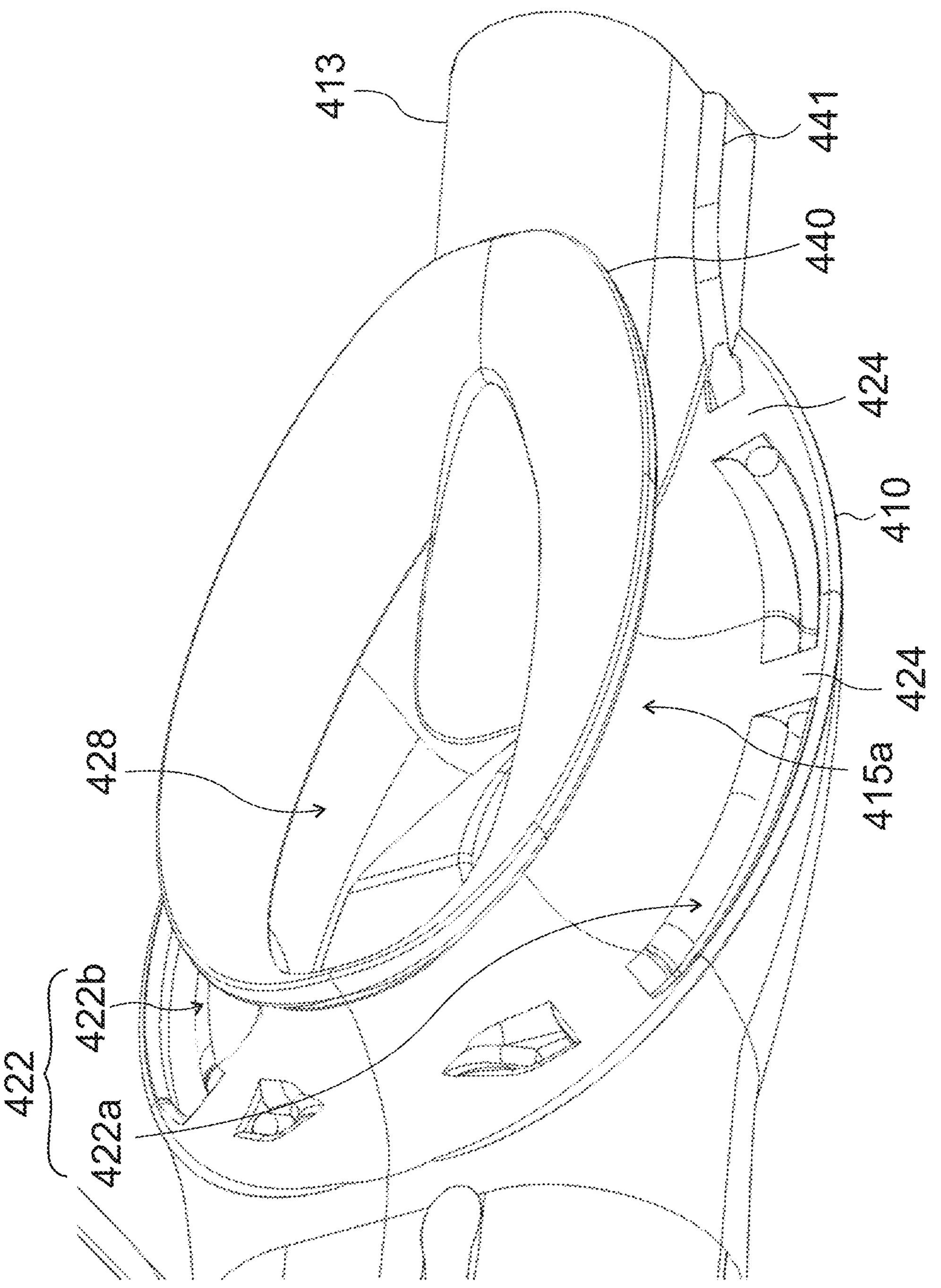
Figure 87:
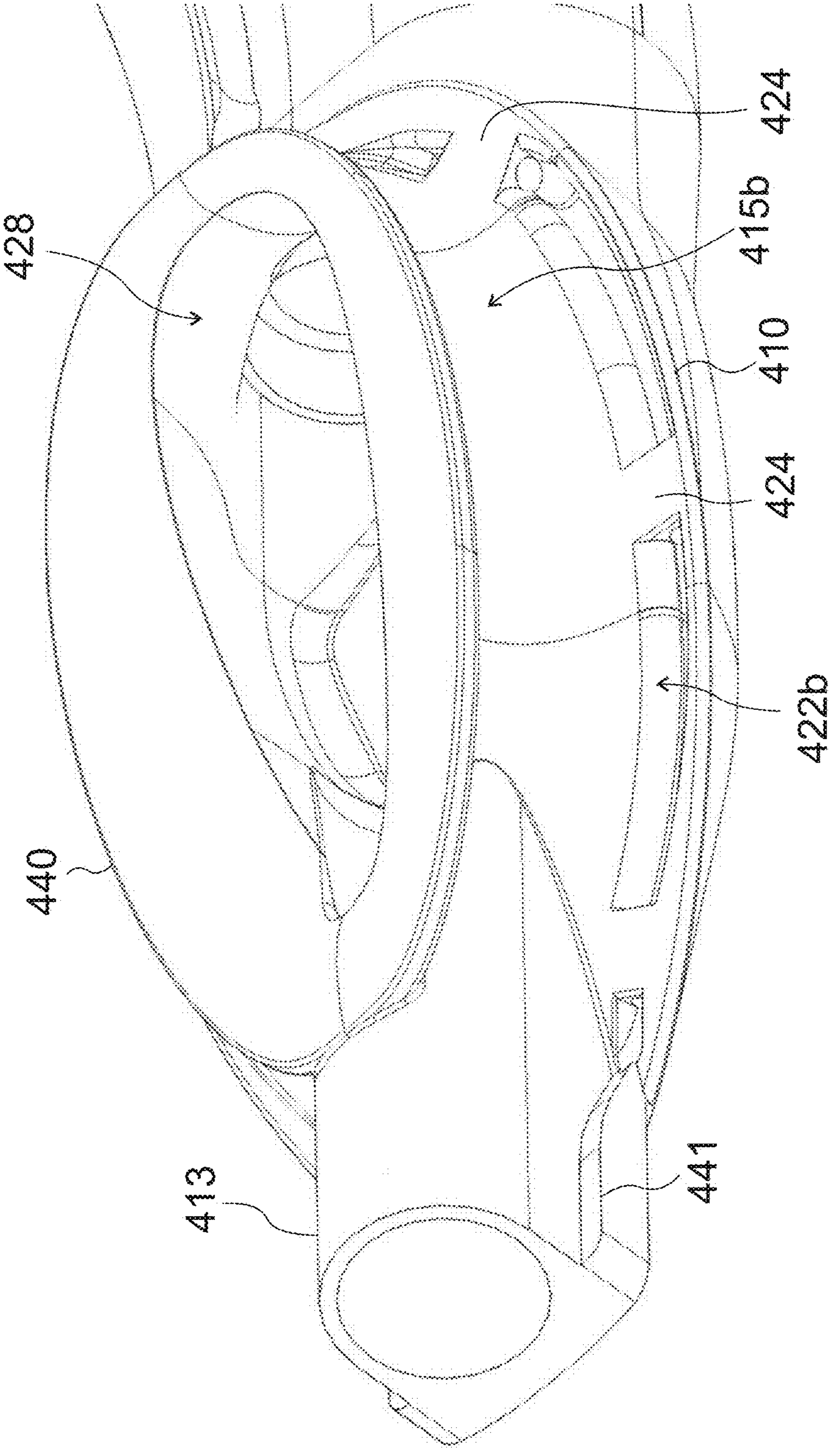

FIGS. 85-87 illustrate a seventh embodiment of the laryngeal mask. This embodiment is illustrated by the help of figures showing only a head portion 410, i.e. the seventh embodiment is illustrated without the release threads, the annular cushion and the cover element, but it can be understood how these can be applied onto it.

In FIG. 85-87 it can be observed that threading grooves 422*a*, 422*b* are formed for accommodating the release threads (the threading groove of the other side can be seen also partly; see FIG. 86 for their common notation as threading grooves 422).

The threading grooves 422 are formed similarly to the threading grooves 22 and 122 of the first-third embodiments. In accordance with this, bridge elements 424 are arranged bridging over the threading grooves 422, i.e. the anchoring of the release threads—and thereby the cover element—by the help of the bridge elements 424 is done similarly as in first-third embodiments. Based on the configuration of the threading grooves 422 it can be also understood that release threads come into them at the head proximal end of the head portion 410.

The threading grooves 422*a*, 422*b* each play a role of an extra groove (it is intended that the release thread sink into these) in the wall of the reception recess (that of the reception recesses 415*a*, 415*b*) which reception recess may be also considered to be a groove. Each of the threading grooves 422*a*, 422*b* extends from the head proximal end to the distal tip and goes with the line of the edge of the head portion, i.e. formed on the periphery of the head portion shifted with a threading groove distance (this distance is much smaller than the distance of the head portion edge and the deepest point of the corresponding reception recess) from the edge. These can be applied on the first-third embodiments, as well.

In FIG. 85 furthermore a distal tip 413, as well as a collar 440 encompassing a laryngeal opening 428 can be observed. It can be seen in this view that in this illustration gastric tube is not arranged, it can be inserted into the distal tip 413 as well as into the inner space of the head portion 410 (cf. for the arrangement of the gastric tube e.g. with the cross-sections of FIGS. 19-32).

In the present embodiment, similarly to the first, second and third embodiment, three bridge elements 424 are applied as threading elements. In this embodiment, the bridge elements 424 are similarly arranged as in the first-third embodiments. The bridge elements 424 on the two side of the laryngeal opening at the head proximal end are somewhat closer to the tube portion as the last bridge elements 24, 124 of the first-third embodiments.

FIG. 86 shows a further view of the head portion 410. In this view the threading grooves 422*a*, 422*b* formed at the two head portion edges (side edges) of the head portion 410 can be observed. In this view, furthermore passages (tunnels) under the bridge elements 424 (for the release thread) can also be observed, and it can be understood that after the last passage before the distal tip 413, the passage leads the release thread to be arranged near the distal tip 413 for running along it on the shelves 441 formed longitudinally on it. It can be observed in FIGS. 85-87 that the respective threading grooves are led onto the shelves 441 (similar shelves can be observed in FIGS. 81 and 84 along the distal tip, see such shelves also in FIG. 88A-88E, in connection with the running of the release threads at the shelves, we refer to FIG. 83, similar approach can be applied in the embodiments with shelves). It is noted that in the first, second and third embodiments, the release threads run into the annular cushion (into insertion places denoted e.g. in FIG. 38) and in the fourth embodiment into the loop 216.

In FIG. 87 a further view of the head portion 410 is shown. In this view, other passages corresponding to the bridging elements 424 can be observed, as well as we can see more into the laryngeal opening 428 inside the collar 440. Moreover, the connection (continuation, since it is preferably integral with the head portion 410) to the tube portion can be observed, but only the very beginning of the tube portion is illustrated in FIG. 87. For a first reception recess 415*a* and a second reception recess 415*b*, see FIGS. 85-87.

The configuration of the reception recesses of the head portion for accommodating the material of the annular cushion as touched upon elsewhere can be understood based on the figures of the various embodiments. In these embodiments, a first reception recess and a second reception recess are formed beside the laryngeal opening on the head portion between the head distal end and the head proximal end of the head portion for accommodating-preferably folded or rolled (rolled-up)—material of the annular cushion covered by the cover element. Accordingly, the reception recesses are opened on the side of the laryngeal opening, i.e. face against the laryngeal opening by their opened side. It is noted that the reception recess may also be called (reception) indentation, also receiving or accommodating recess/indentation.

Herebelow, some relevant aspects of the configuration of the reception recesses are detailed.

To go into some details, we cite here namely FIG. 10, FIG. 59, FIG. 74 (for the reception recesses 215*a*, 215*b*, denoted in this figure), FIG. 81, FIG. 84 and FIGS. 85-87 for illustrating these in the respective head portions 10, 110, 210, 310, 360, 410. Moreover, the cross-sections of FIGS. 19-32, FIG. 39-54 show many details, and separate emphasis is taken on FIG. 55 where the shape of the reception recesses 15, 15*b* can be observed due to the inflated state of the annular cushion 25.

In FIG. 55 it can be observed that the reception recesses 15*a*, 15*b* are formed between the main part of head portion 10 and the collar 29 (some part of its shape can be observed on both sides of the gastric tube 13 from inside the annular cushion). Since the gastric tube is arranged in the illustrated embodiments, the reception recesses of the two sides start at the distal tip where the gastric tube goes into the inner space of the head portion. If we consider a side view of the head portions, it can be seen that at the distal tip, there is not too much space for the annular cushion, but after the entrance of the distal tip (incorporating the gastric tube) into the inner space of the head portion (i.e. in the direction of the head proximal end), a reception recess with a comparatively large depth starts.

Comparing the various embodiments to each other, it can be seen that the reception recess is substantially also not present at the head proximal end of the head portion, where different configurations are formed in the various embodiments.

Therefore, the reception recesses can be practically defined in all embodiments between approximately two points. A first point is at the distal tip where the gastric tube enters the inner space of the head portion and another point for the end of the reception recess can be defined at the head proximal end, namely that point where the collar have an inward-turn around the laryngeal opening (at the head proximal end the collar have a full—180°—turn, i.e. the collar turns inwards from both sides, which shows the end of the reception recess on both sides of the elongated laryngeal opening).

If we consider the configuration of the collar e.g. in FIG. 59, it can be also said—as a corresponding but a little bit alternative definition—that the reception recess is defined in correspondence with the collar. Namely, the collar has an inner periphery and an outer periphery, and if we consider a line connecting the head distal end and the head proximal end centrally in the head portion, the reception recesses can be defined parallelly to this line connecting the inner periphery portions of the collar on this line (this is a section of a straight line).

In the above defined parts corresponding strictly to the reception recess, the reception recess has a cross-section of approximately a large 'C' letter (or approximately a large 'U' latter tilted to its side). See the following figures: in the first embodiment the reception recess starts approximately at FIG. 25 (at the distal tip) and ends somewhere after FIG. 28 (until an inward-turning of the collar 29, the reception recesses can be identified based on the collar 29 which is denoted in those figures where the collar 29 does not still turn inwards); in the second embodiment the reception recess approximately starts FIG. 45 and ends at FIG. 50 (can be identified also by the help of the collar 29). Considering these cross-sections, it can be said also that the reception recess starts even along the distal tip, e.g. from FIG. 23, containing FIG. 24 and analogously from FIG. 43 containing FIG. 44. The configuration of the reception recesses 215*a*, 215*b* can be observed also in FIG. 75 (see also the configuration of the collar 241 in this figure).

These cross-sections illustrate that the reception recess has a varying depth from the head distal end to the head proximal end the depth first increases (approx. until a bit after the centre of the head portion in this direction) and after that decreases. This varying depth has good effect on the inflation and the seal of the annular cushion. The configuration helps that an annular cushion having thin material can be utilized which is well protected.

It can be understood that on the two sides of the laryngeal opening the material of the cushion element can be packed into the above defined reception recess, and referring to the figures showing the arrangement of the annular cushion (e.g. FIG. 2 and FIG. 33), it can be understood that by packing the material of the annular cushion into these reception recesses, the covered (packed) sizes of the assembled head portion with a cover element can be lowered a much in width—i.e. can be narrowed—compared to the inflated state.

It can be also understood that at the distal tip there is no need to make this narrowing particularly, since the head portion has the largest width approximately—i.e. somewhere around—its centre part longitudinally (i.e. along the head portion edge) and that at the head proximal end the annular cushion can be arranged well even without a reception recess portion. Because of the geometry of the annular cushion, it can be also said that at the head proximal end it would not be an easy task to arrange the annular cushion better packed. It is noted that the packing at the head proximal end has been found being satisfactory. This can be understood based on FIG. 8A and FIG. 34, and also based on figures showing that the annular cushions 85, 125 separately namely FIGS. 36-38 and FIGS. 63-65.

In FIGS. 88A-88E variants for arranging a thread channel is illustrated. In this respect the first, second and third embodiment is referred to for similar arrangement of the thread channel. In connection with these embodiments, it was given that preferably, at least one thread channel is formed along the tube portion or connected to the tube portion along the tube portion, for which FIGS. 88A-88E illustrate exemplary arrangements.

Thus, FIGS. 88A-88E shows further respective embodiments after the seventh embodiment shown in FIGS. 85-87. These could also receive serial numbers continuing after the seventh. Throughout FIGS. 88A-88E the various laryngeal masks has a head portion 510 with threading grooves 522*a*, 522*b*.

Figure 88C:
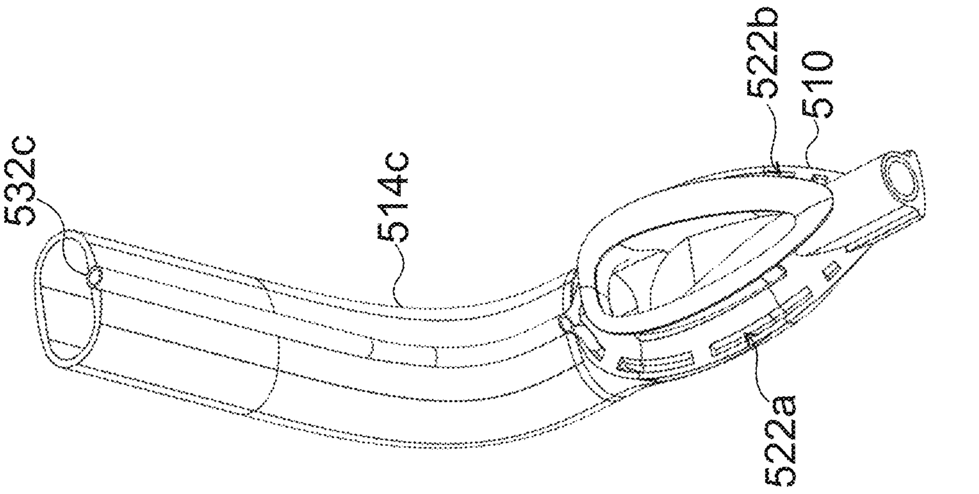
FIGS. 88A-88E illustrate further variants for arranging the thread channel.

As illustrated in the figures, like in FIGS. 8A-8B, it was chosen to arrange the release threads 40*a*, 40*b* in the thread channel 32 arranged on the outer side of the tube portion (attached to it) centrally on the flattened side thereof (the tube portion preferably has a flattened configuration). In FIG. 88C, a thread channel 532*c* is similarly arranged along a tube portion 514*c*.

Naturally, the thread channel may be arranged elsewhere on the flattened side (not only centrally) between the head portion and the tube proximal end of the tube portion. Such variant is illustrated in FIG. 88A. In this embodiment, a thread channel 532*a* starts centrally at the head portion 510, but goes off-centred and reaches the tube proximal end of a tube portion 514*a* in this way.

Figure 88B:
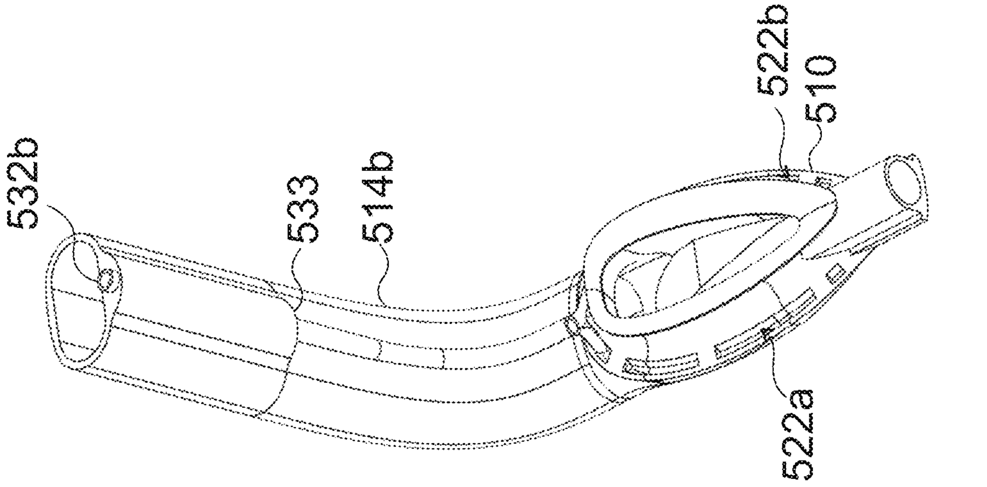
Figure 88A:
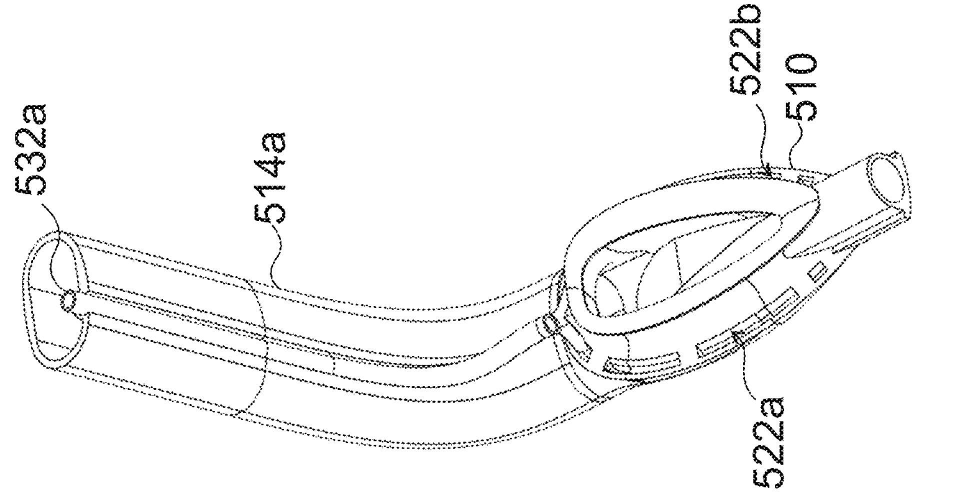
Figure 88E:
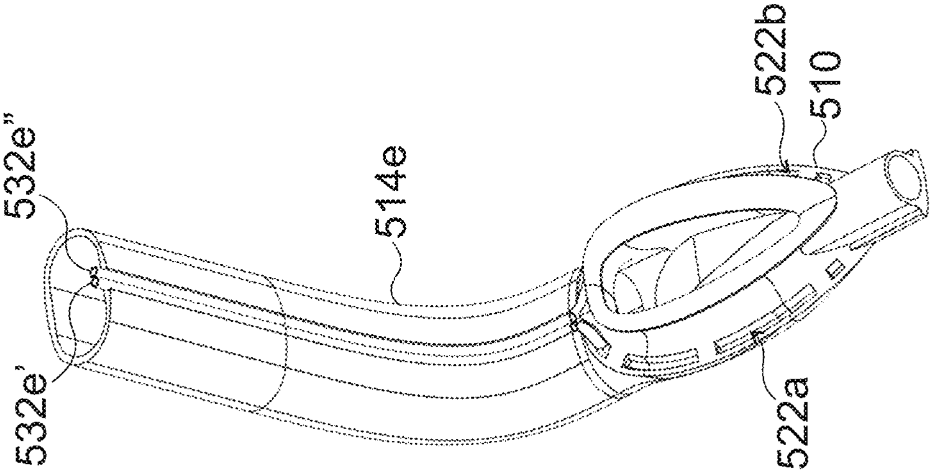
Figure 88D:
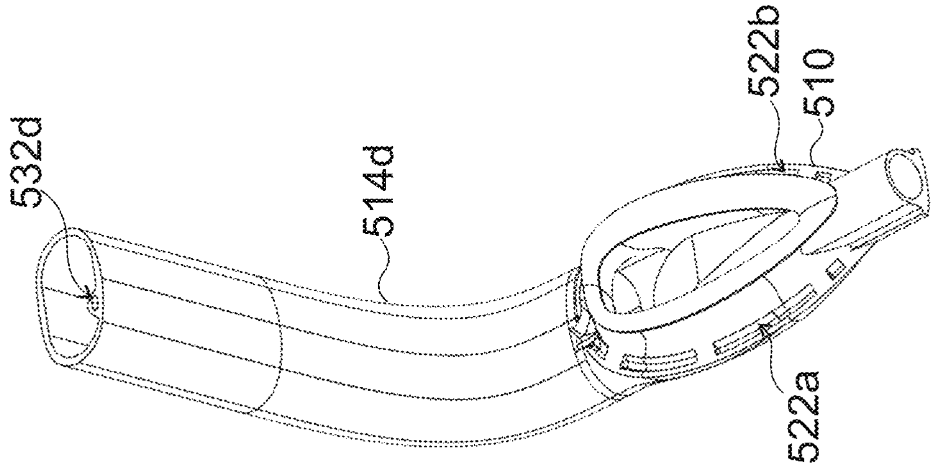

Moreover, other arrangement for the release threads as well as for the thread channel is conceivable. For example, it is noted that the thread channel can be integrated partly or fully (i.e. at least partly) into the wall of the tube portion. This integrated configuration is conceivable mainly in two ways:

- Like in FIG. 88B, it is integrated such that a thickening 533 of the tube wall is formed on the flattened side of a tube portion 514*b* (so as to be outside the illustrated tube portion) and the thread channel will be integrated or formed in the thickening 533. The thickening 533 is formed at least partly between the head portion 510 and the tube proximal end of the tube portion 514*b* (it could start where the threading groove or threading groove pieces has an end, i.e. where the thread channel starts or the thickening can be formed at the tube proximal end of the tube portion, like in FIG. 88B). If the thickening would be applied throughout between the head portion and the tube proximal end, then no separate thread channel is to be arranged but only a channel type tunnel in the thickening.
- FIG. 88D illustrates that a thread channel 532*d* can be integrated also in a way that there is no thread channel is attached to the tube portion, but the thread channel 532*d* is integrated in the wall of the tube portion 514*d* so as that the thread channel 532*d* protrudes in the inner direction but formed independently from the other channels (see above the channels 44, 46) within the tube portion 514*d*, i.e. this is a different channel (it is emphasized that the thread channel is a separated channel from those in all of the embodiments with thread channel). This type of thread channel could protrude outside. If the threading groove or the threading groove pieces runs directly into this inner channel and it is formed until the tube proximal end than no separate thread channel is to be formed but the release threads can be arranged in the integrated channel (tunnel) itself, as it is illustrated in FIG. 88D. It is conceivable that the leading of the release threads along the tube portion in accordance with FIG. 88D can be implemented in the first embodiment in a way that the threading groove pieces 26 go inside the wall of the tube portion just like the thread channel (cf. with the tunnel like threading groove pieces 26 mentioned above).
- FIG. 88E shows a further variant, in which a respective thread is arranged in a respective (separate) thread channel 532*e*' and 532*e*", which are arranged along a tube portion 514*e*.

A mixed configuration of the above is also conceivable.

The above are applicable naturally to the first and second embodiment, as well as to the third embodiment, where the release threads are also arranged in a closed thread channel (cf. FIG. 57), but these thread channels are also applicable in another embodiments.

It is noted that also such variations are conceivable for the features of the invention that are preferred from the point of view of mass production, but which constitutes alternatives of the illustrated embodiments.

The invention is of course not limited to the preferred embodiments described in detail, but further variants, modifications and improvements are possible within the scope of protection defined by the claims. Furthermore, all embodiments that can be defined by any arbitrary dependent claim combination belong to the invention.

The invention claimed is:

1. A laryngeal mask, comprising a head portion having a head distal end and a head proximal end, and a tube portion having a tube distal end and a tube proximal end opposite to the tube distal end, wherein the tube distal end of the tube portion is arranged on the head proximal end of the head portion, a channel is formed between a laryngeal opening of the head portion and the tube proximal end of the tube portion and the laryngeal opening is adapted for fitting onto a trachea, an annular cushion arranged on the head portion around the laryngeal opening, and a cover element at least partly encompassing the annular cushion and at least partly covering the laryngeal opening, characterized in that the cover element is made of a through-breathable material, the laryngeal mask further comprising a release element fixing the cover element to the head portion, wherein the release element has a first puller portion and the cover element has a second puller portion, the first puller portion and the second puller portion are pullable at the tube proximal end of the tube portion, and the release element is adapted for releasing the fixing of the cover element to the head portion in case the first puller portion of the release element is pulled at the tube proximal end of the tube portion, and the first puller portion and the second puller portion are configured so that in case of joint pulling of the first puller portion (48, 148) and the second puller portion at the tube proximal end of the tube portion, the fixing with the release element of the cover element to the head portion is releasable and thereby making the cover element removable.

2. The laryngeal mask according to claim 1, characterized in that the cover element has a first row of threading holes and a second row of threading holes along respective edges of the cover element located between the head distal end and the head proximal end of the head portion, the laryngeal mask further comprises first threading elements and second threading elements formed on the head portion along respective edges of the head portion extending between the head distal end and the head proximal end of the head portion, and the release element is formed by a first release thread and a second release thread having the first puller portion, arranged inserted into or passing through the first threading elements and the second threading elements, respectively, and passing through the first row of threading holes and the second row of threading holes, respectively, in a manner so as to fix the cover element along the respective edges of the cover element to the head portion, wherein the first release thread and the second release thread are releasable from the first threading elements and the first row of threading holes, as well as from the second threading elements and the second row of threading holes, respectively.

3. The laryngeal mask according to claim 2, wherein the first release thread and the second release thread share the first puller portion as a common first puller portion, or wherein the first puller portion includes a first segment corresponding to the first release thread and a second segment corresponding to the second release thread, each has a respective first puller portion (48, 148), or have a common first puller portion.

4. The laryngeal mask according to claim 3, characterized in that the first puller portion includes the first segment corresponding to the first release thread and the second segment corresponding to the second release thread the first release thread and the first release thread and the second release thread arc part of a single thread.

5. The laryngeal mask according to claim 3, characterized in that the first puller portion includes the first segment corresponding to the first release thread and the second segment corresponding to the second release thread and the first release thread and the second release thread are separate threads.

6. The laryngeal mask according to claim 2, characterized in that a first threading groove and a second threading groove for the first release thread and the second release thread, respectively, are formed in the head portion, at least a part of the first threading elements and the second threading elements are formed by bridge elements bridging the first threading groove and the second threading groove, respectively.

7. The laryngeal mask according to claim 6, characterized in that the first threading groove and the second threading groove are formed along the laryngeal opening at the respective edges of the head portion between the head distal end and the head proximal end of the head portion.

8. The laryngeal mask according to claim 2, characterized in that at least one thread channel is formed along the tube portion or connected to the tube portion along the tube portion, and the first release thread and the second release thread are arranged in the at least one thread channel.

9. The laryngeal mask according to claim 8, characterized in that between a head end of a thread channel, of the at least one thread channel, and the head portion the first release thread and the second release thread are arranged in respective interconnection threading groove pieces, wherein at the head end of the thread channel being at the head portion the interconnection threading groove pieces have a junction, and close a thread angle between 10° and 100°.

10. The laryngeal mask according to claim 9, characterized in that the interconnection threading groove pieces are straight.

11. The laryngeal mask according to claim 1, characterized in that a first reception recess and a second reception recess are formed beside the laryngeal opening on the head portion between the head distal end and the head proximal end of the head portion for accommodating material of the annular cushion covered by the cover element.

12. The laryngeal mask according to claim 1, characterized in that the first puller portion and the second puller portion are connected to each other at the tube proximal end of the tube portion.

13. The laryngeal mask according to claim 12, characterized by comprising a pullable end element arranged on the tube proximal end of the tube portion and the first puller portion and the second puller portion are connected to each other by means of the pullable end element.

14. The laryngeal mask according to claim 1, characterized by comprising a connector element inserted onto the tube proximal end of the tube portion, having a connection pin, and an inflation arrangement for inflating the annular cushion, wherein the inflation arrangement comprises an inflation tube being in connection with an inner space of the annular cushion, and a valve arranged on the end of the inflation tube being opposite to the head portion, connectable onto the connection pin for maintaining an open state of the valve.

* * * * *